United States Patent
Crabb et al.

(10) Patent No.: US 11,654,027 B2
(45) Date of Patent: *May 23, 2023

(54) METHOD OF SURGICALLY PROVIDING A TRANS-MALE PATIENT WITH A NEOPENIS INCLUDING MALLEABLE PENILE INSERTS INSIDE AN ARTIFICIAL TUNICA

(71) Applicant: Coloplast A/S, Humlebaek (DK)

(72) Inventors: Rachael Anne Bergstrom Crabb, Saint Paul, MN (US); Neal Poucher, North Oaks, MN (US); Michael M. Witzmann, Minneapolis, MN (US); Eric Watschke, Minneapolis, MN (US); Melissa Curran-Moore, Minneapolis, MN (US); Thomas Kubalak, Wayzata, MN (US)

(73) Assignee: Coloplast A/S, Humlebaek (DK)

( * ) Notice: Subject to any disclaimer, the term of this patent is extended or adjusted under 35 U.S.C. 154(b) by 49 days.

This patent is subject to a terminal disclaimer.

(21) Appl. No.: 17/547,266

(22) Filed: Dec. 10, 2021

(65) Prior Publication Data
US 2022/0160509 A1    May 26, 2022

Related U.S. Application Data

(63) Continuation of application No. 16/848,839, filed on Apr. 15, 2020, now Pat. No. 11,229,518, which is a continuation of application No. 16/517,667, filed on Jul. 22, 2019, now Pat. No. 10,722,366, which is a
(Continued)

(51) Int. Cl.
*A61F 2/26* (2006.01)

(52) U.S. Cl.
CPC ........ *A61F 2/26* (2013.01); *A61F 2250/0003* (2013.01)

(58) Field of Classification Search
CPC .......................... A61F 2/26; A61F 2250/0003
See application file for complete search history.

(56) References Cited

U.S. PATENT DOCUMENTS

| | | |
|---|---|---|
| 4,009,711 A | 3/1977 | Uson |
| 4,335,714 A | 6/1982 | Edgerton et al. |
| 4,522,198 A | 6/1985 | Timm et al. |

(Continued)

FOREIGN PATENT DOCUMENTS

| | | |
|---|---|---|
| BY | 13194 C1 | 6/2010 |
| CN | 101836905 A | 9/2010 |

(Continued)

OTHER PUBLICATIONS

Chang et al., Forearm Flap in One-Stage Reconstruction of the Penis, Plastic and Reconstructive Surgery, Aug. 1984, vol. 74, No. 2, p. 251-258.

(Continued)

*Primary Examiner* — Suba Ganesan
(74) *Attorney, Agent, or Firm* — Coloplast Corp., Coloplast A/S; Nick Baumann

(57) ABSTRACT

A method of surgically providing a trans-male patient with a neopenis includes inserting an implantable penile prosthesis into an inverted vagina, where the implantable penile prosthesis includes a pair of malleable penile inserts inside an artificial tunica.

9 Claims, 65 Drawing Sheets

Related U.S. Application Data continuation of application No. 15/726,412, filed on Oct. 6, 2017, now Pat. No. 10,398,558.

(60) Provisional application No. 62/405,300, filed on Oct. 7, 2016.

(56) References Cited

U.S. PATENT DOCUMENTS

| | | | |
|---|---|---|---|
| 4,791,917 | A | 12/1988 | Finney |
| 6,475,137 | B1 | 11/2002 | Elist |
| 8,727,965 | B2 | 5/2014 | Williams et al. |
| 9,724,197 | B2 | 8/2017 | Daniel |
| 10,398,558 | B2 | 9/2019 | Crabb |
| 2005/0014993 | A1 | 1/2005 | Mische |
| 2007/0142700 | A1 | 6/2007 | Fogarty et al. |
| 2011/0054250 | A1 | 3/2011 | Morningstar |
| 2011/0218396 | A1 | 9/2011 | Williams et al. |
| 2012/0022323 | A1 | 1/2012 | Forsell |
| 2012/0022324 | A1 | 1/2012 | Forsell |
| 2012/0271101 | A1 | 10/2012 | Tan |
| 2016/0089241 | A1 | 3/2016 | Taylor |
| 2018/0200060 | A1* | 7/2018 | Gomez-Llorens ........ A61F 2/26 |

FOREIGN PATENT DOCUMENTS

| | | |
|---|---|---|
| CN | 202386821 U | 8/2012 |
| EP | 0682923 A1 | 11/1995 |
| EP | 1820473 A1 | 8/2007 |
| EP | 2767261 A1 | 8/2014 |
| EP | 2608744 B1 | 11/2016 |
| RU | 2065728 C1 | 8/1996 |
| RU | 2157663 C2 | 10/2000 |
| RU | 26412 U1 | 12/2002 |
| RU | 2234258 C2 | 8/2004 |
| RU | 2246909 C1 | 2/2005 |
| RU | 2309683 C2 | 11/2007 |
| RU | 2005137227 A | 4/2015 |
| RU | 2557706 C1 | 7/2015 |
| WO | 9634211 A1 | 10/1996 |
| WO | 9922677 A2 | 5/1999 |
| WO | 9959506 A1 | 11/1999 |
| WO | 03103537 A2 | 12/2003 |
| WO | 2006096001 A1 | 9/2006 |
| WO | 07096354 A1 | 8/2007 |
| WO | 10079795 A1 | 7/2010 |
| WO | 11109026 A1 | 9/2011 |
| WO | 2015200784 A2 | 12/2015 |
| WO | 17009580 A1 | 1/2017 |

OTHER PUBLICATIONS

Mulcahy, Use of penile implants in the constructed neophallus, International Journal of Impotence Research, 2003, vol. 15, No. 5, p. 129-131.

Cohen et al., Novel Technique for Proximal Bone Anchoring of Penile Prosthesis after radial Forearm Free Flap Neophallus, 2017.

Zuckerman et al., Penile Prosthesis Implantation in Patients with a History of Total Phallic Construction, International Society for Sexual Medicine, 2015, vol. 12, p. 2485-2491.

Shane D Morrison et al. Phalloplasty: A Review of Techniques and Outcomes. Plast Reconstr Surg. Sep. 2016, N138(3),p. 594-615.

* cited by examiner

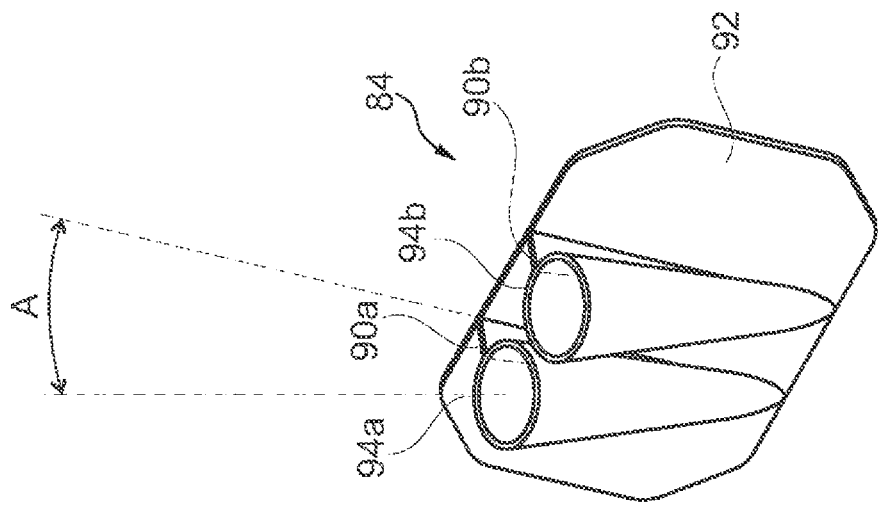
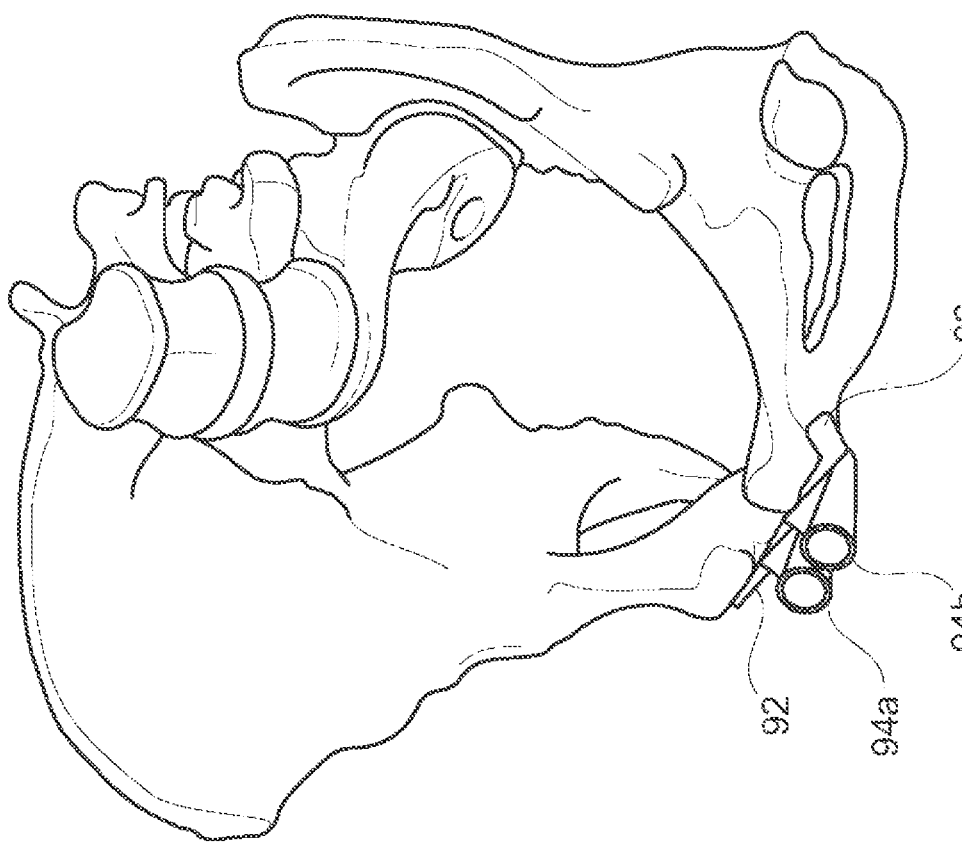

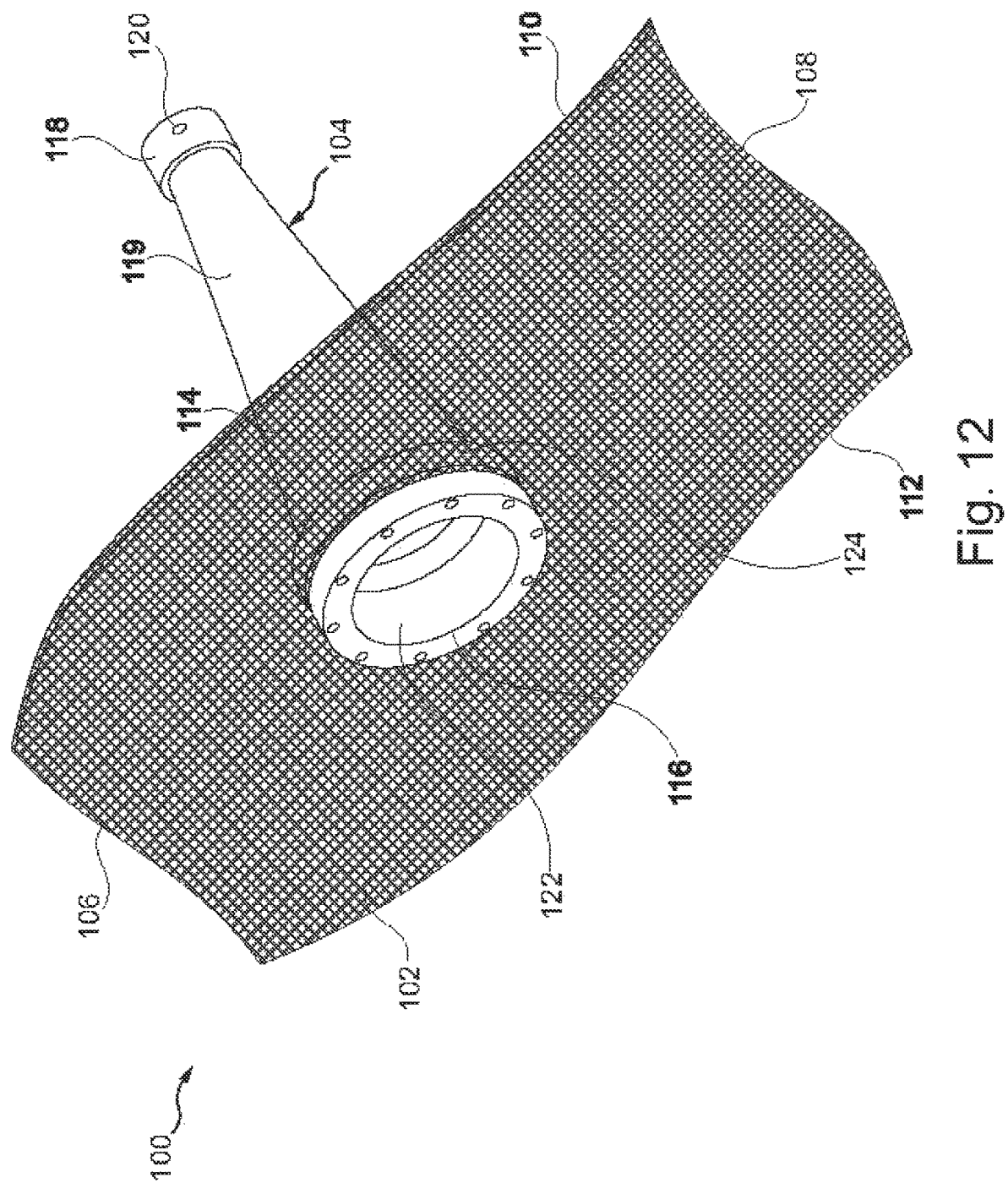

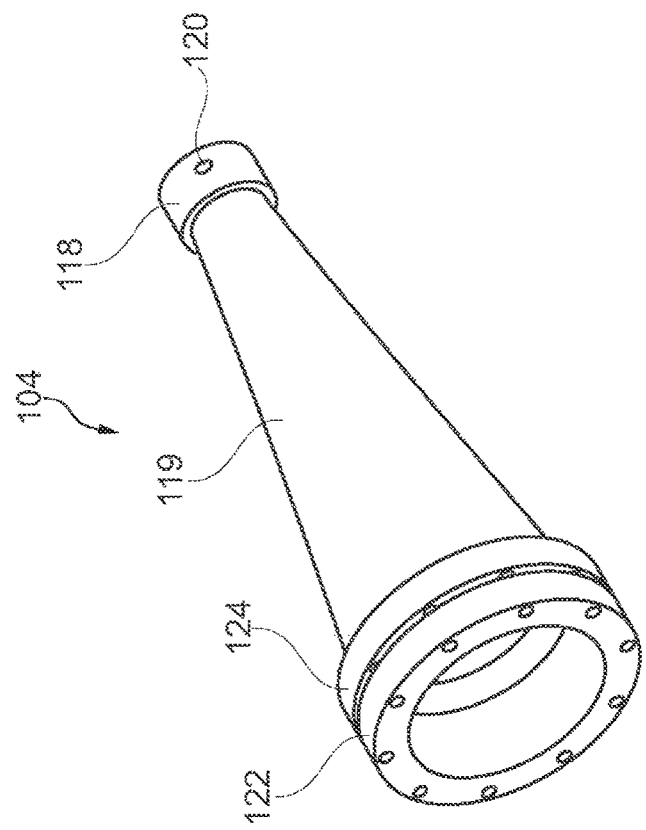
Fig. 13B
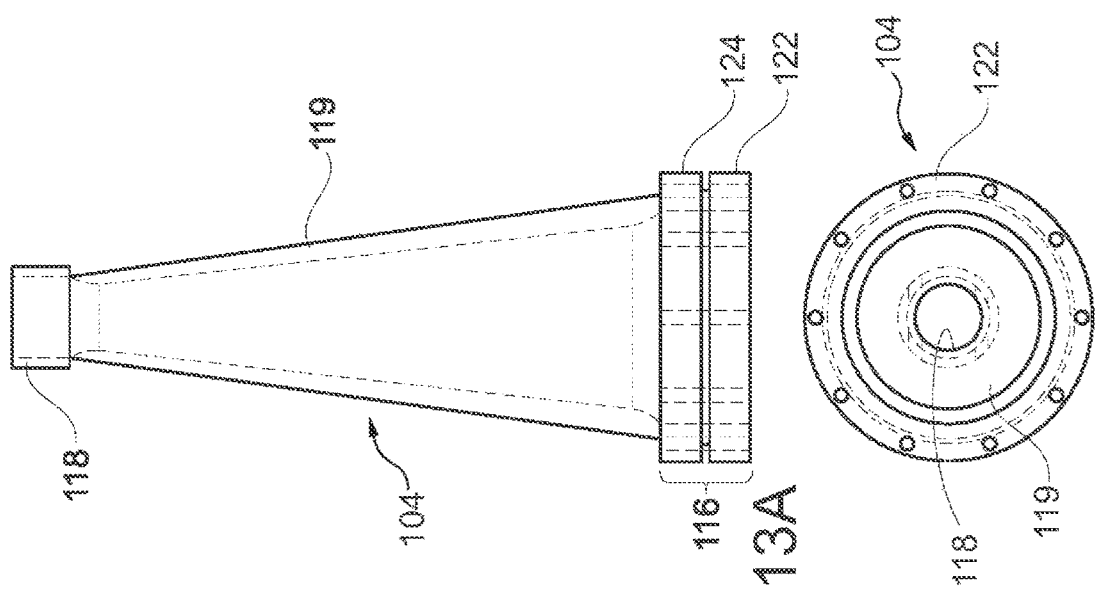
Fig. 13A
Fig. 13C

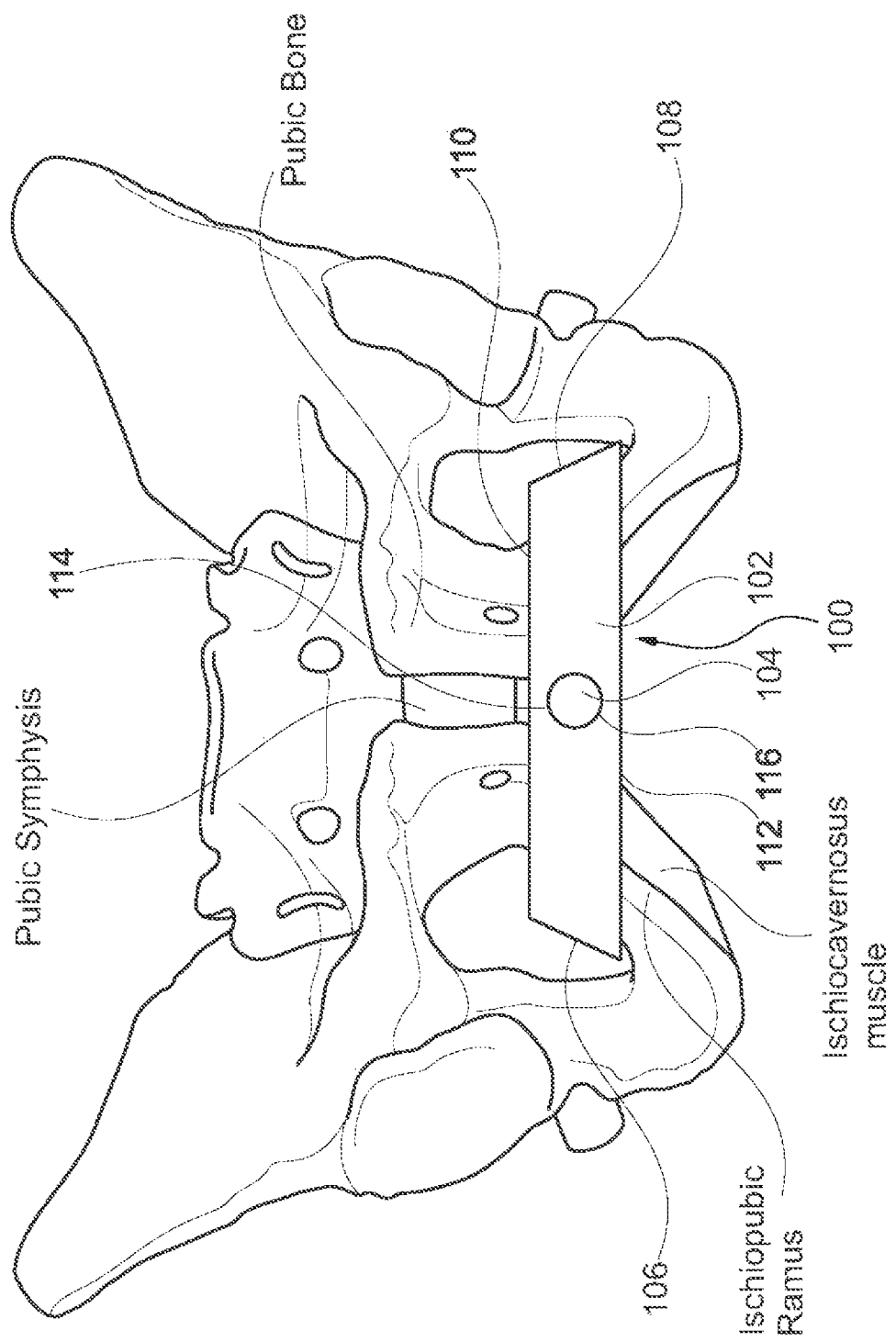

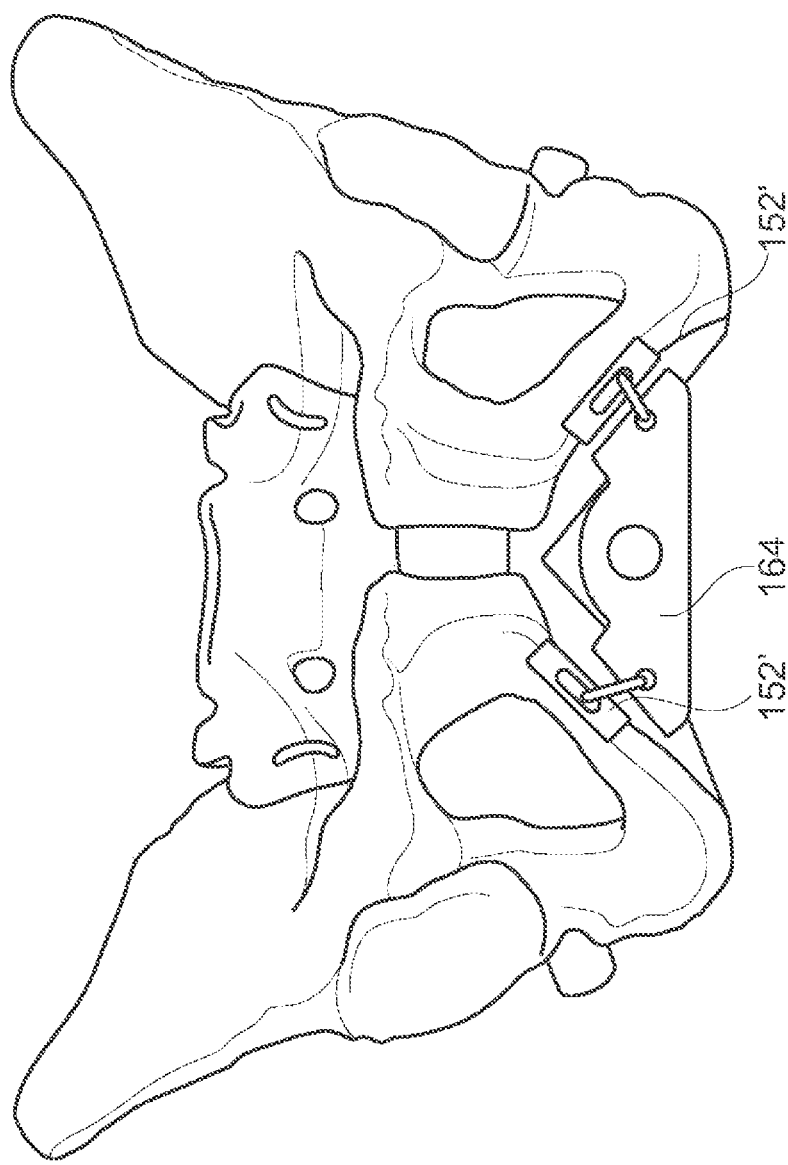

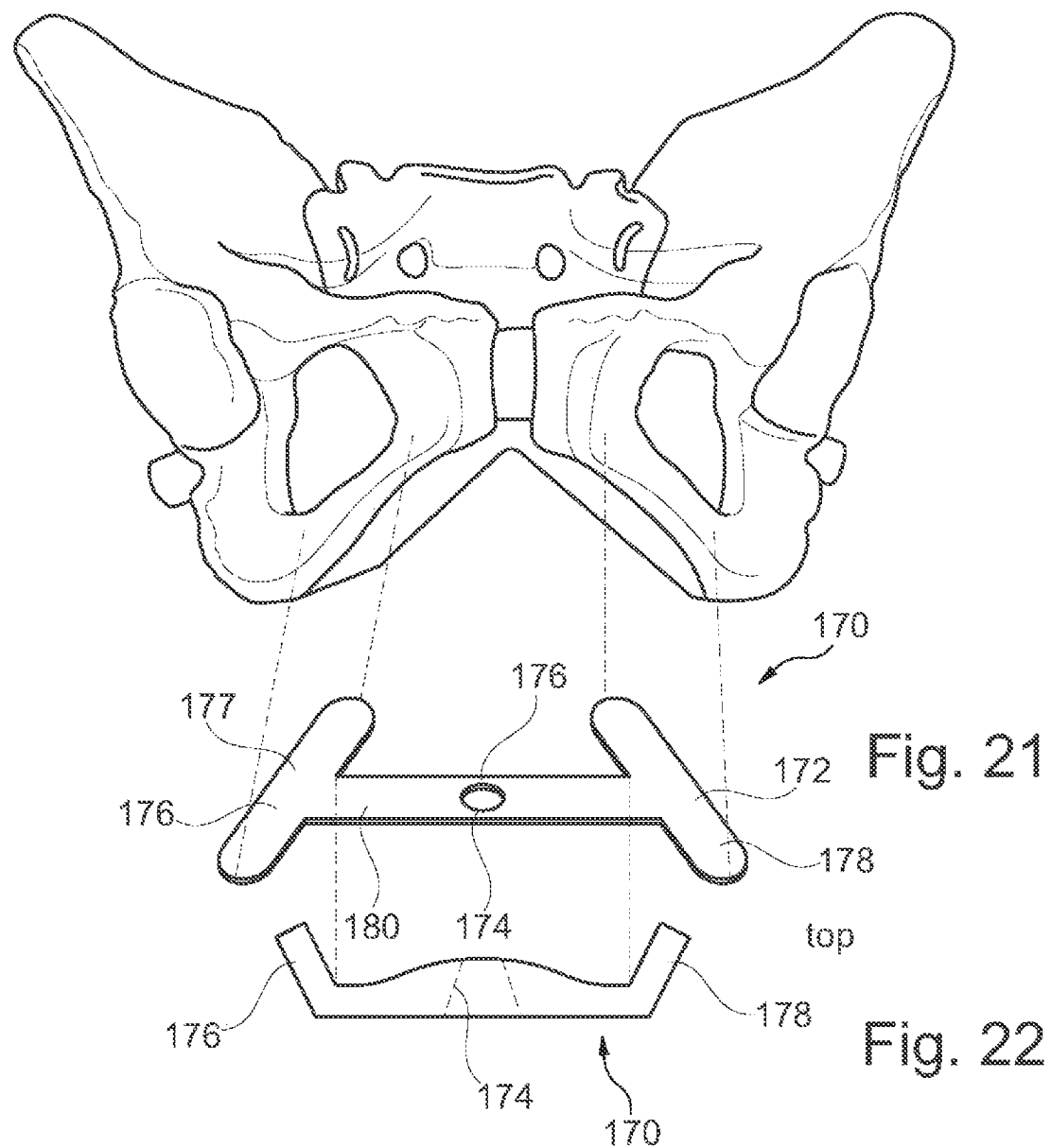

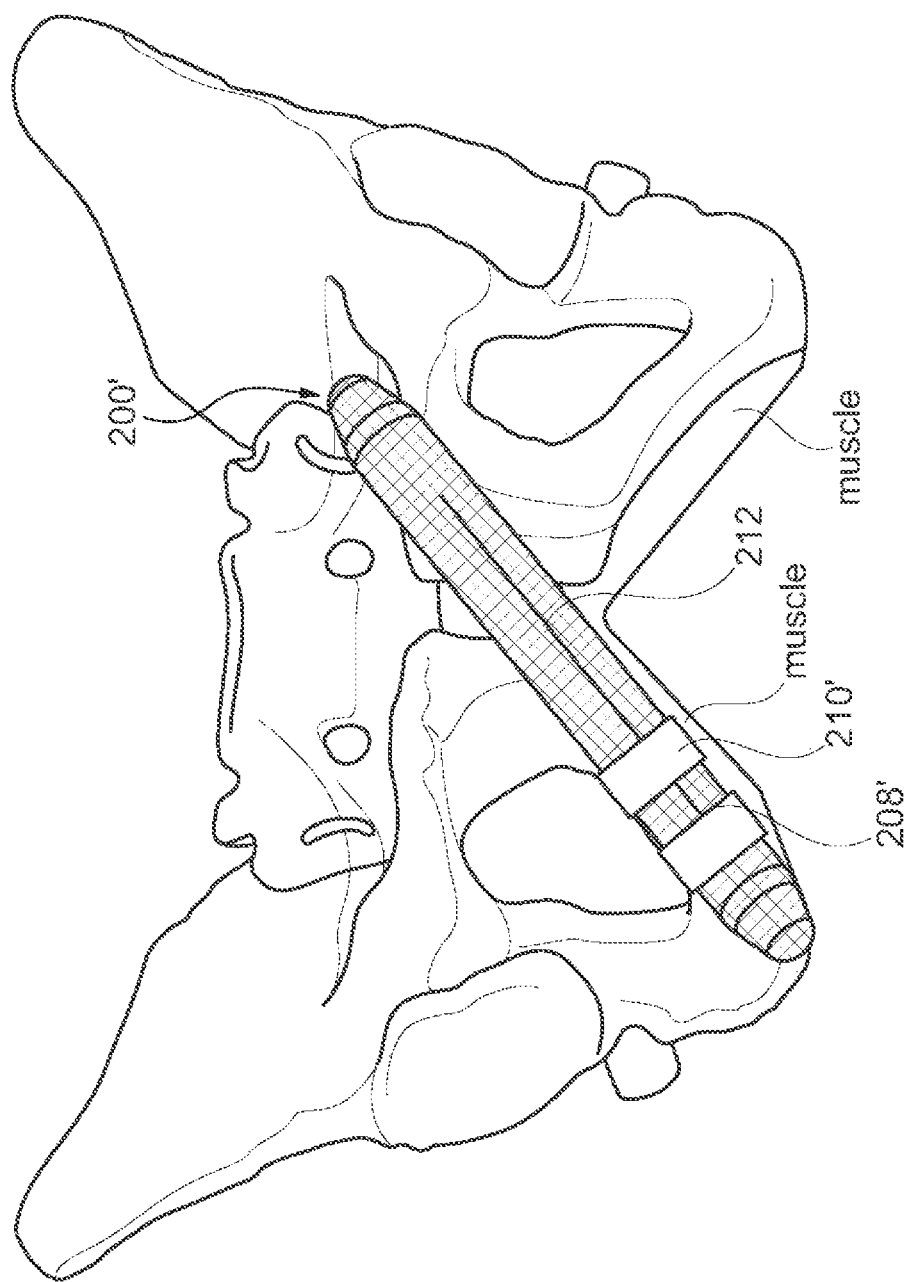

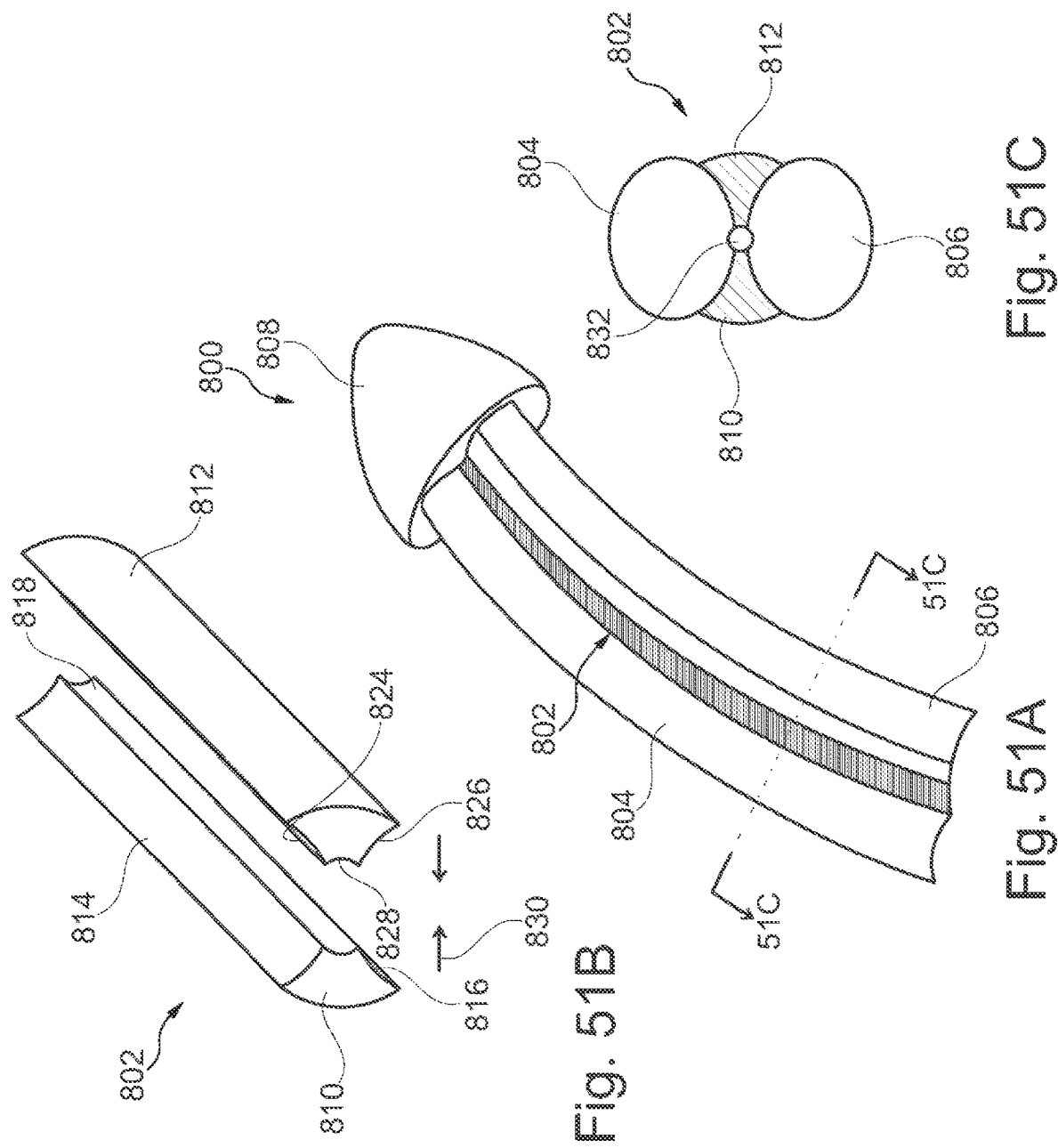

METHOD OF SURGICALLY PROVIDING A TRANS-MALE PATIENT WITH A NEOPENIS INCLUDING MALLEABLE PENILE INSERTS INSIDE AN ARTIFICIAL TUNICA

BACKGROUND

Gender is an internal sense of being male or female. Sex is a physical condition of the body that is a combination of bodily characteristics including chromosomes, hormones, internal and external reproductive organs, and secondary characteristics. Transgender is an adjective to describe people whose identity, or expression, or behavior, or sense of self does not conform to their sex as assigned at birth. Gender affirming surgery is a procedure to surgically alter a patient's body so that features of the physical body align with the patient's gender identity.

Some people who are assigned the female sex at birth have a male gender identity and desire to have surgery to provide their body with a genital appearance, for example through a phalloplasty procedure to provide the person with a neophallus, so that their physical characteristics conform with their sense of self.

Some natal males experience a birth defect or an injury to their penis and have a new penis reconstructed (a neopenis), which can include a neophallus formed from tissue and a prosthetic implanted in the neophallus.

Surgeons and patients would welcome improved penile implant systems and methods of implanting a penile prosthetic in a neophallus.

SUMMARY

Devices, penile implant systems, and methods of implanting the devices and the penile implants are disclosed to provide a person who is assigned the female sex at birth with a genital appearance that conforms with their male gender identity.

Devices, penile implant systems, and methods of implanting the devices and the penile implants are disclosed to provide a person who was assigned the female sex at birth with a neopenis that is situated anatomically in a natal penis position and that is suitable for penetrative intercourse.

A neophallus implant, a neophallus implant system, and a method of implanting a penile prosthetic in a neophallus are disclosed to provide a person who is assigned the female sex at birth with a natal male appearance that conforms with their male gender identity and allows for penetrative intercourse.

Devices, penile implant systems, and methods of implanting the devices and the penile implants are disclosed to construct a neopenis for a natal male who has suffered a traumatic injury to his penis.

A neophallus implant, a neophallus implant system, and a method of implanting a penile prosthetic in a neophallus are disclosed to construct a neopenis for a natal male who has suffered a traumatic injury to his penis.

Penile implants for the natal male penis are generally linear and sized for insertion linearly from the existing crus penis recess through the corpora cavernosum. The corpora cavernosa, the crus penis, and the tunica of the natal male penis provide support and resist bending of the implanted penile implant.

A trans-male pelvis is a pelvis of a person who was assigned the female sex at birth that has been surgically modified to receive a neophallus or a neopenis. The trans-male anatomy does not have corpora cavernosa, the crus penis, or the tunica. Thus, the penile implants for the natal male are not well suited for implantation into the pelvis of the trans-male. One consequence of this anatomical reality for the trans-male pelvis is that a penile implant designed for the natal male will not have adequate support to allow for penetrative intercourse after implantation into the trans-male. Some approaches have been to simply attach a penile implant designed for the natal male directly to the anterior pelvis, which results in a neopenis that is in an anatomically non-natural position (e.g., placed too far cephalad, resulting in a neopenis that is undesirably "too high up"). Embodiments provide supports, implants, devices, systems, and methods that allow the implantation of a penile implant into a trans-male pelvis in an anatomical natal male orientation to provide a natal male appearance that conforms with a desired male gender identity and to facilitate penetrative intercourse.

Embodiments provide an implant that forms an artificial crus penis that is implantable in a person that was assigned the female sex at birth, where the artificial crus penis is adapted to maintain an implanted penile prosthetic (inflatable or non-inflatable) anatomically in a natal penis position that orients a proximal end of the prosthetic inferior and posterior to the pubic bone. The artificial crus penis provides a foundational support for a penile prosthetic to provide the trans-male person with a neopenis that is situated anatomically in the same position as a natal penis suitable for penetrative intercourse.

In embodiments, implantable apparatuses and method of implanting the apparatuses are disclosed that provide a person assigned the female sex at birth with a penis.

In one embodiment, an implantable support provides a reinforced foundation for a penile prosthetic that is implanted in natal female anatomy. The implantable support provides the natal female anatomy with a supporting, suspensory ligament structure that approximates the ligament present in natal male anatomy. These suspensory ligaments in the natal male originate near the pubic symphysis and attach at the base of the penis. The implantable support replicates the suspensory ligaments in the form of an artificial ligament that provides a more realistic appearance for the neophallus with improved responsiveness/input/feeling during thrusting associated with penetrative intercourse.

Embodiments provide an implant that forms an artificial crus penis that is implantable in a male having a penis injury, where the artificial crus penis is adapted to maintain an implanted penile prosthetic in an anatomically proper position for a natal male that orients a proximal end of the prosthetic inferior and posterior to the pubic bone. The artificial crus penis provides a foundational support for a penile prosthetic to provide the male with a neopenis that is situated anatomically in the same position as an uninjured natal penis suitable for penetrative intercourse.

One embodiment of a neophallus implant includes a distal portion that is adapted for insertion into tissue of a neophallus to provide the neophallus with an erection adapted for penetrative intercourse; a first proximal portion and a separate second proximal portion; and a transfer joint. The transfer joint has a distal end connected to the distal portion of the neophallus implant, a first proximal end connected to the first proximal portion of the neophallus implant, a second proximal end connected to the separate second proximal portion of the neophallus implant, with a body of the transfer joint extending between the distal end, the first proximal end, and the second proximal end. The body of the transfer joint has a fixed bend that is adapted to orient the first proximal portion and the separate second proximal portion alongside a descending pubic ramus on either side of a pubic arch of a trans-male pelvis. One effect of the fixed bend is to limit motion and constrain movement of the neophallus implant after implantation.

An embodiment of the neophallus implant provides at least the distal portion of the neophallus implant is an inflatable penile prosthetic, one effect of which is to provide the person with an erection, where the person can control the hardness and the girth of the erection through an amount of liquid inflated into the distal portion.

An embodiment of the neophallus implant provides a liquid port connected to one of the first proximal portion and the second proximal portion, one effect of which is to reduce the number of inflation ports from two down to one.

An embodiment of the neophallus implant the distal portion of the neophallus implant as an inflatable penile prosthetic and the first proximal portion and the second proximal portion of the neophallus implant are not inflatable. The effect is to provide improved comfort where the proximal portions engage with the ramus.

An embodiment of the neophallus implant provides the distal portion of the neophallus implant is an inflatable penile prosthetic having one and only one inflatable cavity, the effect of which is to provide a wide girth implant adapted for insertion into a neophallus that does not have tunicae.

An embodiment of the neophallus implant provides a diameter of the distal portion of the neophallus implant is larger than a diameter of the first proximal portion and a diameter of the second proximal portion. The effect of the smaller diameter proximal portions is to enhance comfort after implantation while the distal portion provides enhanced girth.

An embodiment of the neophallus implant provides the distal portion as an inflatable penile prosthetic having a first inflatable cavity coupled along a septum to a second inflatable cavity. The effect is to have a wider distal portion with two sections that are attached/integrated as one part.

An embodiment of the neophallus implant the neophallus implant as a monolithically formed single unit including the transfer joint, the distal portion, the first proximal portion of the neophallus implant, and the second proximal portion of the neophallus implant. The effect is to provide a Y-shaped neophallus implant that has limited movement and resist axial thrust forces associated with penetrative intercourse.

An embodiment of the neophallus implant provides the fixed bend in the transfer joint to orient the first proximal portion of the neophallus implant at an angle in a range from 80-110 degrees relative to the second proximal portion of the neophallus implant to adapt the first proximal portion and the second proximal portion of the neophallus implant to align with a female pubic arch. The effect of the angle is to adapt the proximal portions to lie alongside the narrower pubic opening of the female pelvis.

An embodiment of the neophallus implant provides the first proximal portion and the second proximal portion of the neophallus implant have a flat profile with a rectangular cross-sectional shape. The effect of the flat profile is to allow the proximal portions to lie flat and comfortably alongside the descending rami.

An embodiment of the neophallus implant provides the first proximal portion and the second proximal portion are each a solid component having a circular lateral cross-sectional shape that tapers to converge to a proximal end. The effect is to provide proximal ends that are easily inserted between tissue around or near the rami.

An embodiment of the neophallus implant provides the transfer joint, the distal portion, the first proximal portion, and the second proximal portion combine to provide a Y-shaped neophallus implant. The Y-shaped neophallus implant limits and constrains movement of the implanted device, particularly during penetrative intercourse. One embodiment of an implant includes a distal tubular portion that is adapted for insertion into a neophallus and is operable to provide the neophallus with an erection adapted for penetrative intercourse; a first proximal portion that is adapted for attachment to tissue of a descending ramus of a pelvis; and a transfer joint having a distal end connected to the distal tubular portion of the implant, a first proximal end connected to the first proximal portion of the implant, and a body extending continuously from the distal end to the first proximal end. The body of the transfer joint has a fixed bend, one effect of which is to orient the distal tubular portion of the implant at an obtuse angle relative to the first proximal portion of the implant, which provides a trans-male with a neopenis having an orientation of that of a penis of a natal male. Benefits and advantages of the implant include the formation of a neopenis that is adapted for penetrative intercourse; providing a person who is assigned the female sex at birth with a genital appearance that conforms with their male gender identity; and providing a person who was assigned the female sex at birth with a neopenis that is situated anatomically in a natal penis position and that is suitable for penetrative intercourse.

An embodiment of the implant has a second proximal portion that is adapted for attachment to tissue of a second descending ramus of the pelvis, with the second proximal portion of the implant connected to a second proximal end of the transfer joint. The fixed bend in the transfer joint has the effect of orienting the first proximal portion of the implant at an angle of 110 degrees or less relative to the second proximal portion of the implant, and this angle conforms with the generally wider female pubic arch of the trans-male pelvis. In one embodiment, the fixed bend in the transfer joint has the effect of orienting the first proximal portion of the implant at an angle in a range from 80-110 degrees relative to the second proximal portion of the implant, and this angle conforms with the generally wider female pubic arch of the trans-male pelvis.

An embodiment of the implant has the transfer joint monolithically formed to the first proximal portion of the implant and the second proximal portion of the implant, which ensures the desired orientation of the implant and provides rigidity. Monolithically formed means formed as a single piece, a one-and-only-one piece implant formed to include two bifurcated proximal portions and a distal portion.

An embodiment of the implant has the fixed bend in the transfer joint at an angle of between 55-70 degrees relative to the second proximal portion of the implant, one effect of which is to align the first proximal portion and the second proximal portion of the implant with a female pubic arch.

An embodiment of the implant has a liquid port connected to the first proximal portion, and the distal tubular portion is a liquid inflatable prosthetic, one effect of which is to provide the neopenis with a reversible erection. A suitable liquid source, such as a reservoir, and a pump to move the liquid, are connected to the liquid port and implanted in the body of the trans-male.

An embodiment of the implant has the distal tubular portion and the first proximal portion linearly aligned (straight along a one longitudinal axis), one effect of which is to securely fit the distal tubular portion in the neophallus in a natal male position and to securely fit the first proximal portion along the ramus for improved comfort.

An embodiment of the implant provides the distal tubular portion as a malleable prosthetic, one effect of which is to provide the neopenis with a user-reversible erection achieved by bending the implant with a hand.

An embodiment of the implant provides the distal tubular portion as a malleable prosthetic and the first proximal portion is a plastic rod, one effect of which is to provide the neopenis with a comfortable implant and a user-reversible erection.

An embodiment of the implant provides the distal tubular portion as a malleable prosthetic and the first proximal portion is a metal rod, one effect of which is to provide the neopenis with a comfortable implant and a user-reversible erection.

An embodiment of the implant provides the distal tubular portion as a malleable prosthetic and the first proximal portion is also a malleable prosthetic, one effect of which is to provide the neopenis with a comfortable implant and a simple user-reversible erection.

An embodiment of the implant provides the distal tubular portion as an inflatable prosthetic having a first inflatable cavity coupled along a septum to a second inflatable cavity, one effect of which is to increase the girth of the neopenis.

One embodiment of an implant includes a distal tubular portion that is adapted for insertion into tissue a neophallus to provide the neophallus with an erection adapted for penetrative intercourse; a first proximal portion that is adapted for attachment to tissue of a descending ramus of a trans-male pelvis; and a transfer joint having a distal end connected to the distal tubular portion of the implant, a first proximal end connected to the first proximal portion of the implant, and a body extending between the distal end and the first proximal end. The body of the transfer joint having a fixed bend, one effect of which is to adapt and orient the distal tubular portion at a female pubic arch half angle relative to the first proximal portion to so adapt the implant to provide a neopenis having a conformation (location and appearance) of that of a natal male penis.

An embodiment of the implant provides a second proximal portion that is adapted for attachment to tissue of a second descending ramus of the trans-male pelvis, with the second proximal portion of the implant connected to a second proximal end of the transfer joint. The fixed bend in the transfer joint has the effect of maintaining the first proximal portion of the implant at a female pubic arch angle relative to the second proximal portion of the implant to provide a comfortable natal male conformation.

An embodiment of the implant provides a liquid port connected to the first proximal portion, and the distal tubular portion is a liquid inflatable prosthetic, one effect of which is to provide the trans-male with a comfortable and reversible erection.

An embodiment of the implant provides the distal tubular portion and the first proximal portion as linear and aligned to be straight along a longitudinal axis, one effect of which provides an easy implantation approach for the surgeon and a more comfortable implant for the trans-male.

An embodiment of the implant provides the distal tubular portion as a malleable prosthetic, and the first proximal portion is one of a plastic rod, a metal rod, and a malleable prosthetic to provide the trans-male with a comfortable and reversible erection.

An embodiment of the implant provides the distal tubular portion as an inflatable prosthetic having a first inflatable cavity coupled along a septum to a second inflatable cavity, one effect of which is to increase the girth of the neopenis.

One embodiment provides a method of implanting a penile implant, where the method includes providing a neophallus implant having a transfer joint connected between a distal tubular portion and a first proximal portion; forming a neophallus; inserting the distal tubular portion into the neophallus; surgically securing the first proximal portion to tissue of a trans-male pelvis; and configuring the distal tubular portion to provide the neophallus with an erection in a neopenis of the trans-male pelvis.

An embodiment of the method includes surgically securing the first proximal portion to the tissue of the trans-male pelvis by implanting an artificial crus penis recess into the trans-male pelvis.

An embodiment of the method includes aligning a neourethra of the trans-male pelvis with the distal tubular portion inside of the neophallus.

Implantable apparatuses and method of implanting the apparatuses are disclosed that provide a person with a neopenis including a penile prosthetic implanted into a neophallus. The neopenis is situated anatomically in the same position as a natal penis suitable for penetrative intercourse.

Embodiments provide a neophallus implant having a Y-shaped penile prosthetic including: a distal tubular portion that is adapted for insertion into tissue to provide the tissue with an erection adapted for penetrative intercourse; a first proximal portion that is adapted for attachment to a descending ramus of a pelvis; a second proximal portion that is adapted for attachment to a second descending ramus of the pelvis; and a transfer joint having a distal end adapted for attachment to the distal tubular portion of the implant, a first proximal end adapted for attachment to the first proximal portion of the implant, a second proximal end adapted for attachment to the second proximal portion of the implant, and a body extending continuously in a Y-shape from the distal end to the first proximal end and the second proximal end. The Y-shaped penile prosthetic has, along with other features, the effect of having two proximal portions that are attachable to the pelvic rami structure, with a distal portion that has a conformation that orients the external part of the penis on a center line of the trans-male person.

Embodiments provide a penile implant system configured to provide a person with a neopenis, where the penile implant system includes a penile prosthetic having a shaft connected between a distal end portion and a proximal end portion, with the distal end portion sized for implantation into a neophallus of the neopenis; and an implantable support that is attachable to a descending ramus of a pelvis to provide an artificial crus penis recess. The proximal end portion of the penile prosthetic is adapted for placement inside of the artificial crus penis recess. One effect of the implantable support is to locate the neopenis anatomically on a trans-male body in a natal penis location.

In embodiments, the implantable support can include a base and an artificial fundiform suspensory ligament located between the base and the artificial crus penis recess. One effect of the artificial fundiform suspensory ligament is to locate the neopenis anatomically below the pubic bone/pubic symphysis of a trans-male body in a suspended and natal penis location.

Embodiments provide a penile implant system configured to provide a person with a neopenis, where the penile implant system includes a penile prosthetic having a distal end portion that terminates at a distal end and a proximal end portion that terminates at a proximal end, with the penile prosthetic sized for surgical implantation into a neophallus of the neopenis; and an implantable support provided separate from the penile prosthetic. The implantable support includes: a proximal attachment tab connected to the implantable support and configured for attachment to a descending ramus of the person, a distal attachment tab connected to the implantable support and configured for attachment to one of a pubic bone and a pubic symphysis of the person, and an artificial crus penis recess connected to the implantable support at a location between the proximal attachment tab and the distal attachment tab. The artificial crus penis recess sized to receive the proximal end portion of the penile prosthetic. One effect of the implantable support is to locate the neopenis anatomically on a trans-male body in a natal penis location. The implant system can include an artificial ligament connected to the artificial crus penis recess. One effect of the artificial ligament is to locate the neopenis anatomically below the pubic bone of a trans-male body in a suspended and natal penis location.

One embodiment provides a penile implant system configured to provide a person assigned the female sex at birth with a neopenis, where the penile implant system includes a penile prosthetic having a distal end portion that terminates at a distal end and a proximal end portion that terminates at a proximal end, with the penile prosthetic sized for surgical implantation into a neophallus of the person assigned the female sex at birth; and an implantable support provided separate from the penile prosthetic. The implantable support includes: a base that is attachable to a pelvis of the person assigned the female sex at birth, an artificial crus penis recess connected to the base, and an artificial ligament connected to the artificial crus penis recess. One effect of the implantable support is to locate the neopenis anatomically on a trans-male body in a natal penis location. The implant system can include an artificial ligament connected to the artificial crus penis recess. One effect of the artificial ligament is to locate the neopenis anatomically below the pubic bone of a trans-male body in a suspended and natal penis location.

Embodiments provide a penile implant system configured to provide a person assigned the female sex at birth with a neopenis. The penile implant system includes a penile prosthetic having a distal end portion that terminates at a distal end and a proximal end portion that terminates at a proximal end, with the penile prosthetic sized for insertion into a neophallus of the person assigned the female sex at birth; and an implantable support provided separate from the penile prosthetic. The implantable support includes: a base that is attachable to a pelvis of the person assigned the female sex at birth, and an artificial crus penis recess connected to the base. The artificial crus penis recess is sized to receive the proximal end portion and the proximal end of the penile prosthetic. One effect of the implantable support having the artificial crus penis recess is to locate the neopenis anatomically on a trans-male body in a natal penis location.

Embodiments of the penile implant system include an interior of the artificial crus penis recess is formed to be conical and sized to receive a conical proximal end portion of the penile prosthetic, one effect of which is to ensure positive coupling of the penile prosthetic to the trans-male pelvis, and to guide self-centering of the penile prosthetic inside of the recess.

Embodiments of the penile implant system include an artificial ligament secured between the base and the artificial crus penis recess. One effect of the artificial ligament is to locate the neopenis anatomically below the pubic bone of a trans-male body in a suspended and natal penis location.

Embodiments of the penile implant system include an inflatable penile prosthetic including a tubular bladder secured to the proximal end portion of the penile prosthetic, one effect of which is to allow the user to control the firmness and girth of the erection of the neophallus.

Embodiments of the penile implant system include a malleable metal core surrounded by a polymer cover, with the malleable metal core having a column strength adapted to allow penetrative intercourse with the penile implant. The malleable aspect of the embodiment has the effect of providing a firm erection even for those with limited dexterity, and the erection has repeatable and satisfactory characteristics each time.

Embodiments of the penile implant system include an implant bed having a tubular sleeve sized to receive the distal end and the proximal end of the penile prosthetic and a flap attached to the tubular sleeve, with the flap extending a first distance in a lateral direction from the tubular sleeve and a second distance in a proximal direction from a proximal end of the sleeve. The tubular sleeve includes an access opening that is sized to allow the penile prosthetic to be inserted into the tubular sleeve. One effect of the tubular sleeve is to offer the surgeon flexibility in locating the implant bed to ensure the desired positioning of the implant.

Embodiments of the penile implant system include a tubular sleeve is formed of a mesh fabric, one effect of which is to ensure tissue ingrowth into the fabric for a positive support after implantation.

Embodiments of the penile implant system include a penile prosthetic that includes a first cylindrical shaft and a second cylindrical shaft, and an implantable support having an implant bed with a first tubular sleeve sized to receive the first cylindrical shaft and a second tubular sleeve sized to receive the second cylindrical shaft. The implant bed includes an access opening that is sized to allow the penile prosthetic to be inserted into the first tubular sleeve and the second tubular sleeve. One effect of the implant bed is to provide an artificial tunica that supports the penile prosthetic and also allows for attachment of the implant to the pelvis.

Embodiments of the penile implant system include a sheet of material, with the base and the artificial crus penis recess integrally formed from the sheet of material to include an artificial ligament connected between the base and the artificial crus penis recess. Effects of the sheet of material, including the artificial ligament, include to allow for ease of implantation, provide effective coupling to the available structure of the pelvis, and provide a structure that is adapted to locate the neopenis anatomically below the pubic bone of a trans-male body in a natal penis location.

Embodiments of the penile implant system include a sheet of material with a first line of stitching demarcating the base and the artificial ligament, and a second line of stitching demarcating the artificial ligament and the artificial crus penis recess. Effects of the stitching include to provide boundaries that identify the artificial ligament and position the artificial ligament in a suspensory orientation useful in the desired anatomical placement of the implant.

Embodiments of the penile implant system include a plug insertable into the artificial crus penis recess. One effect of the plug is to occupy space to prevent tissue from growing into the recess, where the plug is adapted to be removed by the surgeon to expose the recess to receive a portion of the implant.

Embodiments of the penile implant system include a sheet of material, with the base and two of the artificial crus penis recesses integrally formed from the sheet of material, with a first artificial ligament connected between the base and a first one of the two of the artificial crus penis recess and a second artificial ligament connected between the base and a second one of the two of the artificial crus penis recess. Effects of having two artificial crus penis recesses suspended by two artificial ligaments are to achieve the appropriate placement and support of the implant on the pelvis of a trans-male, where the structure is anatomically absent.

Embodiments of the penile implant system include a base of the implantable support having a first flange that is attachable to a first ramus of the pelvis and a second flange that is attachable to a second ramus of the pelvis. The artificial crus penis recess is formed in the base of the implantable support between the first flange and the second flange. One effect of the first flange and the second flange is to provide attachment locations for the implantable support that allows the surgeon to selectively connect the support to the tissue of a trans-male pelvis.

Embodiments of the penile implant system include an artificial crus penis with a receptacle having an opening into a recess, where the recess is defined by an interior surface of the receptacle, and a ridge is formed inside of the receptacle projecting away from the interior surface of the receptacle. When the proximal end of the penile prosthetic is superior to the ridge, the neophallus is in a flaccid state. When the proximal end of the penile prosthetic is inferior to the ridge, the penile prosthetic and the neophallus are maintained in an erect state that adapts the neopenis for penetrative intercourse. One effect of the receptacle, and the ridge inside of the receptacle, is to provide an artificial crus penis with an engagement mechanism that allows the implant to be moved by the user between an erect position in a flaccid position.

Embodiments of the penile implant system include an implantable support with a tab extending from the base. The proximal end of the penile prosthetic is engaged with the tab. When the proximal end of the penile prosthetic is superior to the tab, the neophallus is in a flaccid state. When the proximal end of the penile prosthetic is inferior to the tab, the neophallus is in an erect state adapted for penetrative intercourse. One effect of an implantable support having a projecting tab is to provide the support and engagement mechanism that allows the implant to be moved by the user between an erect position and a flaccid position.

Embodiments of the penile implant system include an implantable support having a fabric having a first lateral edge attachable to a first obturator foramen of the pelvis and a second lateral edge attachable to a second obturator foramen of the pelvis. The artificial crus penis recess is formed in the fabric between the first lateral edge and the second lateral edge. One effect of a fabric support is to provide a support that will integrate with the tissue to provide a strong foundation for penetrative intercourse with the implant.

Embodiments of the penile implant system include a fabric polymer mesh including openings formed in the mesh, with the openings sized to have a mean pore size of about 75 micrometers and so configured for tissue throughgrowth. One effect of selecting a mean pore size of about 75 µm is to ensure tissue growth through the support.

Embodiments of the penile implant system include an implantable support having a plate having a first lateral edge attachable to a first ramus and a second lateral edge attachable to a second ramus, and the artificial crus penis recess includes a post that is formed to project away from the plate. The proximal end of the penile prosthetic includes a post hole that is sized to engage with the post. One effect of the plate is to provide a firm foundational backboard for the implant that is adapted to support the implant and resist the axial forces associated with penetrative intercourse.

Embodiments of the penile implant system include a malleable penile prosthetic having a metal core surrounded by a polymer cover. One effect of the malleable penile prosthetic is to provide an implant that the user can move between an erect position in a flaccid position, where the erection is uniform and repeatable.

Embodiments of the penile implant system include an inflatable penile prosthetic having a bladder that is inflatable with liquid to an erect state having a column strength adapted to allow penetrative intercourse with the prosthetic penis. One effect of the inflatable penile prosthetic is to allow the user to control the firmness and the girth of the erection.

Embodiments provide a method of providing a person with a neopenis by implanting a penile implant in a neophallus of the person. The method includes providing an implant bed including an artificial crus penis recess; securing a proximal portion of the implant bed to a descending ramus of the person; securing a distal portion of the implant bed to one of a pubic bone and a pubic symphysis of the person; locating the artificial crus penis recess inferior relative to the pubic bone of the person; inserting a penile prosthetic into the neophallus; and inserting a proximal end portion of the penile prosthetic into the artificial crus penis recess. One effect of the method is to provide a person that does not have a penis, whether trans-male or through trauma, with a new penis that can achieve an erection.

Embodiments provide a method of providing a person with a neopenis by implanting a penile implant in a neophallus of the person. The method includes implanting an implantable support in the person, attaching the implantable support to a descending ramus of a pelvis of the person, and providing the pelvis with an artificial crus penis formed by the implantable support; implanting a distal end portion of a penile prosthetic into a distal end portion of the neophallus; implanting a proximal end portion of the penile prosthetic into a proximal end portion of the neophallus; and coupling the proximal end portion of the penile prosthetic with the artificial crus penis formed by the implantable support. One effect of the method is to provide a trans-male pelvis with a crus penis recess, where the crus penis recess supports an implant in an anatomical position that is the same as, or nearly the same as, the position of a penis for a natal male.

An embodiment of the method includes locating the neopenis anatomically in a natal penis location, one effect of which is to provide the trans-male with a penis that is appropriately located inferior relative to the pubic bone (not too high up on the pelvis).

An embodiment of the method includes locating at least the proximal end portion of the penile prosthetic in an anatomic position of a proximal end portion of a natal penis, one effect of which is to replicate the location of a natal penis having a crus penis.

Embodiments provide a method of implanting a penile implant in a neophallus of a person assigned the female sex at birth. The method includes providing an implant bed having an artificial crus penis recess; implanting the implant bed in the person assigned the female sex at birth, and locating the artificial crus penis recess proximal from the neophallus and superior relative to a neourethra formed within the neophallus of the person assigned the female sex at birth; inserting a penile prosthetic into the neophallus; and inserting a proximal end portion of the penile prosthetic into the artificial crus penis recess. One effect of the method is to provide a trans-male with a neophallus implant that is adapted to accommodate the axial forces associated with penetrative intercourse.

An embodiment of the method includes attaching a base of the implant bed to bone of a pelvis of the person assigned the female sex at birth and locating the artificial crus penis recess inferior relative to a pubic bone of the pelvis. One effect of locating the artificial crus penis recess inferior relative to the pubic bone is to ensure that the implanted penile prosthetic is not "too high up" on the trans-male pelvis, which is an awkward and undesirable location for a penis.

An embodiment of the method includes attaching a base of the implant bed to bone of a pelvis of the person assigned the female sex at birth and locating the artificial crus penis recess inferior relative to a pubic symphysis of the pelvis, one effect of which is to ensure a durable foundation for the implant that supports penetrative intercourse.

An embodiment of the method includes that a proximal end portion of the penile prosthetic is a conical proximal end portion and the artificial crus penis recess is a conical recess. The method further includes placing the conical proximal end portion of the penile prosthetic into the conical recess of the artificial crus penis recess, one effect of which is to ensure an appropriate location of the implant.

Embodiments provide a method of implanting a penile implant. The method includes forming a neophallus and attaching the neophallus to a person assigned the female sex at birth; providing an implant bed having an artificial crus penis recess; implanting the implant bed in the person assigned the female sex at birth; attaching a proximal portion of the implant bed to a pelvis of the person assigned the female sex at birth and locating the artificial crus penis recess inferior relative to a pubic bone of the pelvis; and inserting a penile prosthetic into the neophallus and inserting a proximal end portion of the penile prosthetic into the artificial crus penis recess. One effect of the method is to provide a person assigned the female sex at birth with a penis.

An embodiment of the method includes locating a distal portion of the implant bed superior relative to a neourethra formed within the neophallus of the person assigned the female sex at birth, one effect of which is to replicate the fundiform ligament of the natal penis of a male.

An embodiment of the method includes locating the artificial crus penis recess posterior relative to a pubic bone of the pelvis, one effect of which is to locate the neophallus implant at an angle in a natal male pelvis location to facilitate penetrative intercourse.

An embodiment of the method includes locating the artificial crus penis recess proximal from the neophallus, one effect of which is to replicate the location of a natal male crus penis in the pelvis of a female that was born without a crus penis.

Embodiments provide a method of implanting a penile implant in a neophallus of a person assigned the female sex at birth. The method includes providing an implant bed having an artificial crus penis recess connected to a base; implanting the implant bed in the person assigned the female sex at birth by securing the base of the implant bed to a ramus and locating the artificial crus penis recess inferior a pubic bone of the person assigned the female sex at birth; inserting a penile prosthetic into the neophallus; and inserting a proximal end portion of the penile prosthetic into the artificial crus penis recess. One effect of the method is to provide a female pelvis with a newly formed penis.

One exemplary method of surgically creating a neopenis includes dissecting tissue away from a vagina to disconnect the vagina from organs and connective tissue inside of a pelvis; inverting the vagina out of the pelvis to provide an inverted vagina by exposing an interior wall of the vagina outside of the pelvis; inserting a penile prosthetic into the inverted vagina and inside a portion of the pelvis; and supporting a proximal portion of the penile prosthetic by attaching the proximal portion of the penile prosthetic to the pelvis.

The method can include inserting a bulking material and the penile prosthetic into the inverted vagina.

The method can include removing a cervix by dissecting the cervix away from the vagina.

The method can include removing tissue from a cervix and forming a glans penis with the tissue removed from the cervix; and attaching the glans penis to the inverted vagina.

The method can include folding a superior portion of tissue of the inverted vagina and closing the superior portion of tissue of the inverted vagina to a second portion of the inverted vagina thus forming a channel; and placing a portion of a urethra of the trans-male and a portion of a neourethra of the trans-male into the channel.

The method can include inserting a malleable and non-inflatable penile prosthetic into the inverted vagina and inside the portion of the pelvis; and attaching a proximal portion of the malleable and non-inflatable penile prosthetic to a descending ramus of the pelvis.

The method can include inserting an inflatable penile prosthetic into the inverted vagina and inside the portion of the pelvis; attaching a proximal portion of the inflatable penile prosthetic to a descending ramus of the pelvis; coupling a reservoir and a pump to the inflatable penile prosthetic with tubing; and implanting the reservoir and the pump into the trans-male.

One embodiment provides a method of implanting a penile implant. The method includes providing a neophallus implant having a transfer joint connected between a distal portion and a first proximal portion, with the transfer joint having an angle that maintains the distal portion off of a longitudinal axis of the first proximal portion; forming a neophallus; inserting the distal portion into the neophallus and forming a neopenis; and securing the first proximal portion of the neophallus implant between muscle attached to a ramus of a trans-male pelvis and tissue.

An embodiment of the method includes implanting a pump and a reservoir; coupling the pump and the reservoir to the distal portion of the neophallus implant; and inflating the distal portion of the neophallus implant to provide the neopenis with an erection.

An embodiment of the method includes forming a tissue pocket alongside of the ramus and securing the first proximal portion of the neophallus implant in the tissue pocket between the muscle attached to the ramus of the trans-male pelvis and subcutaneous tissue.

One embodiment provides a method of implanting a penile prosthetic in a neophallus. The method includes providing a neophallus implant having a transfer joint connected to an inflatable distal portion, a first proximal portion, and a second proximal portion such that the neophallus implant is a Y-shaped inflatable implant; forming a neophallus; inserting the inflatable distal portion into the neophallus; retaining the first proximal portion of Y-shaped inflatable implant between muscle attached to a first ramus of a trans-male pelvis and first tissue superior to the muscle; retaining the second proximal portion of Y-shaped inflatable implant between muscle attached to a second ramus of the trans-male pelvis and second tissue superior to the muscle; and engaging a fixed bend in the transfer joint with the at least one of the first tissue and the second tissue and constraining movement of the Y-shaped inflatable implant.

An embodiment of the method includes forming a first tissue pocket between the muscle attached to the first ramus of the trans-male pelvis and the first tissue superior to the muscle; and forming a second tissue pocket between the muscle attached to the second ramus of the trans-male pelvis and the second tissue superior to the muscle.

An embodiment of the method includes maintaining an opening of the first tissue pocket and maintaining an opening of the second tissue pocket by inserting a place holder into each of the first tissue pocket and the second tissue pocket.

An embodiment of the method includes providing the neophallus implant with a flat first proximal portion and a flat second proximal portion; placing the flat first proximal portion over the muscle attached to the first ramus; and placing the flat second proximal portion over the muscle attached to the second ramus.

An embodiment of the method includes forming the fixed bend in the transfer joint at a pubic arch angle to align the first proximal portion of Y-shaped inflatable implant and the second proximal portion of Y-shaped inflatable implant with a pubic arch of the trans-male pelvis.

One embodiment provides a method of surgically creating a neopenis on a trans-male. The method includes dissecting tissue away from at least an apex of a vagina to disconnect the vagina from organs and connective tissue inside of a pelvis; inverting the vagina out of the pelvis to provide an inverted vagina by exposing an interior wall of the vagina outside of the pelvis; inserting a penile prosthetic into the inverted vagina and inside a portion of the pelvis; and supporting a proximal portion of the penile prosthetic by securing the proximal portion of the penile prosthetic to tissue of the pelvis.

An embodiment of the method includes attaching an artificial crus penis recess to the tissue of the pelvis, and supporting the proximal portion of the penile prosthetic by inserting the proximal portion of the penile prosthetic into the artificial crus penis recess.

An embodiment of the method includes forming a tissue pocket alongside of each descending ramus of the pelvis, and supporting the proximal portion of the penile prosthetic by inserting the proximal portion of the penile prosthetic into the tissue pocket.

An embodiment of the method includes inserting a bulking material and the penile prosthetic into the inverted vagina.

An embodiment of the method includes removing a cervix by dissecting the cervix away from the vagina.

An embodiment of the method includes removing tissue from a cervix and forming a glans penis with the tissue removed from the cervix; and attaching the glans penis to the inverted vagina.

An embodiment of the method includes forming a glans penis at a distal end of the neopenis with tissue of a cervix.

An embodiment of the method folding an inferior portion of tissue of the inverted vagina and closing the inferior portion of tissue of the inverted vagina to a second portion of the inverted vagina thus forming a channel; and placing one of a portion of a urethra of the trans-male and a portion of a neourethra of the trans-male into the channel.

An embodiment of the method includes inserting a malleable and non-inflatable penile prosthetic into the inverted vagina and inside the portion of the pelvis; and attaching a proximal portion of the malleable and non-inflatable penile prosthetic to a descending ramus of the pelvis.

An embodiment of the method includes inserting an inflatable penile prosthetic into the inverted vagina and inside the portion of the pelvis; attaching a proximal portion of the inflatable penile prosthetic to a descending ramus of the pelvis; coupling a reservoir and a pump to the inflatable penile prosthetic with tubing; and implanting the reservoir and the pump into the trans-male.

BRIEF DESCRIPTION OF THE DRAWINGS

The accompanying drawings are included to provide a further understanding of embodiments and are incorporated in and are a part of this specification. The drawings illustrate embodiments and together with the description explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

FIG. 11A is a perspective view of one embodiment of an implantable support.

FIG. 11B is a perspective view of the implantable support illustrated in FIG. 11A secured to a trans-male pelvis.

FIG. 12 is a perspective view of one embodiment of an implantable support including a base and an artificial crus penis recess connected to the base.

FIG. 13A is a top view, FIG. 13B is a perspective view, and FIG. 13C is an end view of one embodiment of the artificial crus penis recess of the implantable support illustrated in FIG. 12.

FIG. 17 is a schematic view of the implantable support illustrated in FIG. 12 is attached to a trans-male pelvis.

FIG. 20B is a schematic view of the alternative implantable support illustrated in FIG. 19B affixed relative to a trans-male pelvis.

FIG. 21 is a schematic view of one embodiment of an implantable support oriented relative to a trans-male pelvis.

FIG. 22 is a top view of the implantable support illustrated in FIG. 21.

FIG. 24B is a schematic view of the implantable support illustrated in FIG. 24A with the ramus straps affixed to the pelvis.

FIG. 51A is a perspective view of one embodiment of a neophallus implant.

FIG. 51B is a perspective view of one embodiment of a spine of the neophallus implant of FIG. 51A.

FIG. 51C is a cross-sectional view of the neophallus implant of FIG. 51A.

DETAILED DESCRIPTION

Figure 1A:
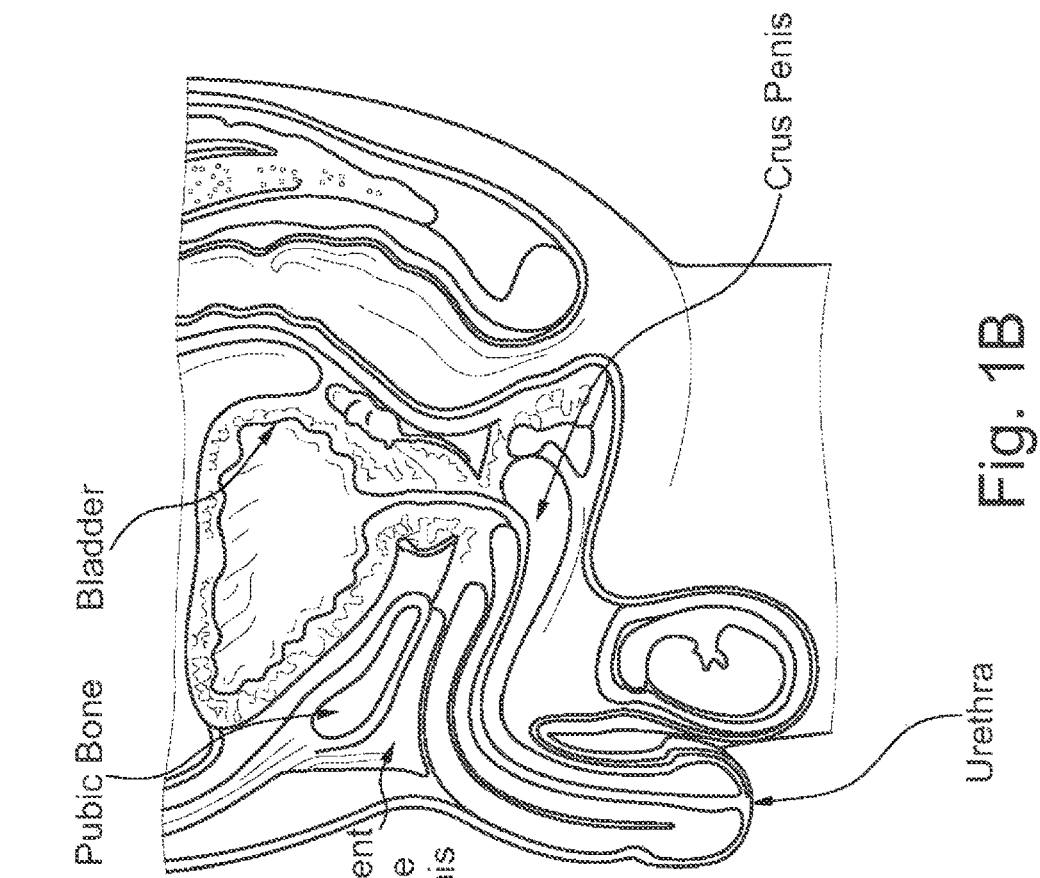
FIG. 1A is an illustration of a natal female pelvis.

The drawings illustrate embodiments and together with this written description explain principles and advantages of embodiments.

The features of the various exemplary embodiments described in this application may be combined with each other, unless specifically noted otherwise.

Anterior means situated toward a front of the body.

Cis-male is a person assigned the male sex at birth.

Cis-female is a person assigned the female sex at birth.

Inferior means situated below, closer to the feet than another similar part of an upright body.

Posterior means situated toward the rear of the body.

Superior means situated toward the head and further away from the feet than another similar part of an upright body.

Anatomically affirming means one or more anatomical features that align with a person's gender identity.

The phrase "situated anatomically in a natal penis position" means a neopenis surgically attached to a trans-male pelvis that is situated anatomically in the same or similar position as a natal penis of a natal male pelvis and is suitable for penetrative intercourse.

Gender identity is a person's internal sense of being male, female, or other.

Gender affirming surgery is a surgical procedure to provide a person's body with genitalia that aligns with their gender identity.

Glansplasty is a surgical procedure to construct a glans penis on a distal end of a surgically constructed neophallus to provide a patient with an enlarged glans penis. The glans penis is the sensitive and bulbous structure at the tip of the penis and is anatomically homologous to the clitoral glans.

Metoidioplasty is a word that translates to "a surgical change toward the male." Metoidioplasty is generally carried out in two stages, testosterone treatment followed by surgery. During the testosterone treatment, the clitoris responds by growing longer. During surgery, the surgeon severs the ligament that holds the clitoris in place under the pubic bone, resulting in "clitoral release" that allows the enlarged clitoris to have the appearance of a small penis.

Natal female means a person who is born with all or a substantial portion of female genitalia.

Natal male means a person who is born with all or a substantial portion of male genitalia.

Neopenis means a newly constructed penis, where the neopenis includes a neophallus and a prosthetic inserted into the neophallus.

Neophallus means a newly constructed shaft of skin in the shape of a penis, where the neophallus is formed from tissue donated from a thigh or a forearm or other site of that person.

Neoscrotum means a newly formed scrotum, where the newly formed scrotum may be formed from tissue harvested from a donor site or from a local site such as the labia majora.

Phalloplasty means the surgical construction of the neophallus, and applies to both cis-male and cis-female. Female-to-Male phalloplasty is the construction of a penile shaft on a person assigned the female sex at birth to allow their outward genital appearance to conform to their gender. The surgeon may choose to form the phalloplasty in conjunction with metoidioplasty.

Pubic bone means the boney portion of the pelvis that is lateral to the pubic symphysis.

Scrotoplasty is a surgical procedure in which the labia of the vagina are surgically stretched and joined through suturing to form a neoscrotum.

Sex is the classification of a person as male or female based upon the appearance of their external anatomy at birth. While sex is classified at birth based upon the visual aspect of the genitals, sex is in fact a combination of chromosomes, hormones, internal reproductive organs, and external organs.

Transgender means a person whose gender identity differs from the sex they were assigned at birth.

Trans-male pelvis means a pelvis of a person who was assigned the female sex at birth that has been surgically modified to receive a neophallus or a neopenis.

Vaginectomy is a surgical procedure to remove all or part of the vagina.

Female-to-Male (FTM) phalloplasty is an extensive surgical procedure. The FTM phalloplasty is typically completed in stages. In one approach, the FTM phalloplasty is completed in three stages, including a first stage to perform the metoidioplasty and form a neophallus; a second stage including vaginectomy; and a third stage to place a penile prosthetic into the neophallus.

Formation of the neophallus includes a procedure to harvest tissue from a donor site on the patient to form the tubular body of the neophallus and a separate step of harvesting tissue to form a neourethra. In one suitable approach, a surgeon harvests tissue for the neophallus from the radial forearm in a procedure referred to as a radial forearm free-flap phalloplasty. It is desirable to harvest tissue from a donor site without hair follicles when forming the neourethra as the follicles have the potential to accumulate deposits from the urine and form a blockage. The interior portion of the radial forearm provides one possible location for the harvesting of tissue suitable for forming the neourethra. The neophallus is surgically attached to a location that is superior to the location of the natal urethra, since the natal female urethra is inferior relative to the bladder and the pubic bone. The surgeon may choose to begin expanding the labia in a first step of the scrotoplasty. It is desirable to allow the neophallus and the neourethra to heal for a period between 4-6 months before moving to the second stage of the FTM phalloplasty.

The second stage of the FTM phalloplasty is a time-consuming surgical procedure that includes the vaginectomy, which may be combined with laparoscopic hysterectomy and joining of the natal urethra with the neourethra. After joining the natal urethra with the neourethra the surgeon will perform glansplasty and any of the remaining steps of the scrotoplasty, for example placing testicular prostheses inside of the newly formed scrotum. The surgeon may choose to transport the clitoris to the base of the neophallus. It is desirable to allow the second stage to heal for a period between 4-6 months before moving to the third stage of the FTM phalloplasty.

The third stage of the FTM phalloplasty includes placement of a penile prosthetic inside of the neophallus. The penile prosthetic allows the neophallus to achieve an erection. The erect neophallus will not be well suited for penetrative intercourse unless the surgeon provides the neophallus with some form of a foundation that will support column-loading forces.

Some surgeons will attach a portion of an implant for a neopenis to the pubic bone, for example with screws, to obtain an amount of foundational support of the neopenis. However, attachment of the neopenis to the pubic bone of the trans-male pelvis will not result in a neopenis that is situated anatomically in a natal penis position. A natal male penis has an external portion and an internal portion called the crus penis. The external portion of the penis accounts for about two-thirds of the penis length, with the crus penis accounting for the remaining one-third of the length. Crus means leg. The crus (crura for plural) penis is the proximal portion of each of the corpus cavernosum of the male penis. The crus penis in a male is secured to the pelvis in which each of the proximal crura of the penis diverges away from the midline in the proximal direction and is attached to the ischiopubic ramus. The diverging and posterior portion of each crus penis is thus inferior relative to the pubic bone (since each is attached to the descending ischiopubic ramus), such that the natal male penis is in fact attached within the body inferior and posterior to the pubic bone (See FIG. 1B).

It is desirable to provide a person who was assigned the female sex at birth with a neopenis that is situated anatomically in a natal penis position and that is suitable for penetrative intercourse.

Figure 1B:
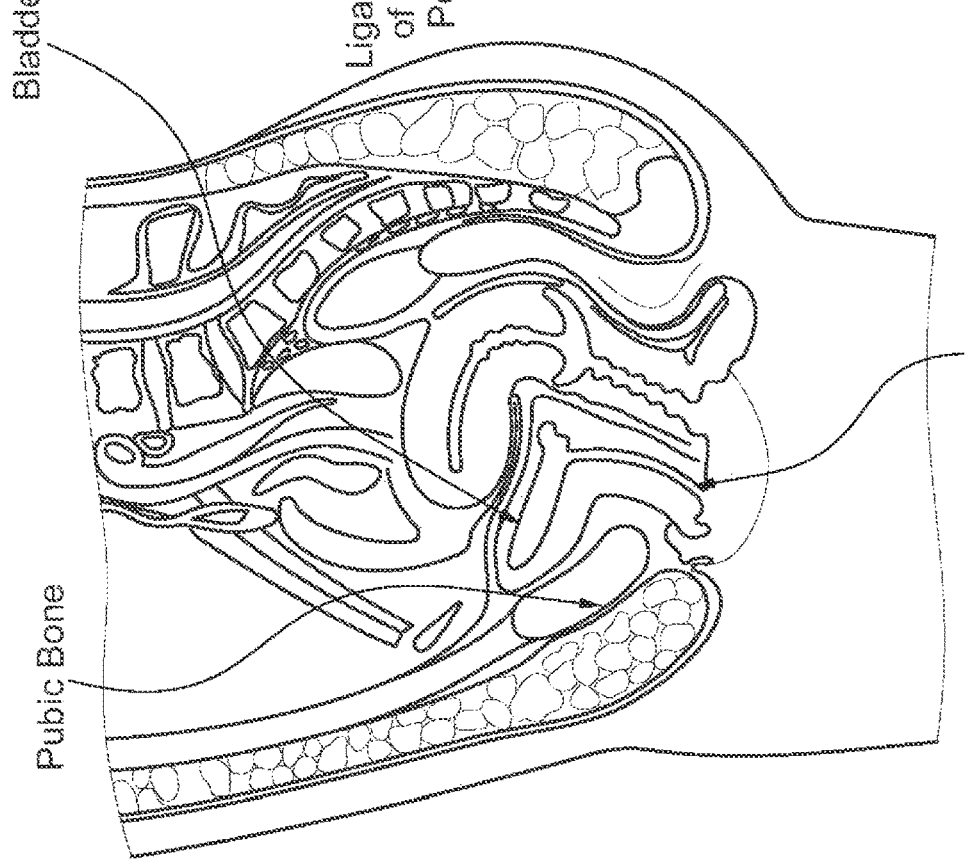
FIG. 1B is an illustration of a natal male pelvis.

FIG. 1A is an illustration of a female pelvis and FIG. 1B is an illustration of a male pelvis.

The anatomy of the female pelvis locates the bladder posterior of the pubic bone, with the urethra descending to a location both posterior and inferior of the pubic bone. The anatomy of the male pelvis locates the bladder posterior of the pubic bone, with the external penis inferior to the pubic bone and the crus penis both inferior and posterior to the pubic bone. The male urethra is longer than the female urethra, and includes a vertical portion descending from the bladder and a second portion that extends through the external penis. A proximal portion of the penis is suspended by the fundiform ligament of the penis that is connected between a portion of the pubic bone and a base of the penis.

Figure 1C:
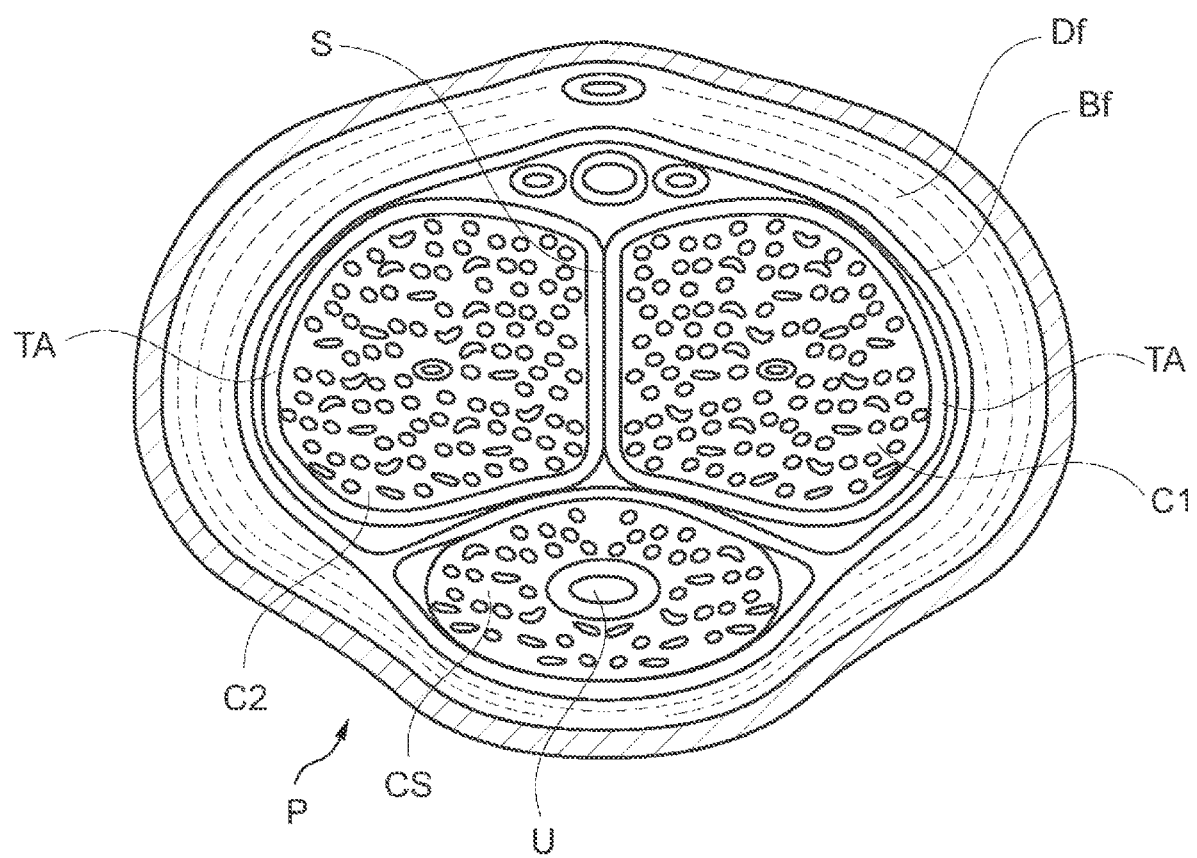
FIG. 1C is a cross-sectional view of a natal male penis.

FIG. 1C is a cross-sectional view of a natal male penis. The natal male penis includes a pair of corpora cavernosa C1 and C2, each surrounded by a tunicae albuginea TA (referred to as a tunica). The tunica TA constrains the corpus spongiosum CS tissue and contributes to the rigidity of the shaft of the penis when erect. Each tunica TA for each of the corpora cavernosa C1 and C2 meets along a longitudinal plane at a septum S of the penis. The urethra U is separate from the corpora cavernosa C1 and C2. The Buck's fascia Bf surrounds each tunica TA, and the Darto's fascia surrounds the Buck's fascia. The trans-male does not have a penis, and the surgically created neophallus lacks the supporting tunica TA structure and the erectile tissue of the corpora cavernosa C1 and C2. The embodiments described in this application provide the trans-male with supporting structure that allows the neopenis of the trans-male to have an erection that is located in a natal male position and with sufficient column strength to have penetrative intercourse.

Some FTM phalloplasty procedures locate a penile prosthetic within skin of a neophallus with a proximal portion of the prosthetic attached to the female pubic bone. The penile prosthetic is connected to the pubic bone, for example with bone screws. However, attachment of the penile prosthetic to the pubic bone will orient the neophallus parallel to the pubic body lateral of the pubic symphysis, which can potentially result in the neophallus being in an elevated positon that is anatomically "too high up," (see FIG. 1B). Thus, attachment of the penile prosthetic to the pubic bone will not provide the trans-male with a neophallus that is situated anatomically in the same position as a penis of a natal male penis, which is evident when the anatomy of the female pelvis (FIG. 1A) is compared to the anatomy of the male pelvis (FIG. 1B). Other FTM phalloplasty procedures insert an available natal male penile prosthetic into the skin of a neophallus, with a proximal portion of the natal male penile prosthetic secured to the pubic body lateral of the pubic symphysis. This location of the natal male penile prosthetic in a trans-male results in the neopenis having a steep angle and a non-natal location that is elevated too high relative to the urogenital organs.

Figure 2A:
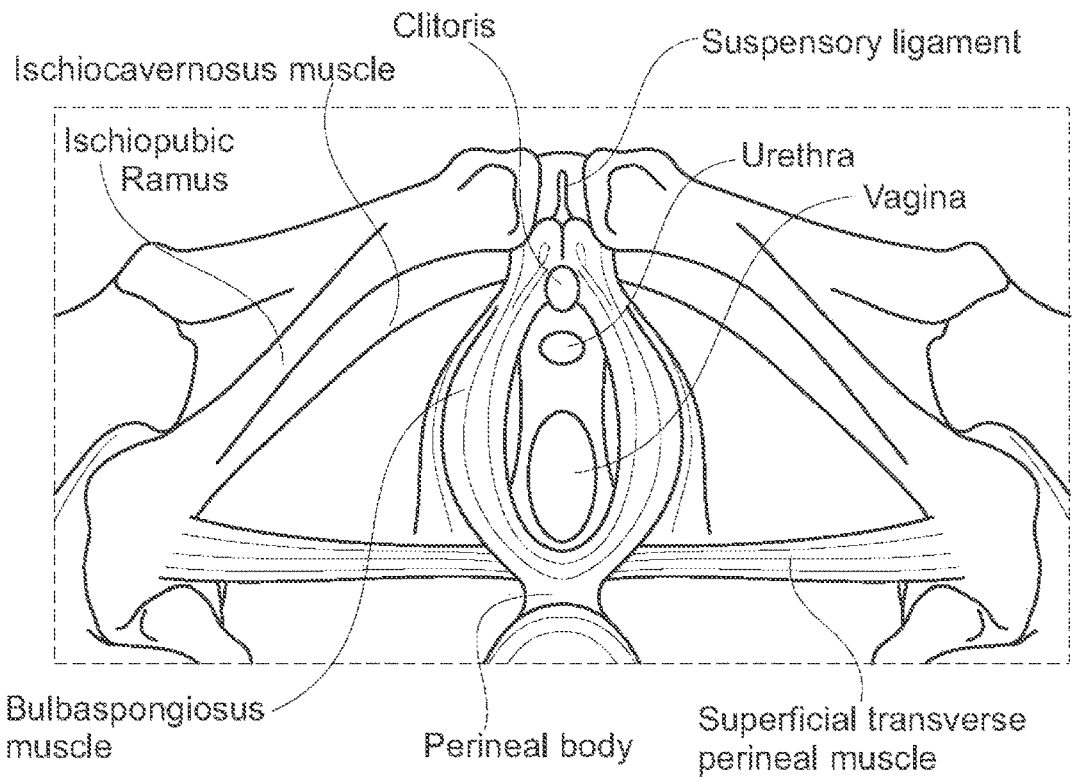
FIG. 2A is an inferior view of a natal female pelvis and FIG. 2B is an inferior view of a trans-male pelvis including a penile prosthetic and an implantable support.
Figure 2B:
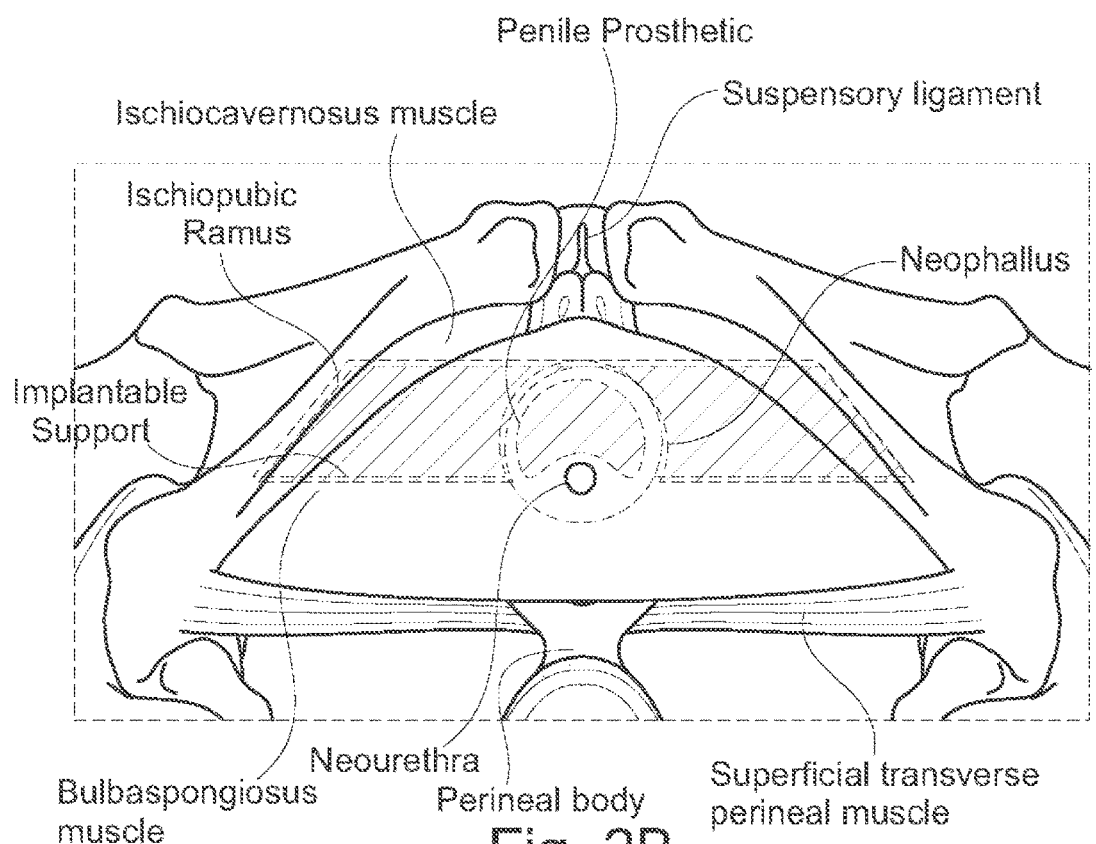

FIG. 2A is an inferior view of a female pelvis and FIG. 2B is an inferior view of a trans-male pelvis including a penile prosthetic and an implantable support.

With reference to FIG. 2A, the female pelvis includes the urethra located between the clitoris and the vagina. The clitoris is the analog to the glans penis and the FTM phalloplasty procedure includes metoidioplasty using hormones to lengthen the clitoris prior to releasing the clitoris from its suspensory ligament. During some procedures, the clitoris is transposed to the base of the neophallus.

The first stage of the FTM phalloplasty procedure also includes lengthening of the urethra concurrent with formation of the neophallus. The lengthened neourethra and the neophallus are both formed with tissue harvested from the radial forearm in a procedure referred to as radial forearm freeflap. In other approaches, the neophallus is formed with tissue harvested from the anterior thigh. The radial forearm freeflap procedure is the more common approach.

The second stage of the FTM phalloplasty procedure can be combined with laparoscopic hysterectomy and includes a joining of the lengthened neourethra to the natal urethra, vaginectomy, glansplasty at the distal neophallus, placement of testicular prosthetics, and transposition of the clitoris to the base of the neophallus. In one embodiment of the advances described in this application, a place saver is implanted into the neophallus to maintain an opening in the neophallus that is sized to subsequently receive the penile prosthetic. The place saver is an oblong balloon that is inflated inside of the cavity formed in the neophallus. In one embodiment, a port is provided on an end of the oblong balloon to allow the balloon to be filled with a gas, such as air, or a liquid, such as saline. The oblong balloon includes a groove formed as a longitudinal trough that is sized and adapted to receive the neourethra.

The body is given sufficient time, for example several weeks or months, to heal between both the stage one and stage two procedures.

The third stage of the FTM phalloplasty procedure includes implanting a penile prosthetic inside of the neophallus to provide for an erection of the neophallus in the trans-male.

FIG. 2B is an inferior view of the pelvis of a trans-male showing a schematic representation of one penile implant system configured to provide a person assigned the female sex at birth with a neopenis. One embodiment of the penile implant system includes a penile prosthetic located inside of a neophallus and an implantable support that provides a foundation for the penile prosthetic. The implantable support allows for a desired anatomical positioning of the neophallus and provides a foundation that allows for penetrative intercourse.

The implantable support is provided separate from the penile prosthetic prior to implantation and includes a base that is attachable to bone of the pelvis and an artificial crus penis recess. The artificial crus penis recess is sized to receive the proximal end of the penile prosthetic.

Figure 3:
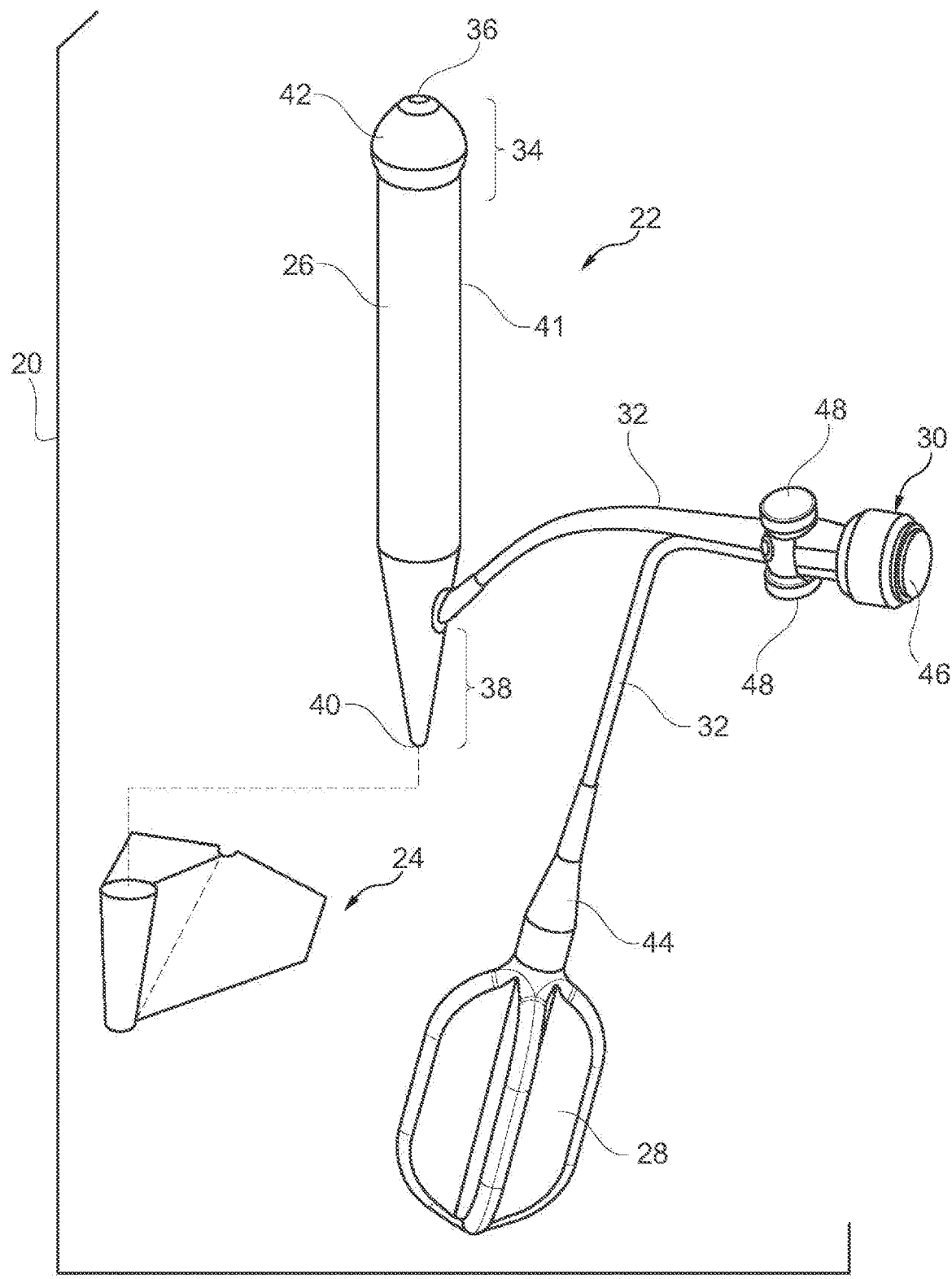
FIG. 3 is a perspective view of one embodiment of a neophallus implant system including a penile prosthetic and an implantable support.

FIG. 3 is a perspective view of one embodiment of a neophallus implant system 20 including a prosthesis 22 and an implantable support 24.

In one embodiment, the prosthesis 22 is an inflatable penile prosthetic and includes a penile prosthetic 26, a reservoir 28, and a pump 30 connected to the penile prosthetic 26 and the reservoir 28, for example by kink resistant tubing 32. In one embodiment, the prosthesis 22 is a rigid rod-style of prosthetic that is referred to as an implantable malleable penile prosthetic. An implanted malleable penile prosthetic is positioned manually to transition a penis between an erect state and a curved, flaccid state. An implanted malleable penile prosthetic includes a malleable metal core surrounded by a polymer cover, with the malleable metal core having a column strength adapted to allow penetrative intercourse with the penile implant.

The penile prosthetic 26 includes a distal end portion 34 that terminates at a distal end 36 and a proximal end portion 38 that terminates at a proximal end 40, with a shaft 41 extending between the distal end portion 34 and the proximal end portion 38. In one embodiment, the distal end portion 34 includes a glans-shaped bulb 42 suitable for providing the neophallus with a glans penis. In one embodiment, the distal end portion 34 includes a skirt that extends away from the shaft 41 to provide the distal portion of the prosthetic with an umbrella-shape or a mushroom shape that is adapted to prevent the shaft 41 from migrating out of the distal end of the neophallus. The penile prosthetic 26 is insertable into a neophallus of a trans-male who was assigned the female sex at birth. The neophallus of the trans-male lacks a tunica and the corpus cavernosum inside of the tunica. The penis of a natal male includes two corpora cavernosa inside of a tunica pair. An implant for a natal male will include two penile prosthetics, one for each corpus cavernosum. In contrast, a single inflatable unit is suitable for implantation in the tissue of the neophallus of a trans-male since the neophallus does not have a pair of corpora cavernosa to receive a pair of inflatable implants. Suitable material for fabricating the penile prosthetic 26 includes silicone, biocompatible polymers such as urethanes, and blends of polymers with urethane, copolymers of urethane, or the like. One suitable penile prosthetic is available from Coloplast Corp., Minneapolis, Minn.

The reservoir 28 is sized to maintain a volume of liquid between about 50-300 ml and includes a neck 44 that is smoothly coupled with the kink resistant tubing 32. In one embodiment, the reservoir 28 is provided as a "cloverleaf" style of reservoir having multiple leaves that may be folded one against the other to compact the reservoir 28 for implantation into the abdomen of the user, ectopically under the skin and anterior of the rectus sheath, in the space that was formerly the vaginal vault, or in the space of Retzius depending upon the procedure and the preference of the surgeon. One suitable reservoir 28 is sized to retain approximately 130 mL of liquid and is available from Coloplast Corp., Minneapolis, Minn.

The pump 30 includes a pump bulb 46 integrated with the deflation pads 48 and operates to move liquid from the reservoir 28 through the tubing 32 and into the penile prosthetic 26. The deflation pads 48 operate to open a flow path to allow the liquid in the penile prosthetic 26 to drain through the tubing 32 back to the reservoir 28. The pump is adapted to be implanted into a neoscrotum, which can be formed by surgically stretching the labia of the vagina to a size that is suitable for receiving the pump 30. One suitable pump is available from Coloplast Corp., Minneapolis, Minn. The pump 30 is as described in U.S. Pat. Appln. Pub. 2007/0142700, which issued as U.S. Pat. No. 8,167,788, the disclosure of which is incorporated by reference in its entirety into this application.

The reservoir 28, the pump 30, and the tubing 32 are as described in U.S. Pat. Appln. Pub. 2011/0118540, which issued as U.S. Pat. No. 8,337,392, the disclosure of which is incorporated by reference in its entirety into this application.

Figure 4:
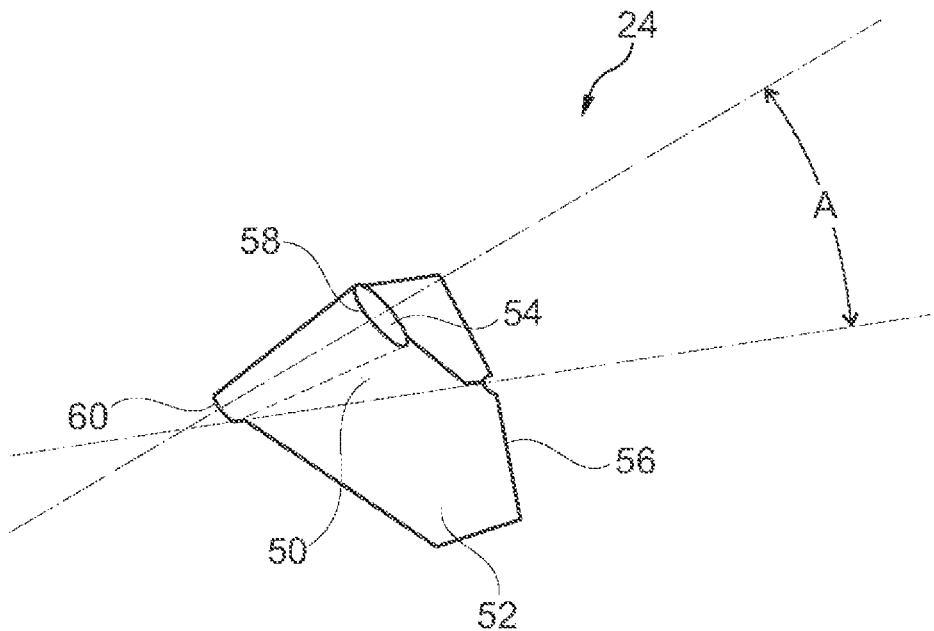
FIG. 4 is a perspective view of one embodiment of an implantable support.
Figure 5:
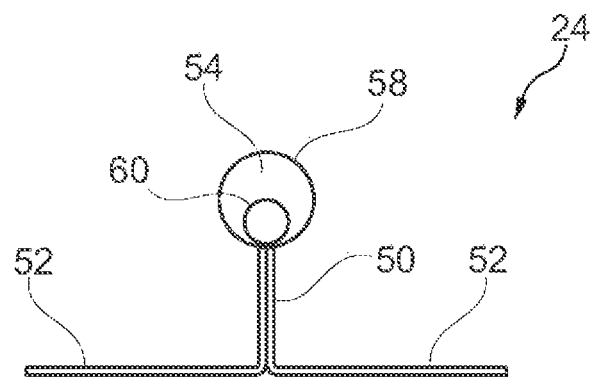
FIG. 5 is a front view of the implantable support illustrated in FIG. 4.

FIG. 4 is a perspective view and FIG. 5 is a right side view of the implantable support 24. In one embodiment, the implantable support 24 includes an artificial ligament 50 connected between a base 52 and an artificial crus penis recess 54. The base 52 forms an implant bed that is attachable to the pelvis, and the artificial crus penis recess 54 is sized to receive the proximal end portion 38 of the penile prosthetic 26 (FIG. 3). The artificial ligament 50 is a connecting structure located between the base 52 and the artificial crus penis recess 54 that is analogous to the ligament of the penis (FIG. 1B), which is also referred to as the fundiform suspensory ligament in the natal male. In one embodiment, the artificial ligament 50 is triangular in shape having a hypotenuse that intersects the base 52, a first leg that intersects with an exterior portion of the artificial crus penis recess 54, and a second leg that extends from the base 52 to the artificial crus penis recess 54. The second leg of the triangular portion of the artificial ligament 50 allows the proximal portion of the penile prosthetic to descend a distance away from the pubic bone to locate the implanted penile prosthetic anatomically in a location of the male penis in a natal male. The artificial ligament 50 provides the means for supporting an implanted penile prosthetic in a trans-male in an orientation of that of the penis of a natal male. The artificial ligament 50, in combination with the artificial crus penis recess 54, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

In one embodiment, the artificial crus penis recess 54 is conical in shape and tapers from a distal end 58 to a proximal end 60 in a manner that is sized to receive the proximal end portion 38 of the penile prosthetic 26. In other embodiments, the artificial crus penis recess 54 includes a closed base and is cup-shaped. The artificial crus penis recess 54 has a recess depth in a range from 0.5-7 cm, and preferably the recess depth for the artificial crus penis recess is between 1-4 cm. The artificial crus penis recess 54 is adapted to receive the proximal end portion of either an inflatable penile prosthetic or a non-inflatable penile prosthetic (e.g., a malleable prosthetic).

The axis of the artificial crus penis recess 54 is not parallel with the base 52. In one embodiment, the artificial crus penis recess 54 is oriented at an acute angle A relative to the base 52, which is to say that the artificial ligament 50 maintains the artificial crus penis recess 54 at an angle A of between 5-30 degrees relative to the base 52. The angle A advantageously orients the penile prosthetic inserted into the recess 54 at an angle that approximates the orientation of the male penis relative to the male pubic bone.

Figure 6:
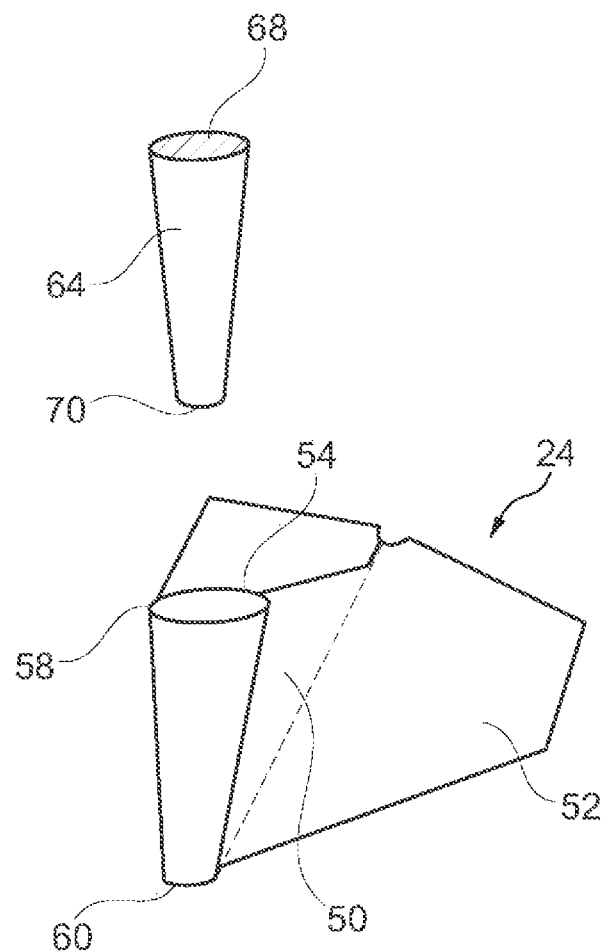
FIG. 6 is a perspective view of the implantable support illustrated in FIG. 4 and a plug insertable into the implantable support.

FIG. 6 is a perspective view of the implantable support 24 including one embodiment of an optional plug 64 that is insertable into the artificial crus penis recess 54. It is desirable to prevent tissue from growing inside of the artificial crus penis recess 54 after the implantable support 24 is implanted. As noted above, several weeks may elapse after the formation of the neophallus prior to implantation of the penile prosthetic. The plug 64 fills the artificial crus penis recess 54 during the healing process and prevents the undesirable ingrowth of tissue inside of the recess 54. The plug 64 extends between a distal end 68 a proximal end 70, each of which is sized to be similar to the size of the openings formed at the distal end 58 and the proximal end 60, respectively, of the artificial crus penis recess 54. One advantage of the plug 64 is that it aids the surgeon in locating the recess 54 when implanting the penile prosthetic 26.

Figure 7:
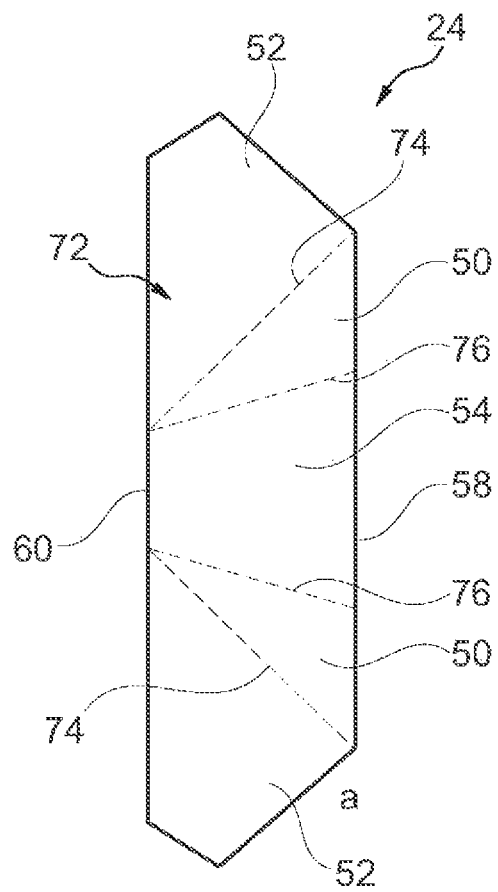
FIG. 7 is a top view of a sheet of material with demarcations useful in forming the implantable support illustrated in FIG. 4.

FIG. 7 is a top plan view of a sheet 72 of material that is used to integrally form the ligament 50 located between the base 52 and the artificial crus recess 54. In one embodiment, the sheet 72 of material is folded and includes a pair of first lines 74 demarcating the junction of the base 52 and the artificial ligament 50 and a second pair of lines 76 demarcating the junction between the artificial ligament 50 and the artificial crus penis recess 54. The sheet 72 is provided as a single sheet of material that is folded or otherwise formed to provide the base 52, the artificial ligament 50, and the artificial crus penis recess 54, the various components of which are held together with mechanical or chemical attachments. In one embodiment, the pair of the first lines 74 are folded into alignment and joined, and the second pair of lines 76 are folded into alignment and joined. The joints include stitching placed through the sheet 72 to form the base 52, the artificial ligament 50, and the artificial crus penis recess 54 as illustrated in FIG. 4. The sheet 72 is selected from materials such as autograft material (the patient's own tissue), allograft material (tissue from a cadaver), xenograft material (tissue from another species), or synthetic materials such as silicone, polyurethane, reinforced silicone, reinforced polyurethane, woven fabrics, meshes, nonwoven fabrics, meshes, fibrillated fibers, or spun and fibrillated fibers that are provided with voids (pores) configured to allow tissue ingrowth into the sheet 72. The pores are generally larger, on average, than 75 μm. In one embodiment, the implantable support 24 is integrally formed by molding or 3D printing employing a suitable polymer system.

Figures 8, 9:
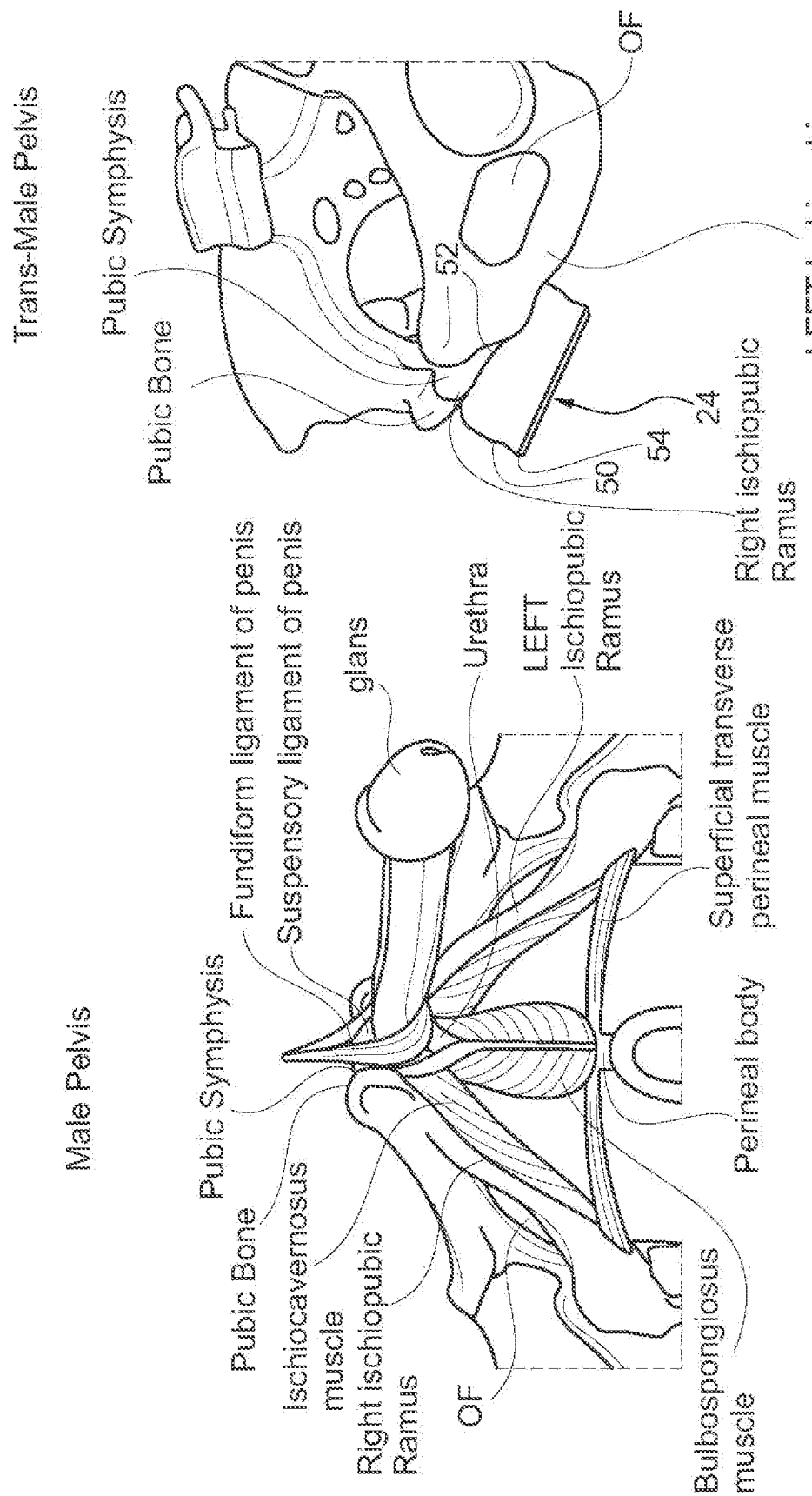
FIG. 8 is a front inferior view of a natal male pelvis.
FIG. 9 is a perspective view of a trans-male pelvis including the implantable support of FIG. 4 attached to the ischiopubic rami.
Figure 10:
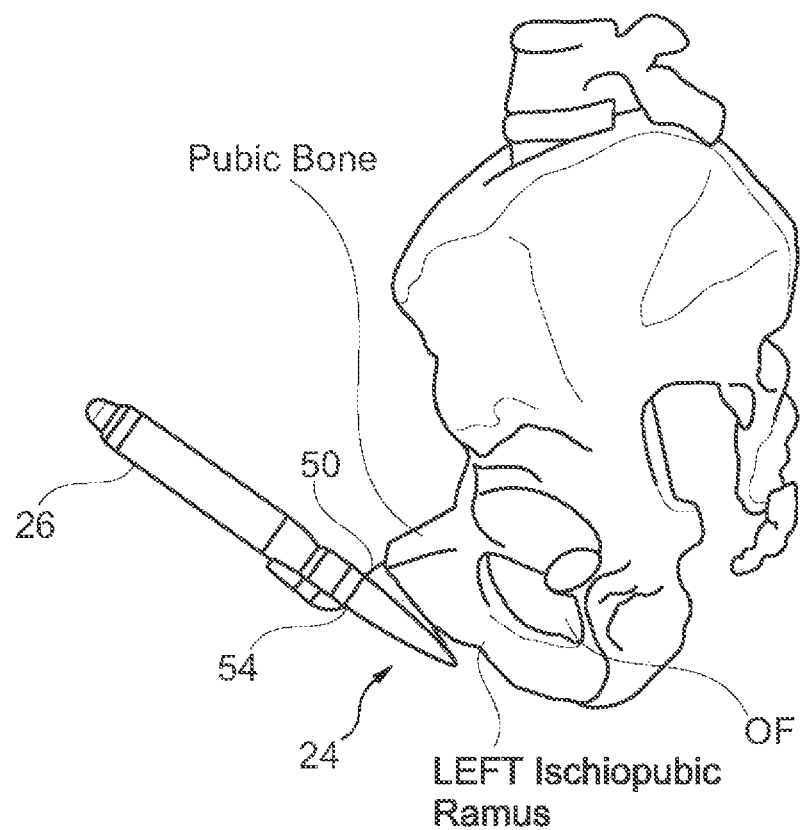
FIG. 10 is a side view of the trans-male pelvis and the implanted implantable support illustrated in FIG. 9.

FIG. 8 is a front inferior view of a male pelvis, and FIGS. 9 and 10 are perspective views of a trans-male pelvis including the implantable support 24 and the penile prosthetic 26. The male pelvis illustrates the shaft of the penis located inferior relative to the pubic bone and supported by the fundiform ligament of the penis. The ischiocavernosus muscle surrounds and supports the proximal portion of the penis to the ischiopubic ramus.

The implantable support 24 provides the trans-male pelvis with representative male anatomy. The male anatomy includes a proximal portion of the penis connected to the ischiopubic ramus, a ligament connected between the pubic symphysis and the base of the penis, and an orientation inferior to the pubic bone. Embodiments of the neophallus implant system 20 provides the person who was assigned the female sex at birth with an analog to the natal male anatomy, where: the base 52 of the implantable support 24 is attachable to the ischiopubic ramus to support the artificial crus penis recess 54 to allow the recess 54 to secure the proximal end portion of the penile prosthetic 26 in an anatomically suitable position. Embodiments further provide an artificial ligament 50 that suspends the artificial recess 54 from the base 52 at an angle to orient the penile prosthetic 26 in a manner that replicates the natal male anatomy.

The neophallus implant system 20 is configured to provide a person with a neopenis. The system 20 provides the penile prosthetic 26 having the shaft 41 connected between the distal end portion 34 and the proximal end portion 38. The distal end portion 34 is sized for implantation into the neophallus of the neopenis. The implantable support 24 is attachable to a descending ramus of a pelvis to provide an artificial crus penis. The proximal end portion 38 of the penile prosthetic 26 is coupled to the artificial crus penis 54 to locate the neopenis anatomically in a natal penis location.

The neophallus is formed by harvesting tissue from a donor site on the patient to form the tubular body of the neophallus. A neourethra is formed by harvesting tissue to form a neourethra. In one suitable approach, a surgeon harvests tissue for the neophallus from the radial forearm. It is desirable to harvest tissue from a donor site without hair follicles when forming the neourethra as the follicles have the potential to accumulate deposits from the urine and form a blockage. The interior portion of the radial forearm provides one possible location for the harvesting of tissue suitable for forming the neourethra. The neophallus is surgically attached to a location that is superior to the location of the natal urethra, since the natal female urethra is inferior relative to the bladder and the pubic bone. The surgeon may choose to begin expanding the labia in a first step of the scrotoplasty. It is desirable to allow the neophallus and the neourethra to heal for a period between 4-6 months before moving to the second stage of the FTM phalloplasty.

A vaginectomy is completed, which may be combined with laparoscopic hysterectomy and joining of the natal urethra with the neourethra. After joining the natal urethra with the neourethra the surgeon will perform glansplasty and any of the remaining steps of the scrotoplasty, for example placing testicular prostheses inside of the newly formed scrotum. The surgeon may choose to transport the clitoris to the base of the neophallus. It is desirable to allow the second stage to heal for a period between 4-6 months before moving to the third stage of the FTM phalloplasty.

The penile prosthetic 26 is implanted inside of the neophallus. The penile prosthetic 26 of the system 20 allows the neophallus to achieve an erection. The erect neophallus will not be well suited for penetrative intercourse unless the surgeon provides the neophallus with some form of a foundation that will support column-loading forces. The implantable support 24, having the artificial ligament 50 connected between the base 52 and the artificial crus penis recess 54, provides the neophallus with a foundation that will support column-loading forces. The implantable support 24 is formed and attached to the ramus as described above. The proximal end portion of the penile prosthetic 26 is inserted into the artificial crus penis recess 54 and the penile prosthetic 26 is connected to the reservoir 28 by the tubing 32 and is connected to the pump 30 by the tubing 32 (see FIG. 3). The artificial ligament 50 provides support to the prosthetic 26 and orients the implant in an orientation that mimics the natal male anatomy. The reservoir 28 and the pump 26 are implanted in the abdomen (or even subcutaneously) and the neoscrotum, respectively, and the incisions are closed. The trans-male is thus provided with a neopenis that is situated anatomically in a natal penis position and suited for penetrative intercourse.

FIG. 11A is a perspective view of one embodiment of an implantable support 84 and FIG. 11B is a perspective view of the implantable support 84 secured to the pelvis. In one embodiment, the implantable support 84 includes a pair of artificial ligaments 90a, 90b connected between a base 92 and a respective pair of artificial crus penis recesses 94a, 94b. The base 92 forms an implant bed that is attachable to the pelvis and each of the artificial crus penis recesses 94a, 94b is sized to receive a proximal end portion of a dual cylinder penile prosthetic. One example of a dual cylinder penile prosthetic is an inflatable dual cylinder system available from Coloplast Corp., Minneapolis, Minn. and identified as the TITAN® brand inflatable penile prosthesis. Another example of a dual cylinder penile prosthetic is a malleable dual cylinder system available from Coloplast Corp., Minneapolis, Minn. and identified as the GENESIS brand penile prosthesis. The artificial ligaments 90a, 90b are a connecting structure located between the base 92 and the artificial crus penis recesses 94a, 94b and are analogous to the fundiform suspensory ligament present in the natal male between the pubic bone and the penis.

In one embodiment, the artificial crus penis recesses 94a, 94b are conical in shape and tapers from a distal end to a proximal end in a manner that is sized to receive the proximal end portion of each cylinder of the penile prosthetic. In other embodiments, the artificial crus penis recesses 94a, 94b have a closed base and are cup-shaped. The artificial crus penis recesses 94a, 94b have a recess depth in a range from 0.5-7 cm, and preferably the recess depth for each of the artificial crus penis recess is between 1-4 cm.

The artificial crus penis recesses 94a, 94b are not parallel with the base 92. In one embodiment, the axes of the artificial crus penis recesses 94a, 94b are oriented at an acute angle A relative to the base 92, which is to say that the artificial ligaments 90a, 90b maintain each of the artificial crus penis recesses 94a, 94b at an angle A of between 5-30 degrees relative to the base 92. The angle A advantageously orients the penile prosthetic inserted into the recesses 94a, 94b at an angle that approximates the orientation of the male penis relative to the male pubic bone.

In one embodiment, an optional plug is insertable into each of the artificial crus penis recesses 94a, 94b to prevent tissue from encapsulating into the recesses.

FIG. 12 is a perspective view of one embodiment of an implantable support 100. The implantable support 100 includes a base 102 that is attachable to a pelvis of a person assigned the female sex at birth, and an artificial crus penis recess 104 connected to the base 102. The base 102 provides an implant bed that supports the artificial crus penis recess 104 to allow a person who was assigned the female sex at birth to have a neopenis that is situated anatomically in the same position as a natal penis.

In one embodiment, the base 102 is fabricated from human or animal tissue or a synthetic material. Suitable tissue include autograft material (the patient's own tissue), allograft material (tissue from a cadaver), or xenograft material (tissue from another species). Suitable synthetic materials include fabrics, textiles, or meshes formed from a polymer material. Examples of suitable synthetic materials include silicone, polyurethane, reinforced silicone, reinforced polyurethane, woven fabrics, meshes, nonwoven fabrics, meshes, fibrillated fibers, or spun and fibrillated fibers that are provided with voids (pores) configured to allow tissue ingrowth into the base 102. In one embodiment, the base 102 is fabricated from a mesh knitted from a polypropylene monofilament fiber, where the knitted mesh has a system of pores or holes or openings selected to allow tissue to grow through the mesh. The pores are generally larger, on average, than 75 µm.

In one embodiment, the base 102 extends between longitudinal edges 106, 108 and the lateral edges 110, 112. In one embodiment, a section of the base 102 between the lateral edge 110 and the artificial crus penis recess 104 forms an artificial ligament 114. The artificial ligament 114 is adapted to suspend and support the artificial crus penis recess 104 when the implantable support 100 is secured to the pelvis, and thus acts to provide the person assigned the female sex at birth with an analog to the fundiform ligament that is present in a natal male. The artificial ligament 114 provides the means for supporting an implanted penile prosthetic in a trans-male in an orientation of that of the penis of a natal male. The artificial ligament 114, in combination with the artificial crus penis recess 104, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

FIG. 13A is a top view, FIG. 13B is a perspective view, and FIG. 13C is an end view of the artificial crus penis recess 104. Regarding FIG. 12 and FIG. 13, the artificial crus penis recess 104 includes a distal base 116 that is attachable to the base 102, a proximal base 118, and a body 119 extending between the distal base 116 and the proximal base 118. In one embodiment, the proximal base 118 includes a suture port 120 that allows the surgeon to secure the proximal base 118 to the internal structure of the pelvis. For example, in one embodiment the suture port 120 is configured to receive a length of suture to allow the surgeon to secure the proximal base 118 to tissue within the pelvis, such as a ligament at the floor of the pelvis. In one embodiment, the distal base 116 includes a first portion 122 that is attachable to a second portion 124 of the artificial crus penis recess 104. The base 102 is captured between the first portion 122 and the second portion 124 to secure the base 102 relative to the artificial recess 104. For example, the first portion 122 is attachable to the second portion 124 by a friction fit, or a snap fit, or other form of closure with the base 102 located between the first portion 122 and the second portion 124. In one embodiment, the body 119 is tapered to converge from the distal base 116 to the proximal base 118. In one embodiment, the body 119 provides a tapered conical interior recess that is sized to receive a proximal end portion of a penile prosthetic.

Suitable materials for forming the artificial crus penis recess 104 include metal and plastic. One suitable metal includes stainless steel. Suitable plastics include polypropylene, polyethylene, silicone, or polysulfone. One example of the support 100 includes a polypropylene base 102 and a polypropylene artificial crus penis recess 104.

Figure 14:
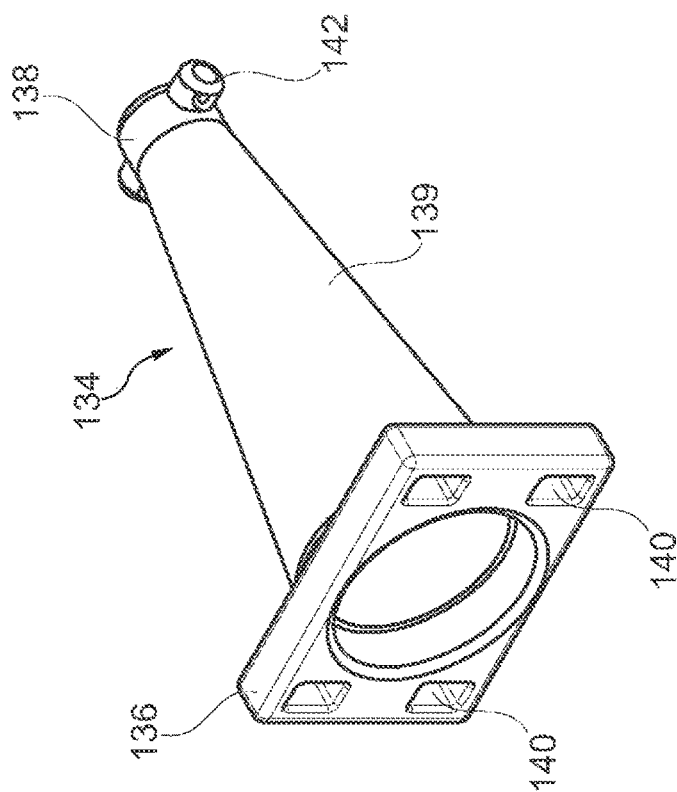
FIG. 14 is a perspective view of one embodiment of the artificial crus penis recess suitable for attachment to the base illustrated in FIG. 12.
Figure 16:
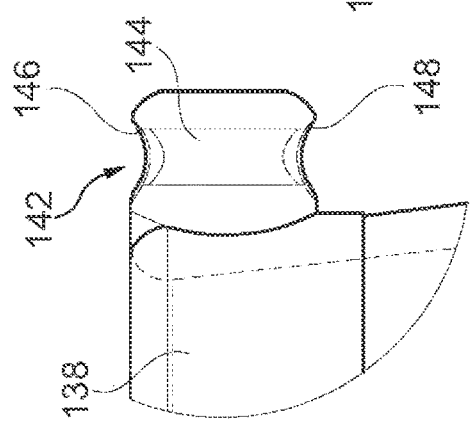
FIG. 16 is a schematic view of a proximal connector connected to the artificial crus penis recess illustrated in FIG. 14.
Figure 15:
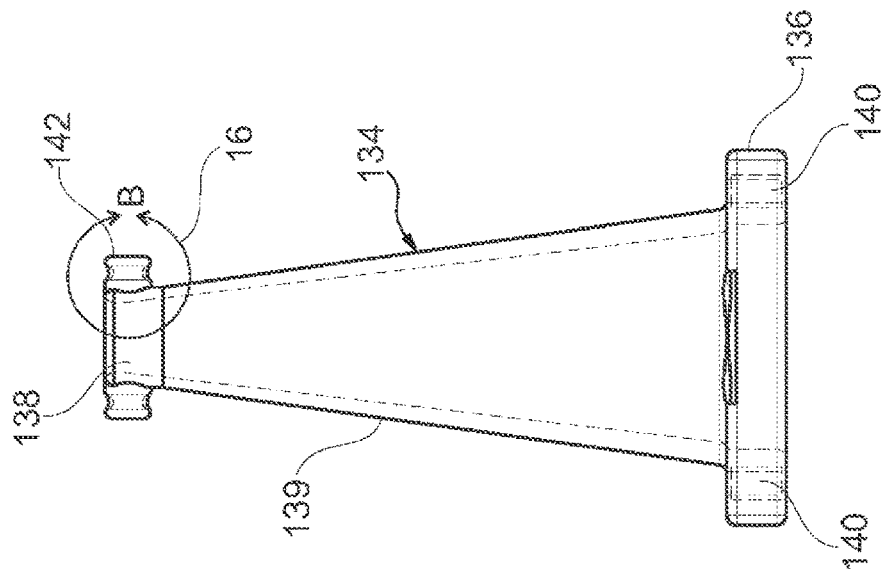
FIG. 15 is a top view of the artificial crus penis recess illustrated in FIG. 14.

FIG. 14 is a perspective view, FIG. 15 is a top view, and FIG. 16 is an expanded top view of one embodiment of an artificial crus penis recess 134.

In one embodiment, the artificial crus penis recess 134 includes a distal base 136, a proximal base 138, and a body 139 extending between the distal base 136 and the proximal base 138.

In one embodiment, the distal base 136 includes openings 140 that are configured to allow the distal base 136 to be attached to a support base with a mechanical coupling, such as the support base 102 (FIG. 12). The distal base 136 is illustrated as a rectangle, although other shapes of the perimeter are also acceptable, such as a circle shape, and oval-shaped, or a square shape.

In one embodiment, the proximal base 138 includes an anchor pad 142 that is configured to allow the surgeon to secure the proximal base 138 to tissue internal to the pelvis. In one embodiment, the anchor pad 142 is fabricated to include an orifice 144 with a smooth entrance 146 and a smooth exit 148. The orifice 144 is configured to receive a length of suture or other attachment material selected by the surgeon in suitable for anchoring to a ligament or other soft tissue inside of the pelvis.

FIG. 17 is a schematic view of a pelvis of a trans-male including the implantable support 100 secured to the pelvis. During the FTM phalloplasty procedure the vagina and other tissues are removed from the pelvis. The ischiocavernosus muscle remains attached to the ischiopubic ramus. The longitudinal edge 106 of the base 102 is secured to tissue of the right obturator foramen, the longitudinal edge 108 is secured to tissue of the left obturator foramen, and the artificial ligament 114 supports the artificial crus penis recess 104 inferior relative to the pubic bone. Implantation of the implantable support 100 is less invasive than drilling into the pubic bone, as is sometimes employed when securing a prosthesis to the pelvis of a trans-male. The implantable support 100 provides an anatomically appropriate support to the trans-male that allows placement of the penile prosthetic under or lower relative to the pubic bone as compared to those prosthetics that are screwed into the pelvic bone. The artificial ligament 114 provides a natural suspension structure superior (above) the artificial crus penis recess 104, which provides added support allowing penetrative intercourse with the implanted prosthetic.

Figure 18:
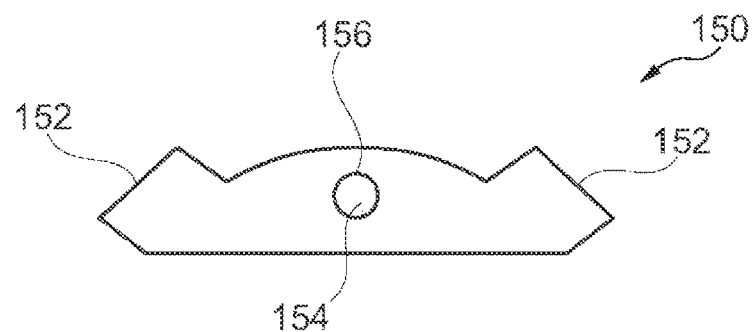
FIG. 18 is a front view of one embodiment of an implantable support.

FIG. 18 is a front view of one embodiment of an implantable support 150. The implantable support 150 is implantable into the pelvis of a trans-male to provide an implant bed that supports a penile prosthetic of a neopenis in a natal male orientation and to allow penetrative intercourse with the neopenis.

In one embodiment, the implantable support 150 includes a base 152 that is attachable to the descending pubic rami of the pelvis, and artificial crus penis recess 154 formed as a channel in the implantable support 150, and an artificial crus ligament 156 superior relative to the artificial crus penis recess 154. The artificial ligament 156 provides the means for supporting an implanted penile prosthetic in a trans-male in an orientation of that of the penis of a natal male. The artificial ligament 156, in combination with the artificial crus penis recess 154, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

In one embodiment, the base 152 and the artificial crus ligament 156 combine to form a bridge having an increased surface area at each side of the base 152. The increased surface areas of the base 152 are encased in bone putty. The bone putty is adapted to secure the base 152 to each of the descending rami to facilitate growing the base 152 into the rami. The bone putty is placed on the sides 152 of the support 150 and is selected to recruit osteoprogenitor cells to generate new bone growth. A suitable bone putty is formed from demineralized bone matrix processed from human bone and mixed with sodium hyaluronate. Another suitable bone putty is a NOVABONE® bioactive synthetic bone graft identified available from NovaBone, Jacksonville, Fla. In one approach, the bones of the rami are treated with a bone growth promoter that encourages osteogenesis and has a synergistic effect when in contact with the bone putty. The bone putty secures the support 150 to the bones of the rami by encouraging new bone growth around a portion of the support. The connecting bridge between the sides 152 includes the artificial crus penis recess 154, which is provided as a socket to retain a portion of the implanted prosthetic. One procedure includes lengthening of the urethra concurrent with formation of the neophallus during a first surgical procedure. The lengthened neourethra is formed with tissue harvested from the radial forearm, and the neophallus is formed with tissue harvested from the anterior thigh. A second surgery of the FTM phalloplasty procedure furthers the process by joining the lengthened neourethra to the natal urethra, followed by a vaginectomy, glansplasty at the distal neophallus, placement of testicular prosthetics, possible transposition of the clitoris to the base of the neophallus, and implantation of the support bonded to the rami with the bone putty. The body is given time to heal prior to implanting a penile prosthetic inside of the neophallus.

Figure 19A:
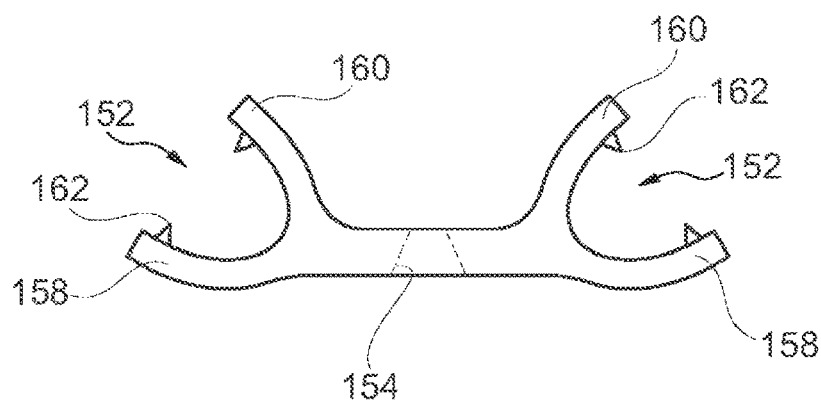
FIG. 19A is a top view of the implantable support illustrated in FIG. 18.

FIG. 19A is a top view of the implantable support 150. The base 152 forms a jaw that is sized to engage with the descending pubic ramus on each side of the pelvis. The base 152 or the jaw 152 includes a first clamping segment 158 connected to and spaced apart from a second clamping segment 160. The first clamping segment 158 is sized for attachment to an anterior surface of the descending pubic ramus and the second clamping segment 160 is sized for attachment to a posterior surface of the descending pubic ramus. During implantation, the surgeon will suitably dissect tissue away from the pelvis and affix the base 152 to the descending ramus with a tool that bends the jaw 152 into engagement with the bone of the ramus. In one embodiment, each of the first clamping segment 158 and the second clamping segment 160 includes an engagement tooth 162 that is adapted to penetrate and engage with the bone of the ramus.

The artificial crus penis recess 154 is formed as a channel through a thickness of the implantable support 150. In one embodiment, the proximal end portion of the penile prosthetic is conical, or frusto-conical, and the channel of the recess 154 is likewise conical and sized to accept the proximal end portion of the penile prosthetic.

Figure 19B:
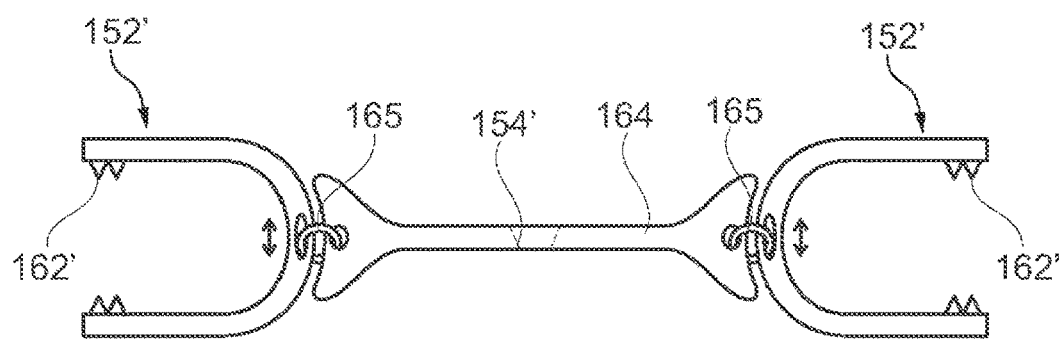
FIG. 19B is a top view of an alternative to the implantable support illustrated in FIG. 18.

FIG. 19B is an alternative embodiment to the implantable support 150 of FIG. 19A and includes an adjustable base 152' movably coupled to each end portion of a brace 164 of the implantable support by a sliding ring 165. A suitable artificial crus penis recess 154' is formed as a channel through a thickness of the brace 164 implantable support 150, where the through channel of the recess 154' supports the proximal end portion of the penile prosthetic. An artificial ligament is provided by that portion of the brace 164 that is superior to the artificial crus penis recess 154'. The location of attachment of the first adjustable base 152' on the patient's right side may not be at the same location along the descending ramus as a location of a second adjustable base 152' on the patient's left side. The sliding ring 165 allows the position of the adjustable base 152' to be move to a desired location before the surgeon secures the jaw 152' to the descending ramus. Engagement teeth 162' are provided on each of the adjustable bases 152' to ensure positive engagement between the base 152' and the ramus, even if the location of each of the bases 152' is not symmetric left-to-right on the patient. The artificial ligament 156' provides the means for supporting an implanted penile prosthetic in a trans-male in an orientation of that of the penis of a natal male. The artificial ligament 156', in combination with the artificial crus penis recess 154', provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

Figure 20A:
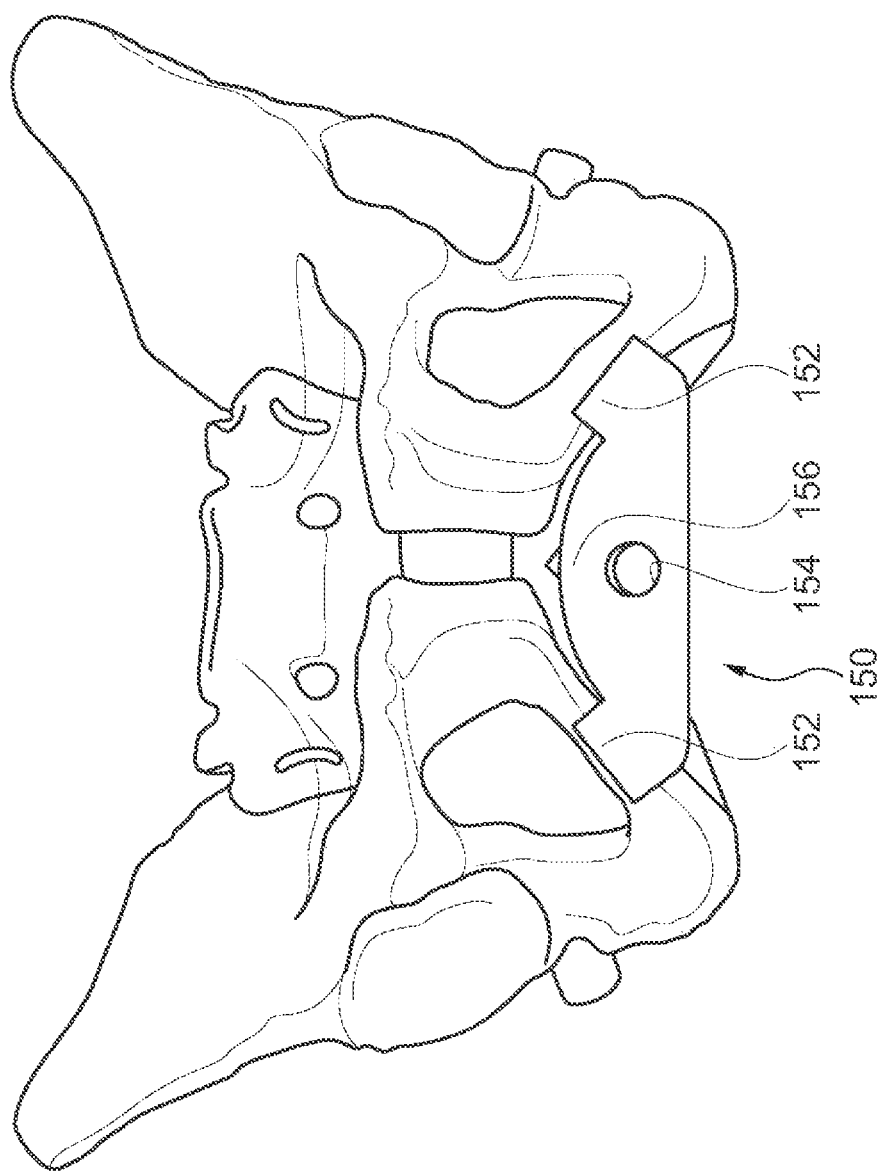
FIG. 20A is a schematic view of the implantable support illustrated in FIG. 18 affixed relative to a trans-male pelvis.

FIG. 20A is a schematic view of the implantable support 150 secured to a pelvis of a trans-male. A suitable vaginectomy or other dissection has prepared the tissue between the descending pubic rami to receive the implantable support 150. The base 152 is clamped into engagement with each of the respective descending pubic rami. The artificial crus penis recess 154 is located on the midline of the pelvis. The proximal end portion of the penile prosthetic is insertable into the recess 154 to locate the penile prosthetic anatomically in a natal penis position and that is suitable for penetrative intercourse. The artificial ligament 156 provides support to the penile prosthetic in in the area superior relative the recess 154, and is the analog to the fundiform ligament of the natal male.

FIG. 20B is a schematic view of the implantable support of FIG. 19B secured to a pelvis of a trans-male. One of the adjustable bases 152' is clamped into engagement with a ramus on the patient's right side and the second of the adjustable bases 152' is clamped into engagement with a ramus on the patient's left side. In this case, the right side adjustable base 152' is cephalad relative to the left side adjustable base. The artificial crus penis recess 154' is located near the midline of the pelvis and positioned to receive the proximal end portion of the penile prosthetic. The artificial ligament 156' provides support to the penile prosthetic in in the area superior relative the recess 154', and is the analog to the fundiform ligament of the natal male.

The implantable support 150 and its alternative (FIG. 19B) provide both a person assigned the female sex at birth and a natal male with a neopenis that is situated anatomically in an appropriate natal penis position and that is suitable for penetrative intercourse.

FIG. 21 is a schematic view of one embodiment of an implantable support 170 oriented relative to a schematic diagram of a pelvis of a trans-male, and FIG. 22 is a top view of the implantable support 170.

The implantable support 170 includes a base 172, an artificial crus penis 174, and an artificial ligament 176. The base 172 includes a first leg 176 connected to a second leg 178 by a bridge 180. The first leg 176 and the second leg 178 have a longitudinal length that is greater than a vertical length (or height) of the bridge 180. The increased longitudinal length of the legs 176, 178 adapts the implantable support to have an increased surface area in a location that is attachable to the pelvis. In one embodiment, the implantable support provides an implant bed and the legs 176, 178 in combination with the bridge 180 provides a frontal area that resembles a "dog bone." The first leg 176 is attachable to a descending ramus on the right-hand side of the patient, and the second leg 178 is attachable to a descending ramus on the left-hand side of the patient. Suitable attachment mechanisms include bone screws, clamps, adhesive coupling and a mesh-interface to drive tissue growth around the base 172. The bridge 180 spans between the legs 176, 178 to provide a supporting structure for the implantable support 170. The artificial ligament 176 provides the means for supporting an implanted penile prosthetic in a trans-male in an orientation of that of the penis of a natal male. The artificial ligament 176, in combination with the artificial crus penis recess 174, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

In one embodiment, the increased surface areas of the base 172 are encased in bone putty that is adapted to secure the base 172 to each of the descending rami to facilitate growing the base 172 into the rami. The bone putty is placed on the sides 172 of the support 170 and is selected to recruit osteoprogenitor cells to generate new bone growth. One suitable bone putty is formed from demineralized bone matrix processed from human bone and mixed with sodium hyaluronate. Another suitable bone putty is a NOVABONE® bioactive synthetic bone graft identified available from NovaBone, Jacksonville, Fla. In one approach, the bones of the rami are treated with a bone growth promoter that encourages osteogenesis and has a synergistic effect when in contact with the bone putty. The bone putty secures the support 170 to the bones of the rami by encouraging new bone growth around a portion of the support.

The artificial crus penis recess 174 is formed as a channel through a thickness of the implantable support 170. In one embodiment, the proximal end portion of the penile prosthetic is conical, or frusto-conical, and the channel of the recess 174 is likewise conical and sized to accept the proximal end portion of the penile prosthetic. When the penile prosthetic is secured within the artificial crus penis recess 174, the implantable support 170 provides a backboard or an implant bed that allows penetrative intercourse with the penile prosthetic.

Figure 23A:
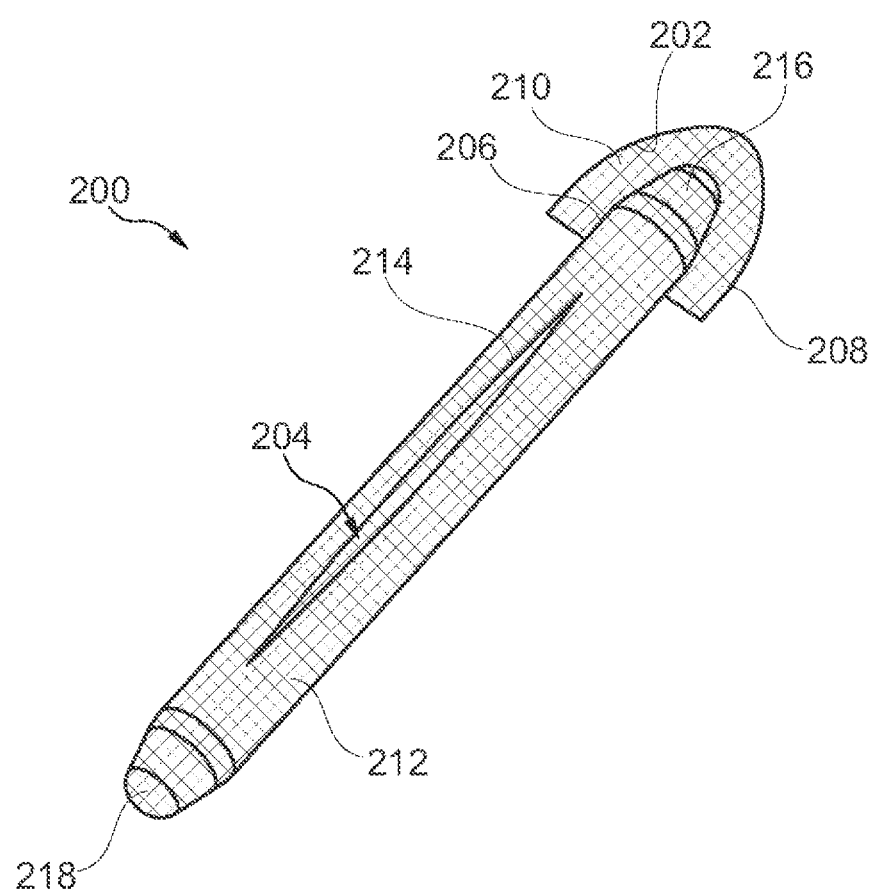
FIG. 23A is a perspective view of one embodiment of an implantable support including a sleeve forming an artificial crus penis recess.
Figure 23B:
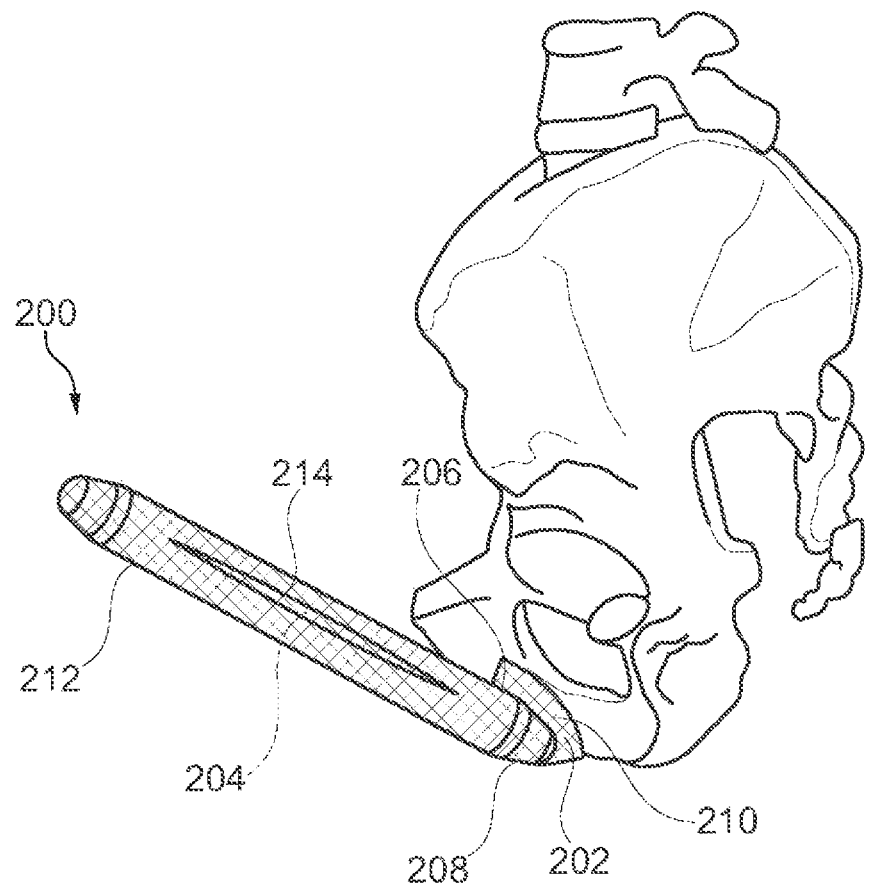
FIG. 23B is a schematic view of the implantable support illustrated in FIG. 23A affixed relative to a pelvis.

FIG. 23A is a perspective view of one embodiment of an implantable support 200, and FIG. 23B is a schematic view of the implantable support 200 secured to a pelvis of a trans-male.

The implantable support 200 includes a base 202, in artificial crus penis recess 204, and an artificial ligament 206 connected between the base 202 and the artificial crus penis recess 204. The artificial crus penis recess 204 is sized to receive a penile implant. The implantable support 200, as illustrated, does not contain a penile implant, but is sized to receive a penile implant in a subsequent step of the phalloplasty procedure.

In one embodiment, the base 202 provides a proximal end portion of the implantable support 200 and is adapted to be attached around a portion of a descending pubic ramus of the pelvis. In one embodiment, the base 202 is provided as a flap that has a first section 208 and an opposing second section 210. The base 202 is fabricated from a flexible material such as a fabric or a mesh and is analogous to ligaments that anchor a penis to the bony pelvis in a natal male.

The artificial crus penis recess 204 is a recess that is formed inside of the sleeve 212, where the sleeve 212 includes an opening 214. In one embodiment, the sleeve 212 approximates the shape of the tunica that surrounds the cavernous body of the corpora cavernosa of a natal male. The sleeve 212 extends from a proximal end portion 216 to a distal end portion 218. The proximal end portion 216 is secured to the base 202 by the artificial ligament 206. In one embodiment, the distal end portion 218 of the sleeve 212 includes a padded construction that is adapted to reduce or distribute pressure applied inside of the sleeve 212 by a penile prosthetic that is inserted into the sleeve 212, for example during penetrative intercourse. In one embodiment, the proximal end portion 216 also includes a padded construction to distribute the stress of the penile prosthetic pressing against the sleeve 212. Suitable padded construction includes silicone, a silicone pouch, a gel, a gel filled pouch integrated with the implantable support 200, or combinations of these. The sleeve 212 is an artificial tunica 212 for a neopenis implanted in a trans-male. The trans-male pelvis, and specifically the neophallus created for the trans-male pelvis, does not have a tunica. Conventional penile implants implanted into a neophallus of a trans-male have the possibility of undesirably eroding the tissue of the neophallus and poking through the skin (referred to as extrusion, or erosion). The artificial tunica provides the means for reducing erosion of an implanted penile prosthetic through the neophallus of a neopenis implanted in a trans-male. The artificial tunica provides the means for supporting the implanted penile prosthetic within the neophallus of the trans-male. The artificial tunica provides the means for reducing or preventing the movement of the implanted penile prosthetic within the neophallus off of the longitudinal axis of the neophallus.

The artificial ligament 206 provides the means for supporting an implanted penile prosthetic in a trans-male in an orientation of that of the penis of a natal male. The artificial ligament 206, in combination with the artificial crus penis recess 204, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

The opening 214 is sized to receive the shaft of the penile prosthetic. In one embodiment, the surgeon is instructed to close the opening 214 after insertion of the penile prosthetic.

The sleeve 212 is suitably fabricated from a textile material, a mesh material, or a fabric such as a polyester fabric or a reasonable and waterproof fabric formed from a fibrillated fiber of polytetrafluoroethylene.

FIG. 23B is a schematic view of the implantable support 200 attached to a pelvis of a trans-male. The first section 208 and the second section 210 of the base 202 are wrapped around a portion of the descending pubic ramus of the pelvis and secured, for example with a series of suture stitches. A penile prosthetic, for example a penile prosthetic as illustrated in FIG. 3 is inserted into the artificial crus penis recess 204 through the opening 214. The penile prosthetic extends along a length of the sleeve 212. The penile prosthetic and the sleeve 212 are supported by the artificial ligament 206, which is formed by a junction of the base 202 and the sleeve 212.

Figure 24A:
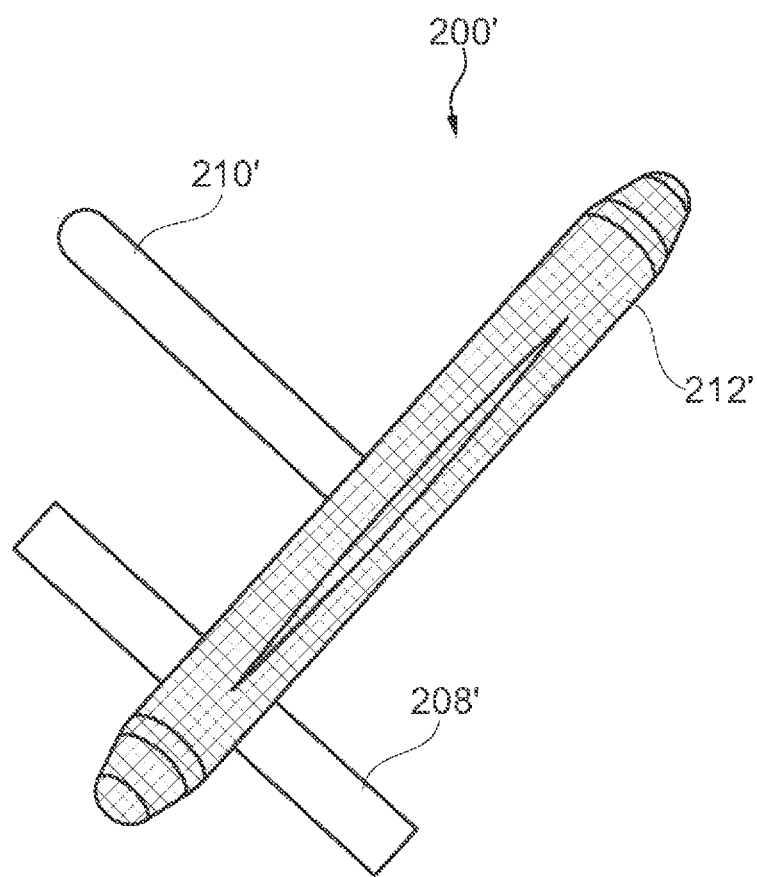
FIG. 24A is a perspective view of one embodiment of an implantable support including a sleeve provided with ramus straps.

FIG. 24A is a perspective view of one embodiment of an implantable support 200' including a sleeve 212' provided with ramus straps 208' and 210'.

The support 200' is like the support described above but additionally includes ramus straps 208' and 210' that are sized and located to fixate the sleeve 212' to the ramus by wrapping around the ramus and attaching back to the sleeve 212' or to the strap. The ramus strap 208' is a paired strap with each strap of the paired strap 208' adapted to surround the ramus and connect with its mate. The ramus strap 210' is a single strap sized for placement around the ramus and over the sleeve 212'. Suitable material for forming the straps 208' and 210' include woven fabrics, nonwoven fabrics, meshes, knitted fabrics, or films. In one embodiment, the straps 208' and 210' are formed from a knitted polypropylene mesh having a basis weight in a range from 50-200 g/m$^2$.

FIG. 24B is a schematic view of the implantable support 200' with the ramus strap 208' secured to an inferior portion of the descending pubic ramus and the ramus strap 210' secured to a superior portion of the descending pubic ramus. A similar support is attached to the contralateral descending pubic ramus. The supports 200' secure and retain a penile prosthetic, and the support 200' and the prosthetic are implanted into a neophallus. Embodiments of the support 200' locate the neopenis anatomically in the same position as a natal penis suitable for penetrative intercourse.

Figure 25:
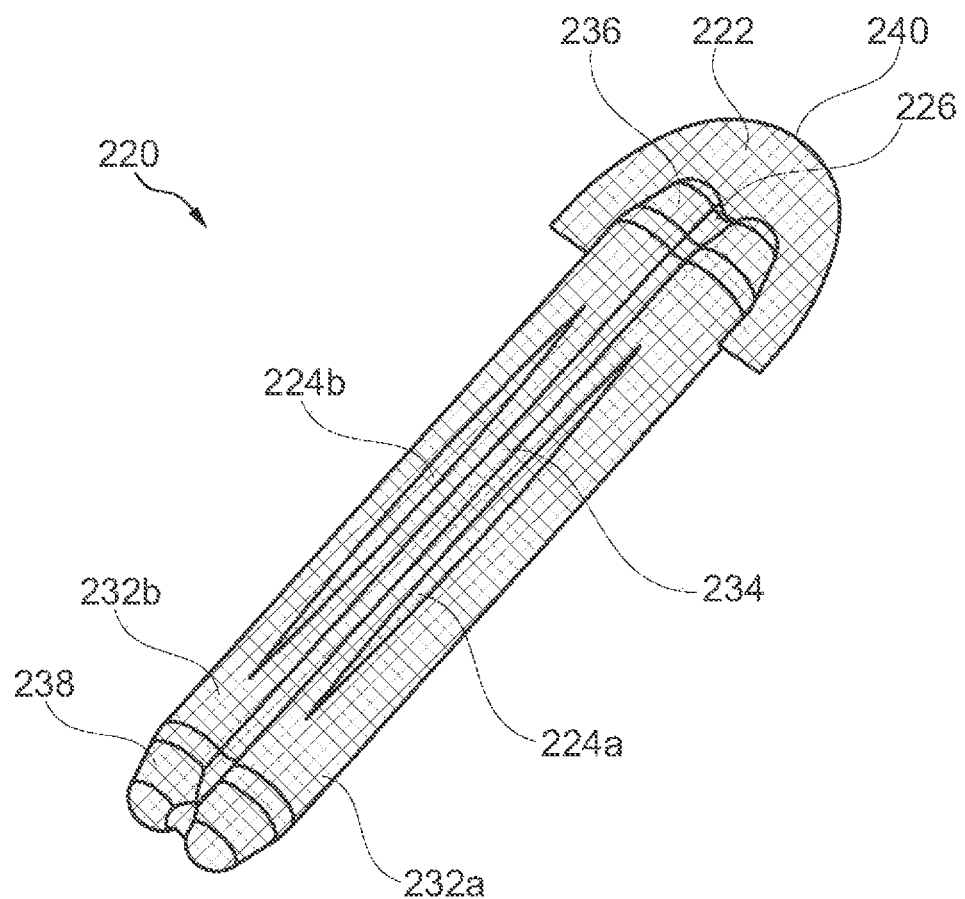
FIG. 25 is a perspective view of one embodiment of an implantable support including a single sleeve integrating a pair of artificial crus penis recesses.
Figure 26:
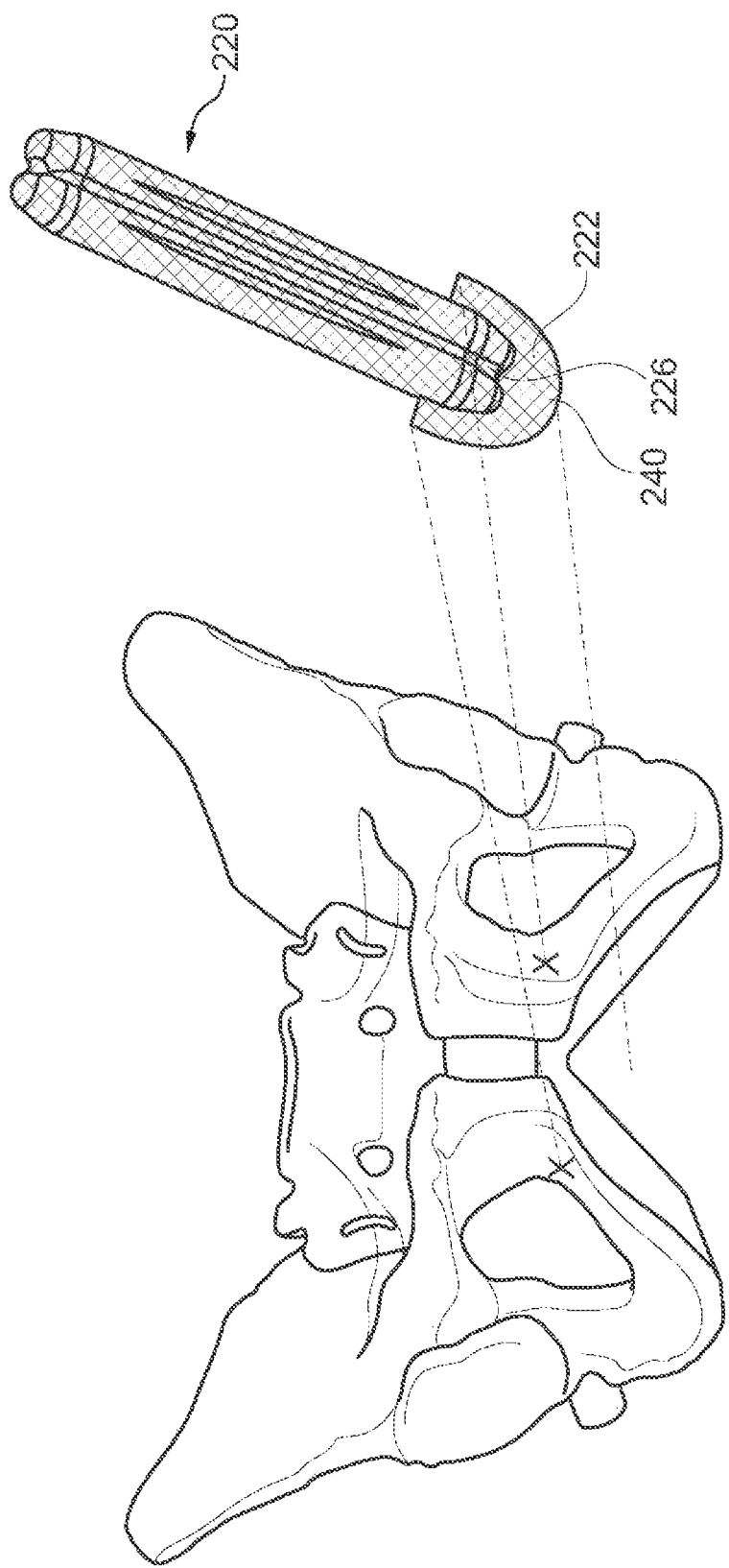
FIG. 26 is a schematic view of the implantable support illustrated in FIG. 25 oriented relative to a trans-male pelvis.

FIG. 25 is a perspective view of one embodiment of an implantable support 220 and FIG. 26 is a schematic view of the implantable support 220 relative to a pelvis of a trans-male.

In one embodiment, the implantable support 220 includes a base 222, a first artificial crus penis recess 224a and a second artificial crus penis recess 224b, and an artificial ligament 226. Some penile prosthetics are provided in a dual cylinder format, and the implantable support 220 provides a first sleeve 232a sized to receive one of the implantable cylinders and a second sleeve 232b sized to receive a second of the implantable cylinders of the penile prosthetic. Each of the first sleeve 232a and the second sleeve 232b provides an analog to the to the tunica surrounds each corpora cavernosum in the natal male penis. In one embodiment, the first sleeve 232a is joined to the second sleeve 232b by a midline junction that integrates the sleeves into one unit. In one embodiment, a proximal end portion 236 of the sleeves is tapered to receive a proximal end portion of the penile prosthetic, and a distal end portion 238 of each of the sleeves is tapered to receive the distal end portion of the penile prosthetic. In one embodiment, the distal end portion 238 of the sleeves is fabricated to provide a bulbous area that is an analog to the glans penis. In one embodiment, the implantable support 220 provides a coupled pair of artificial tunica

224a, 224b. The artificial tunica provides the means for reducing erosion of an implanted penile prosthetic through the neophallus of a neopenis implanted in a trans-male. The artificial tunica provides the means for supporting the implanted penile prosthetic within the neophallus of the trans-male. The artificial tunica provides the means for reducing or preventing the movement of the implanted penile prosthetic within the neophallus off of the longitudinal axis of the neophallus.

The artificial ligament 226 provides the means for supporting an implanted penile prosthetic in a trans-male in an orientation of that of the penis of a natal male. The artificial ligament 226, in combination with the artificial crus penis recesses 224a, 224b, provide the means for anatomically orienting an implanted penile prosthetic in a trans-male in a position of that of the penis of the natal male. The trans-male pelvis does not have a penile ligament (fundiform ligament) or a crus penis recess. The implantable supports described in this specification (having one of an artificial ligament or an artificial crus penis recess) provide the means for providing a trans-male with a neopenis having an implanted penile prosthetic, including providing the neopenis with the means for supporting penetrative intercourse, and the means for supporting the neopenis for accommodating the axial thrust that is associated with penetrative intercourse.

FIG. 26 is a schematic view of a trans-male pelvis and the implantable support 220.

Figure 27:
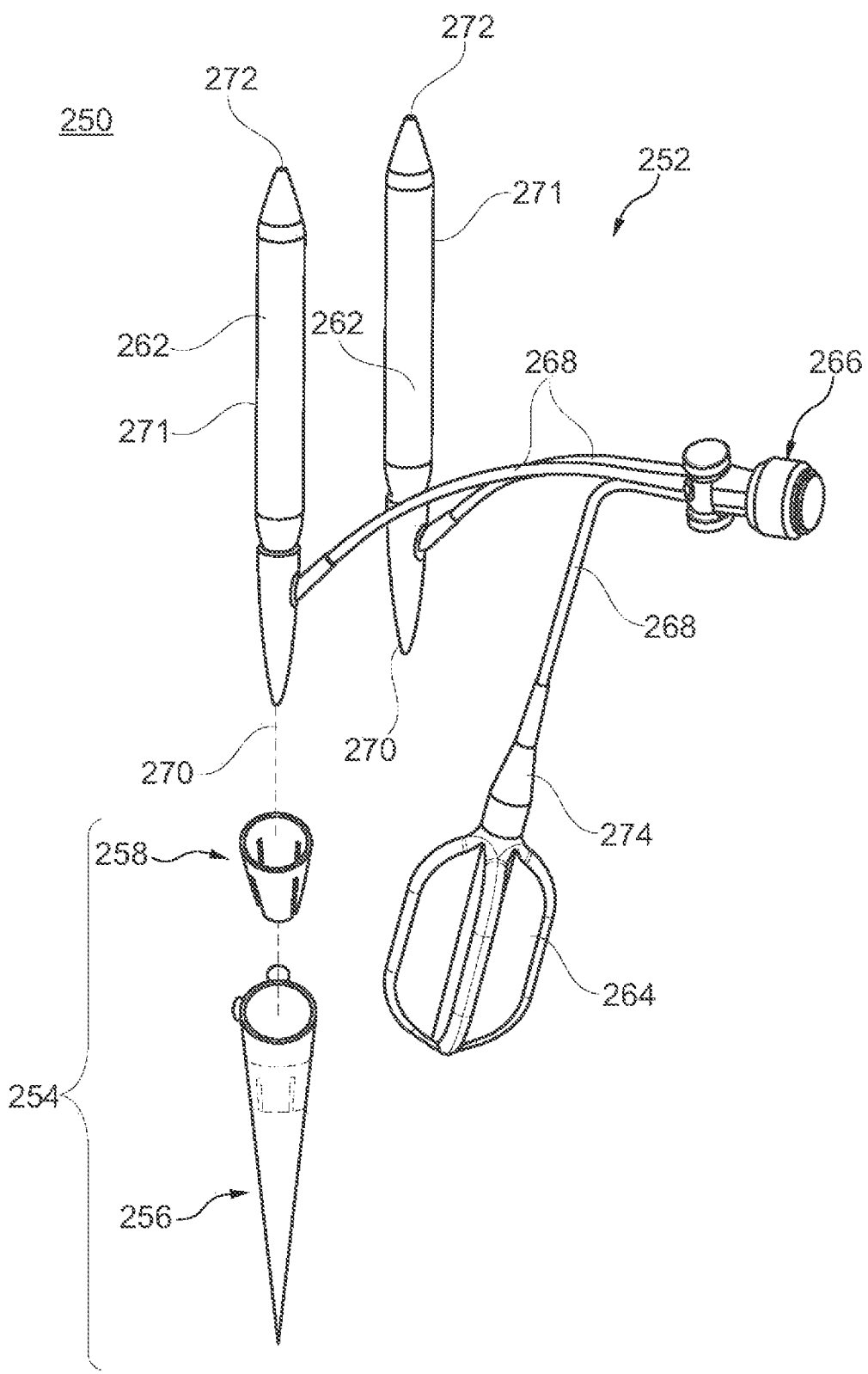
FIG. 27 is a perspective view of one embodiment of a neophallus implant system including a penile prosthetic and an implantable support.

The base 222 is sized to be affixed and bridge across from the left descending pubic ramus to the right descending pubic ramus. A proximal flap portion of the base 222 is provided for attachment to the perineal body. The artificial ligament 226 supports and orients each of the tunica sleeves 232a, 232b in an anatomically natal male position relative to the pelvis. FIG. 27 is a perspective view of one embodiment of a neophallus implant system 250 including a penile prosthetic 252 and an implantable support 254, where the implantable support 254 includes an artificial crus penis recess 256 and an adapter 258. The adapter 258 is configured to secure the penile prosthetic 252 to the artificial crus penis recess 256. During implantation, the implantable support 254 is secured to a portion of the ramus and to a portion of the pubic bone, such as the pubic symphysis, to support the penile prosthetic 252 implanted into a neopenis. The neophallus implant system 250 allows the neopenis to be situated anatomically in the same position as a natal penis suitable for penetrative intercourse.

A neophallus of a neopenis in a trans-male does not have a pair of tunica each surrounding a corpora cavernosum, as would be present in a natal penis. Some penile prosthetics implanted in men to treat erectile dysfunction have two prosthetic tubes, or cylinders, each of which is implanted into one of the dilated corpora cavernosa. Some surgeons desire to employ such a two-cylinder prosthetic during FTM phalloplasty, and the neophallus implant system 250 is adapted to provide an artificial crus penis recess 256 for each of the cylinders of the two-cylinder prosthetic.

The penile prosthetic 252 includes cylinders 262 for implantation into a neophallus, a reservoir 264, and a pump 266 connected to the cylinders 262 and the reservoir 264, for example by kink resistant tubing 268.

Each of the cylinders 262 includes a shaft 271 extending between a proximal end 270 and a distal end 272 of the cylinder 262. The cylinders 262 are fabricated from material configured to collapse when the cylinders 262 are deflated to provide the neopenis with a flaccid state and expand when the cylinders 262 are inflated with liquid to provide the neopenis with an erection. Suitable material for fabricating the cylinders 262 includes silicone, biocompatible polymers such as urethanes, and blends of polymers with urethane, copolymers of urethane, or the like. One suitable inflatable prosthetic useful with the implant system 250 is the TITAN® inflatable penile prosthetic available from Coloplast Corp., Minneapolis, Minn.

The reservoir 264 is sized to maintain a volume of liquid between about 50-300 ml and includes a neck 274 that is smoothly coupled with the kink resistant tubing 268. In one embodiment, the reservoir 264 is provided as a "cloverleaf" style of reservoir having multiple flanges that may be folded one against the other to compact the reservoir 264 for implantation into the abdomen of the user. One suitable reservoir 264 is sized to retain approximately 130 mL of liquid and is available from Coloplast Corp., Minneapolis, Minn.

The artificial crus penis recess 256 is adapted to accommodate an inflatable penile prosthetic, such as the penile prosthetic 252, or a malleable and non-inflatable penile prosthetic. The malleable penile prosthetic provides a pair of rods that are adapted to be formed/bent by the user into a desired configuration (erect or non-erect, as examples). The malleable prosthetic is not inflatable, and instead forms an erection by column strength provided by a silver wire rod enclosed in a flexible polymer sheath. One suitable malleable penile prosthetic useful with the implant system 250 is the GENESIS malleable penile prosthesis available from Coloplast Corp., Minneapolis, Minn.

Figure 28A:
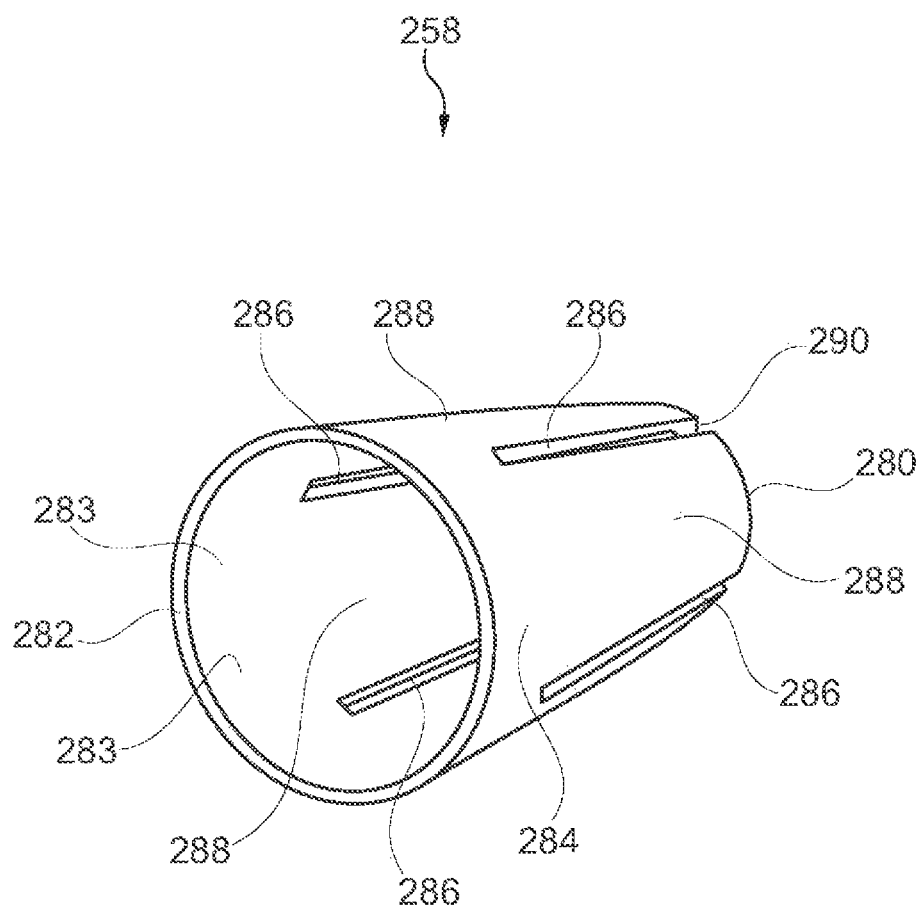
FIG. 28A and FIG. 28B are perspective views of one embodiment of an adapter of the implantable support illustrated in FIG. 27.
Figure 28B:
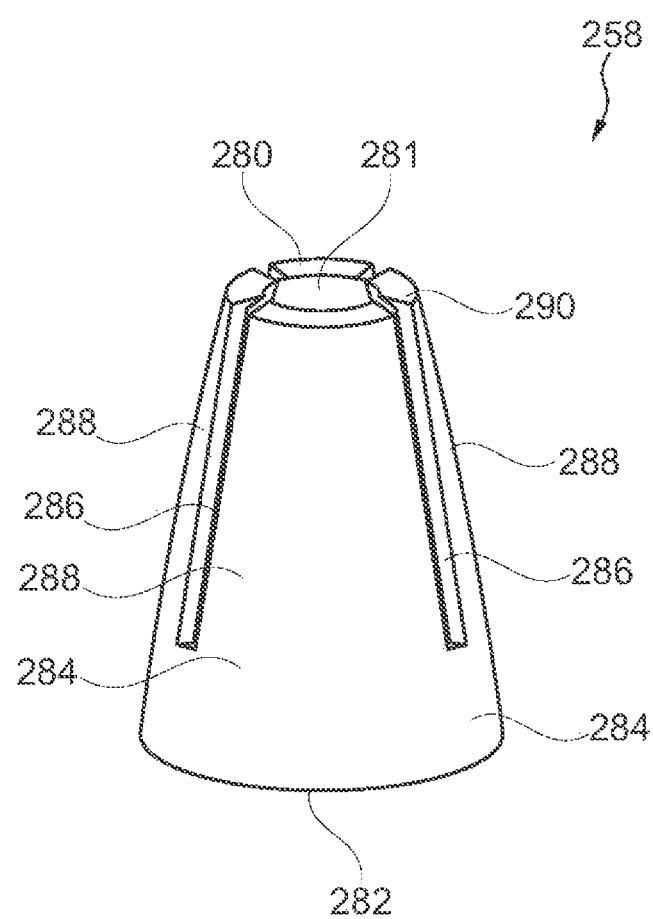

FIG. 28A and FIG. 28B are perspective views of the adapter 258. The adapter 258 is as described in U.S. Pat. Appln. Pub. 2010/0121137, which issued as U.S. Pat. No. 7,976,457, the disclosure of which is incorporated by reference in its entirety into this application. The adapter 258 has a proximal end 280 opposite of a distal end 282, where each of the ends 280, 282 include an opening 281, 283, respectively. The adapter 258 includes a side surface 284 extending between the ends 280, 282. A series of slots 286 is formed in the side surface 284 to provide the adapter 258 with the fingers 288. A lip 290 is provided at the proximal end 280 of the adapter 258. The combination of the fingers 288 and the lip 290 allow the adapter 258 to flex open to receive the proximal end 270 of the cylinder 262 of the penile prosthetic. The lip 290 is configured to bite down upon the proximal end portion of the cylinder 262 to prevent sliding of the cylinder relative to the artificial crus penis recess 254. In one embodiment, the lip 290 extends from the side surface 284 at an angle in a range from 5-140 degrees. The angle of the lip 290 allows the adapter 258 to engage with the proximal portion of the cylinder 262.

Figure 29C:
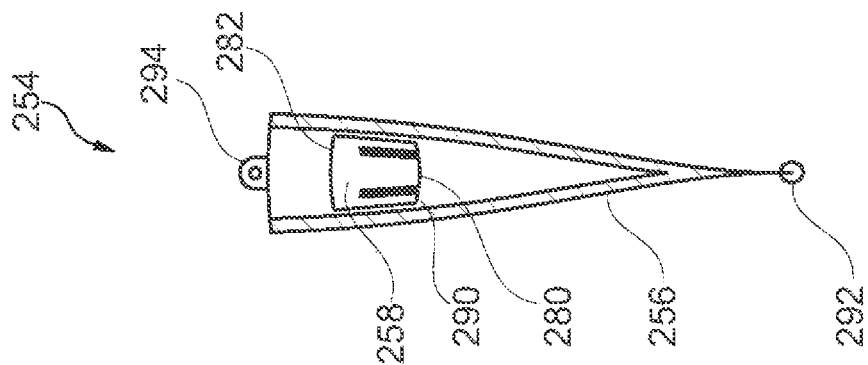
FIG. 29C is a perspective view of the implantable support illustrated in FIG. 27.
Figure 29B:
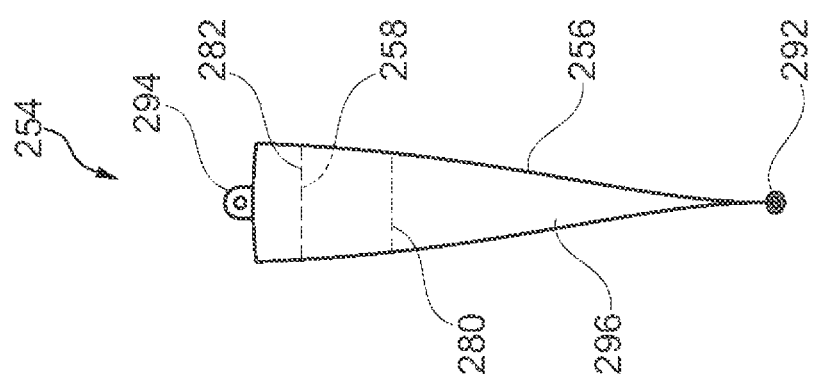
FIG. 29B is a front view.
Figure 29A:
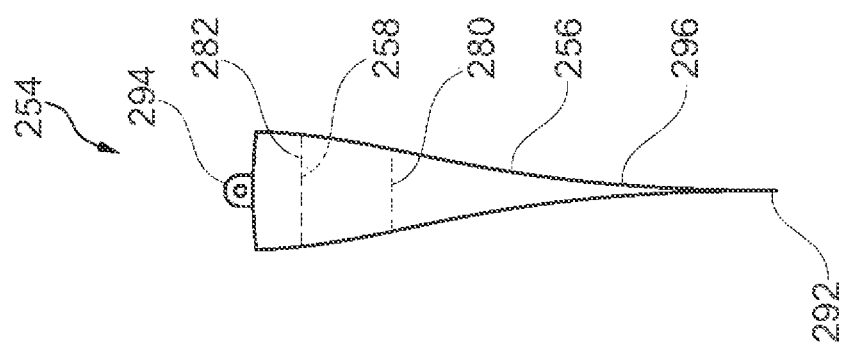
FIG. 29A is a side view.

FIG. 29A is a side view, FIG. 29B is a front view, and FIG. 29C is a cross-sectional view of the implantable support 254. In one embodiment, a proximal attachment tab 292 is connected to the implantable support 254 and configured for attachment to a descending ramus of the person, and a distal attachment tab 294 is connected to the implantable support 254 and configured for attachment to a pubic bone or a pubic symphysis of the person.

FIG. 29A is a side view of the implantable support 254 illustrating a proximal portion 296 that tapers to a flat plate that is suitable for affixing to the descending pubic ramus. FIG. 29B is a front view illustrating that the proximal portion 296 has a frontal area that is larger than the side area illustrated in FIG. 29A. The wider frontal area of the proximal portion 296 is configured to lie against the descending ramus in a flattened configuration that is suitable for attachment to either the periosteum or the bone of the pelvis. In one embodiment, the proximal attachment tab 292 is sutured to the periosteum tissue of the descending ramus, the distal attachment tab 294 is sutured to either the periosteum tissue of the pubic bone where the pubic symphysis, and the reinforcing suture (or stay suture) is sutured through the proximal portion 296 of the implantable support 254 to ensure that the artificial crus penis recess 256 adopts the anatomical configuration along the ramus of the natal crus penis.

FIG. 29C is a cross-sectional view illustrating the adapter 258 secured inside of the artificial crus penis recess 256. The distal end of the adapter 282 is arranged adjacent to the distal attachment tab 294 and the proximal end 280 of the adapter 258 is inserted into the tapered region of the artificial crus penis recess 256. The proximal portion of the cylinder 262 (FIG. 27) is inserted into the opening at the distal end 282 of the adapter 258 and inserted through the opening formed in the proximal end 280 of the adapter 258 until the plurality of lips 290 clamps radially against the proximal portion of the cylinder 262.

Figure 30:
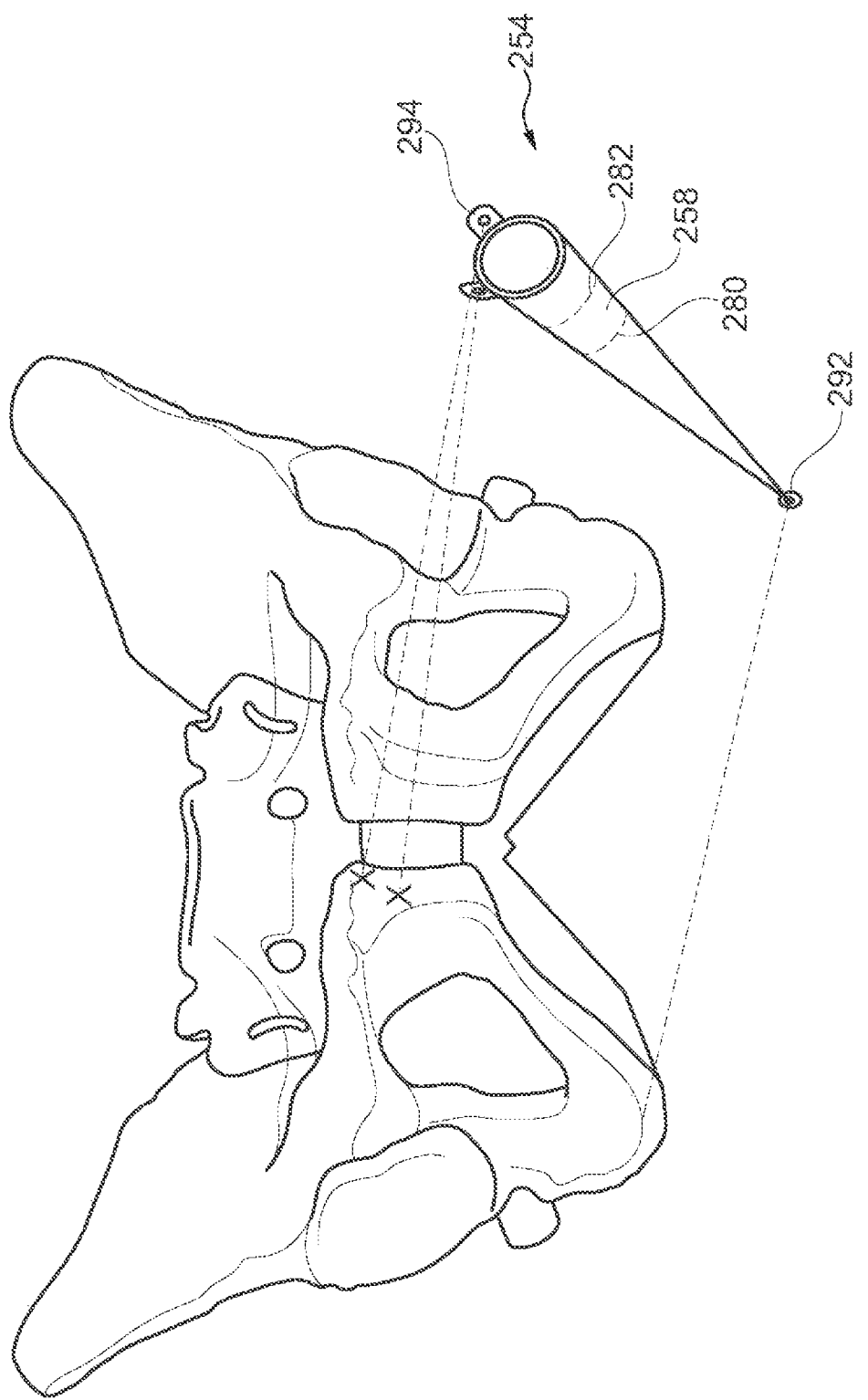
FIG. 30 is a schematic view of the implantable support illustrated in FIG. 27 oriented for implantation onto a pelvis.

FIG. 30 is a schematic view of a pelvis in the implantable support 254. In one embodiment, the implantable support 254 includes a plurality of distal attachment tabs 294, with one of the tabs 294 adapted for attachment to the pubic bone and the second of the tabs 294 adapted for attachment to the pubic symphysis. The proximal attachment tab 292 is attachable to the tissue of the descending pubic ramus. Attachment of the implantable support 254 along the descending pubic ramus appropriately orients the implantable support 254 to support the penile prosthetic 262 anatomically in the same position as a natal penis suitable for penetrative intercourse.

With reference to FIG. 27, after attachment of the implantable support 254, the surgeon implants the cylinders 262 of the penile prosthetic into the neophallus to form a neophallus. The proximal end 270 of the cylinder 262 is inserted through the adapter 258, and the distal end 272 of the cylinder 262 is placed in the distal end of the neophallus. The reservoir 264 is implanted in a location within the pelvis or within the abdomen, depending upon the preference of the surgeon. The pump 266 is implanted within the neoscrotum. The cylinders 262 are inflatable by operation of the pump 266 to move liquid from the reservoir 264 and into the cylinders 262 to provide the neopenis with an erection. The reservoir 264, the pump 266, and the tubing 268 are as described in U.S. Pat. Appln. Pub. 2011/0118540, which issued as U.S. Pat. No. 8,337,392, the disclosure of which is incorporated by reference in its entirety into this application.

Optionally, the surgeon implants a malleable penile prosthetic that is secured into the implantable support 254.

Embodiments of the implantable support 254 provide a two-piece anchor system, where the support 254 is configured to be implanted and attached to the ramus, and a penile prosthetic is insertable into and retained by the implantable support 254. For example, in one approach, the surgeon implants the implantable support 254 in a first surgical procedure and places a removable gauze or other filler to maintain the opening in the support 254. The patient is allowed to heal. The surgeon subsequently implants a prosthetic into the implantable support 254 in a second procedure, for example as the prosthetic is mated to the neophallus.

In one embodiment, the implantable support 254 is formed by the patient's own tissue in the form of a bone graft anchor. The bone graft anchor is formed by removing a portion of bone from the pelvis from the patient, for example a portion of the iliac crest, the ilium, the anterior inferior iliac spine, or other another surface of the pelvis that is accessible during the phalloplasty procedure. The bone is grafted onto the descending ramus and is adapted to anchor the proximal end portion of a penile prosthetic. In this way, the patient's own tissue is employed to form a structural zone that provides a foundation to support axial forces associated with penetrative intercourse. In one embodiment, a method of implanting a penile implant to provide a person who was assigned the female sex at birth with a neopenis suitable for penetrative intercourse includes harvesting bony tissue during a FTM phalloplasty procedure. The method includes removing a portion of bone from one of the iliac crest, the ilium, the anterior inferior iliac spine, or other another surface of the pelvis; grafting the harvested bone to the ramus in a bone graft and forming a fixation zone with the bone graft; and attaching a penile prosthetic to the bone graft. The method can be combined with laparoscopic hysterectomy, joining of the lengthened neourethra to the natal urethra, vaginectomy, glansplasty at the distal neophallus, placement of testicular prosthetics, or transposition of the clitoris to the base of the neophallus.

Figure 31:
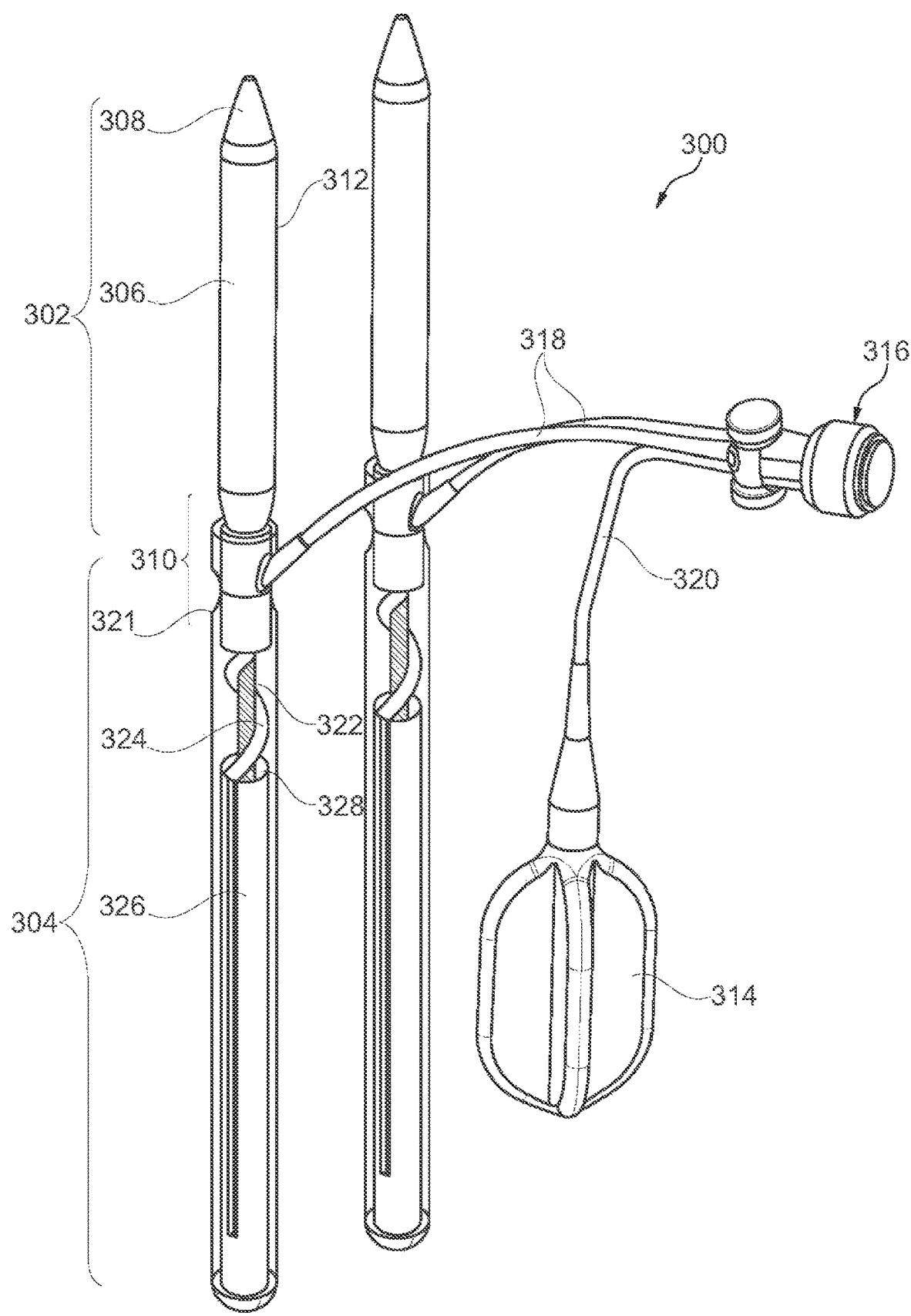
FIG. 31 is a perspective view of one embodiment of a neophallus implant system including a penile prosthetic and an implantable support.

FIG. 31 is a perspective view of one embodiment of a neophallus implant system 300 including a penile prosthetic 302 and an implantable support 304.

The neophallus implant system 300, when implanted, provides a person with a neopenis. The penile prosthetic 302 has a shaft 306 connected between a distal end portion 308 and a proximal end portion 310. The distal end portion 308 is sized for implantation into the neophallus to form that portion of the neopenis. The implantable support 304 is attachable to a descending ramus of a pelvis, and when implanted, provides an artificial crus penis 304. The proximal end portion 310 of the penile prosthetic 302 is coupled to the artificial crus penis 304 to locate the neopenis (neophallus plus the prosthetic 302) anatomically in a natal penis location.

In one embodiment, the penile prosthetic 306 is inflatable and includes an inflatable tubular body 312 coupled to a reservoir 314 and a pump 316. The pump 316 is coupled to the tubular body 312 by a tube 318, and the pump 316 is coupled to the reservoir 314 by a separate tube 320. The pump 316 is operable to move liquid retained in the reservoir 314 into the tubular body 312. The increased volume of liquid in the tubular body 312 increases the pressure inside of the tubular body 312 providing the penile prosthetic 302 with an erect state.

In one embodiment, the tube 318 is coupled to the proximal end portion 310 of the penile prosthetic 302 such that the implantable support 304 is connected to the penile prosthetic 302 by an inflatable and flexible hinge 321. In this embodiment, the implantable support 304 provides a rigid support that is adapted for surgical attachment to the descending ramus and the penile prosthetic 302 is inflatable to provide the neophallus of the trans-male with an erection. The inflatable and flexible hinge 321 allows a non-linear coupling between the penile prosthetic 302 and the implantable support 304 to allow positioning of the neopenis in the trans-male in a location in position of that of a penis in a natal male.

Suitable material for fabricating the tubular body 312 includes silicone, biocompatible polymers such as urethanes, and blends of polymers with urethane, copolymers of urethane, or the like.

The reservoir 314 is sized to maintain a volume of liquid between about 50-300 ml. In one embodiment, the reservoir 314 is configured to be pressed into a small volume package when empty, which configures the reservoir 314 for implantation into small spaces located within the abdomen of the user. One suitable reservoir 264 is sized to retain approximately 130 mL of liquid and is available from Coloplast Corp., Minneapolis, Minn.

In one embodiment, the implantable support 304 is a shaft of continuously solid polymer material that is adapted to provide column strength to the penile prosthetic 302. In one embodiment, the implantable support 304 is a combination of a rigid proximal end portion and a flexible portion 310, which adapts the implantable support 304 to be bendable and positionable for implantation alongside a descending pubic ramus of the pelvis.

In one embodiment, the implantable support 304 is a malleable support including a metal core 322, a malleable metal coil 324 wrapped around the metal core 322, and elastomer shaft 326 placed over the core 322 and the coil 324. In one embodiment, the metal core 322 is formed from silver, and the metal coil 324 is a silver coil located around the metal core 322. In one embodiment, the metal core 322 and the coil 324 are enclosed in a polymer sheath 328 which is covered by the elastomer shaft 326. The polymer sheath 328 provides added column strength to the implantable support 304. One suitable elastomer the elastomer shaft 326 is silicone. Suitable polymers for the polymer sheath 328 include polyester, polyurethane, silicone, or polyolefins.

In one embodiment, the penile prosthetic 302 is integrated with the implantable support 304. In one embodiment, the penile prosthetic 302 is provided separately and attachable to the implantable support 304.

During implantation, the implantable support 304 is placed alongside the descending pubic ramus and secured at one or more locations along the pubic ramus and on the pubic bone. Suitable locations for affixing the implantable support 304 to the pubic ramus include a proximal portion of the ramus, a midportion of the ramus, and the pubic symphysis. Suitable attachment of the implantable support to the pubic ramus include sutures placed through the shaft 326 and the periosteum over the bone of the ramus. Other mechanical connections of the implantable support 304 to the pubic ramus are also feasible, such as textile wraps, or screws, depending upon the surgeon's preference. In any regard, the penile prosthetic 302 extends from the implantable support 304 and is sized for implantation into a neophallus. The implantable support 304 provides the system 300 with an artificial crus penis that supports the penile prosthetic 302. The penile prosthetic 302 is inflatable to provide the person with an erection. The implantable support 304 provides a backboard or a foundation that allows the inflated prosthetic 302 to have the strength and durability that is suitable for penetrative intercourse. The location of the implantable support 304 along the pubic ramus, in combination with the inflatable penile prosthetic 302, results in locating the neopenis anatomically in a similar or the same location as a natal penis location relative to the pelvis.

Figure 32:
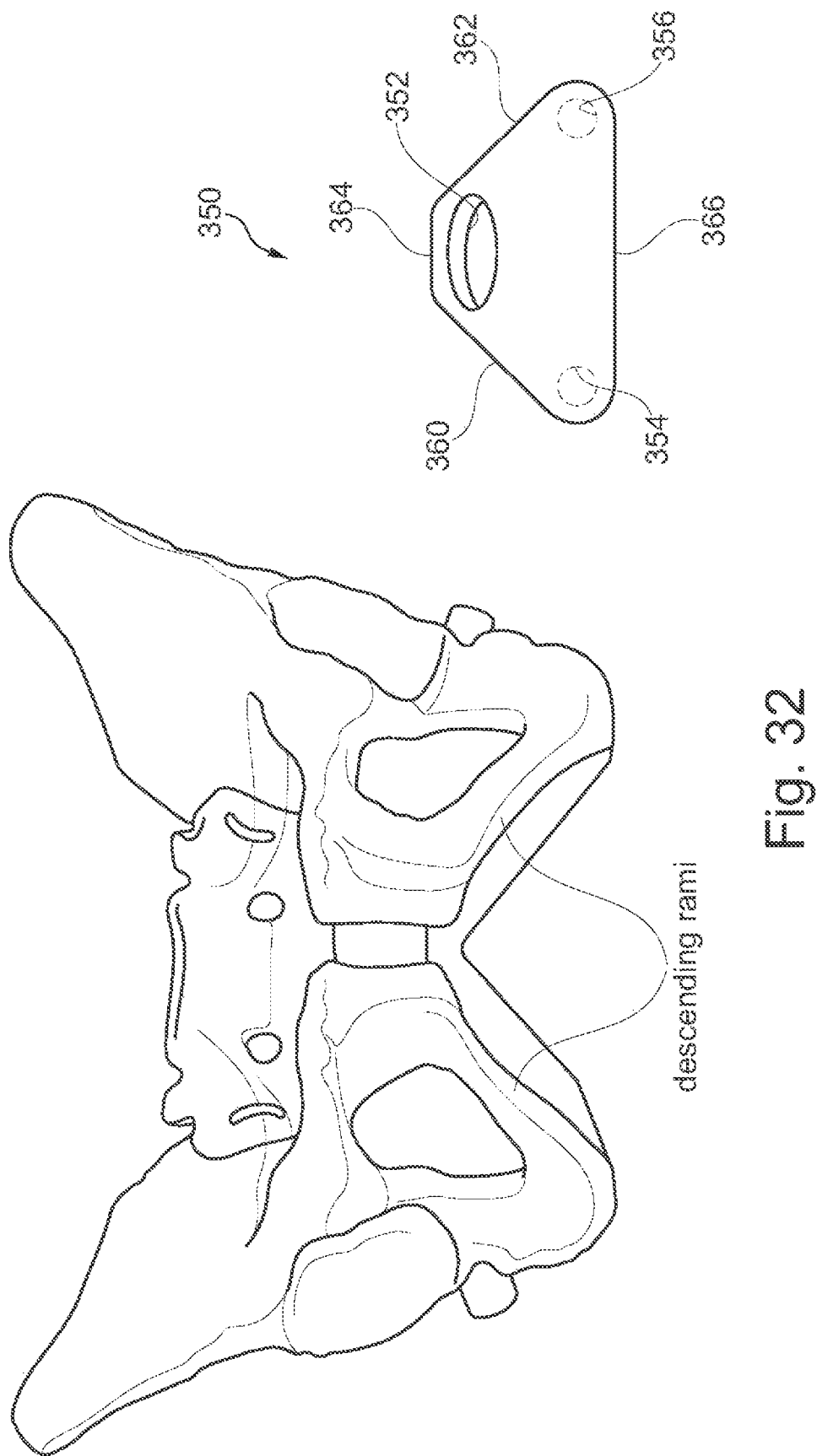
FIG. 32 is a schematic view of one embodiment of an implantable support located relative to a pelvis.

FIG. 32 is a schematic view of one embodiment of an implantable support 350 located relative to a pelvis. The implantable support 350 is adapted to support the single implantable prosthesis 22 (FIG. 3) or the dual-cylinder penile prosthetic 302 (FIG. 31). The implantable support 350 includes a receptacle 352 sized to receive and stabilize the proximal portion of a single implantable prosthesis or both of the dual-cylinder prosthetics. The receptacle 352 forms the artificial crus penis of the support 350. The implantable support 350 includes a first connector 354 and a second connector 356, where the connectors 354, 356 are configured to receive the respective proximal end of each of the dual-cylinder prosthetics.

The implantable support 350 includes a first lateral side 360 that is angled and shaped for connection along a length of the patient's right descending ramus, a second lateral side 362 that is angled and shaped for connection along a length of the patient's left descending ramus, and a top side 364 that is sized and shaped to span a distance across the pubic bone of the pelvis. The sides 360, 361 may be sutured or connected to the periosteum over the ramus bone, or may be secured around a portion or an entirety of the circumference of the ramus. When secured by sutures, the support 350 includes mounting holes through which a needle and suture pass to secure the support 350 to the pelvis. The top side 364 may be attached to the periosteum over the pubic bone, or to the periosteum over the pubic bone and to the pubic symphysis. The support 350 includes a lower side 366 that bridges between the ramus bones to provide a wide area of support that allows the prosthetic, when implanted, to have sufficient column strength for penetrative intercourse.

When implanted, and connected to the pelvis, the receptacle 352 of the support 350 receives the proximal end portion of the penile prosthetic in the fashion of a crus penis to locate the prosthetics within the neophallus anatomically in a natal penis location.

Figure 33:
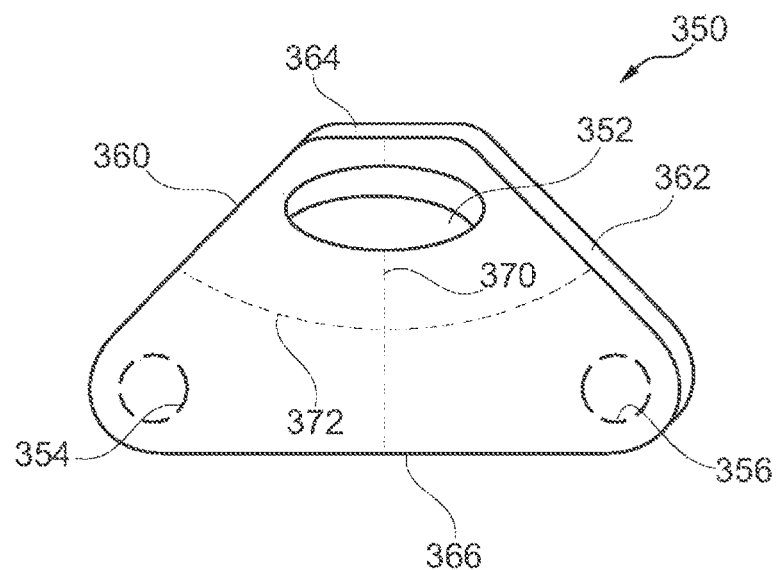
FIG. 33 is a perspective view.
Figure 34:
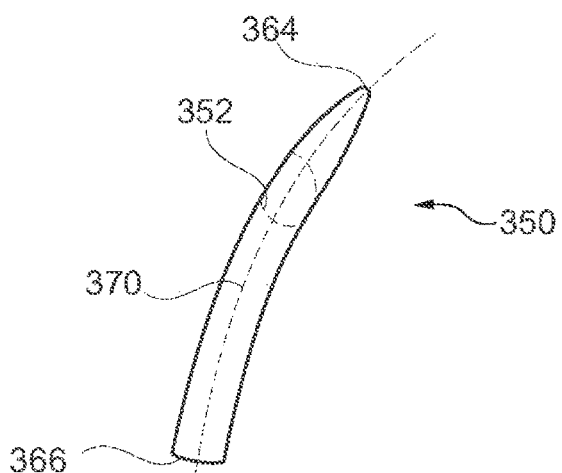
FIG. 34 is a side view.
Figure 35:
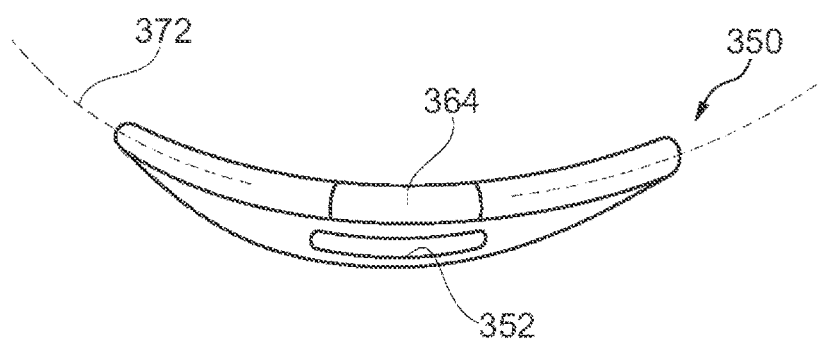
FIG. 35 is a top view of the implantable support illustrated in FIG. 32.

FIG. 33 is a perspective view, FIG. 34 is a side view, and FIG. 35 is a top view of the implantable support 350 illustrated in FIG. 32. The implantable support 350 has a longitudinal curvature 370 from the top side 364 to the lower side 366 and a lateral curvature 372 between the sides 360, 362. The longitudinal curvature 370 and the lateral curvature 372 are convex on the anterior, outer surface of the support 350, such that the interior, posterior side of the support 350 is concave. The relative angles of the sides 360, 362, in combination with the curvatures 370, 372 configure the support 350 to form an artificial crus penis recess that projects in an anterior direction from the pelvis. The artificial crus penis recess provides the trans-male with a structure that will support a neopenis and allows the receptacle 352 to locate the prosthetic anatomically in a natal penis location. The complex curvature (longitudinal and lateral) of the support 350 provides a shield shape that allows the support 350 to provide a foundation that supports penetrative intercourse with the prosthetic(s) of the neopenis.

The implantable support 350 is suitably fabricated from polymer, such as polypropylene, reinforced polypropylene, nylon, a carbon fiber reinforced polymer, or metal, such as stainless steel.

When implanted, and connected to the pelvis, the receptacle 352 of the support 350 functions as a crus penis and receives the proximal end portion of the penile prosthetic, the connector 354 secures the proximal end of one of the right-hand prosthetic, and the connector 356 secures the proximal end of the left-hand prosthetic. The proximal portions of the prosthetics will be aligned along the descending ramus and the distal end portions of the prosthetics will be received within the neophallus. This orientation will locate the prosthetics within the neophallus anatomically in a natal penis location.

Some prosthetics are slightly shorter in length than desired by the surgeon for the application. In such a case the surgeon will attach a rear tip extender (RTE) to the proximal end portion of the prosthetic to give the prosthetic a length suited to the individual. The connectors 354, 356 are configured to receive the RTEs, for example by mechanical attachment such as a threaded connection, or by surgical connection through suturing the RTE to the connector 354, 356 area.

Figure 36A:
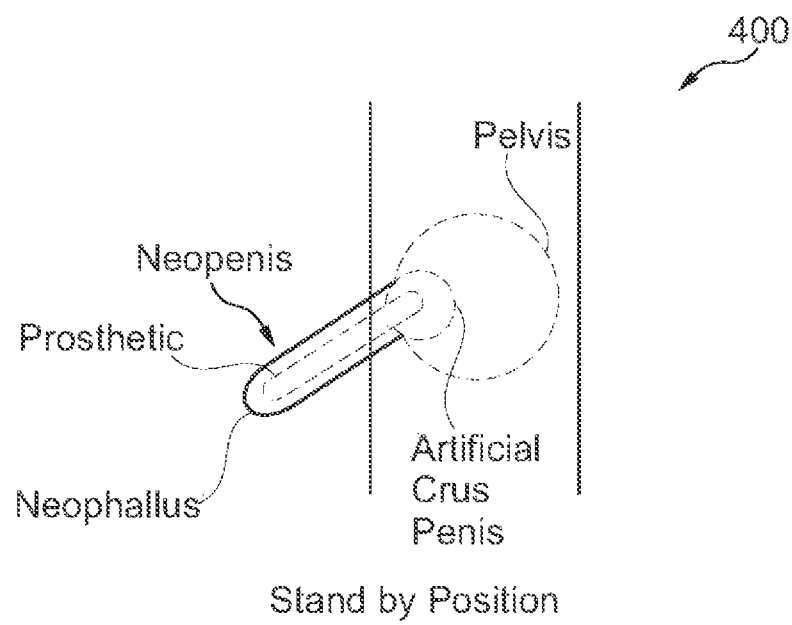
FIG. 36A is a schematic view of one embodiment of a neophallus implant system with a neopenis in a flaccid state.
Figure 36B:
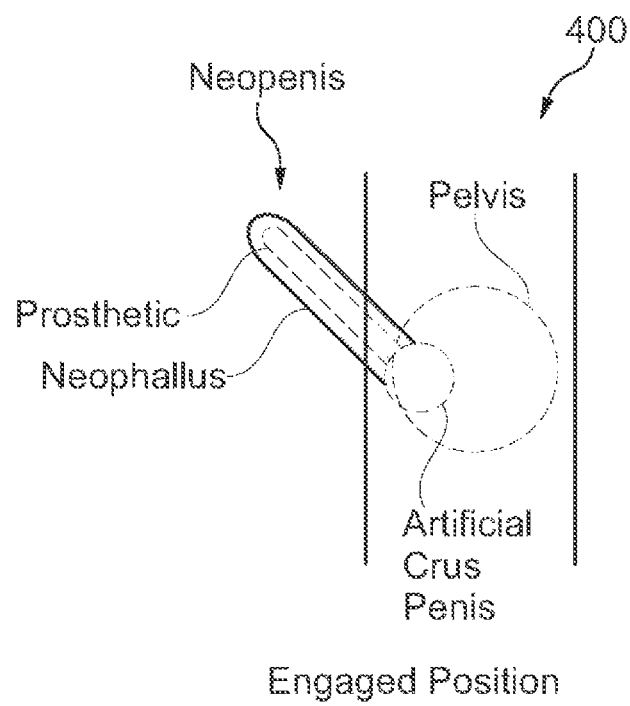
FIG. 36B is a schematic view of the neophallus implant system with the neopenis in an erect state.

FIG. 36A is a schematic view of one embodiment of a neophallus implant system 400 illustrating a neopenis in a flaccid state, and FIG. 36B is a schematic view of the neophallus implant system 400 with the neopenis in an erect state. The schematic views illustrate a prosthetic implanted into a neophallus to provide a neopenis that is supported by an artificial crus penis, such as those artificial crus penis recesses described in this application. The artificial crus penis is implanted in the pelvis and operates to allow the prosthetic to present the neophallus in both the flaccid and erect states, embodiments of which are described below.

Figure 37A:
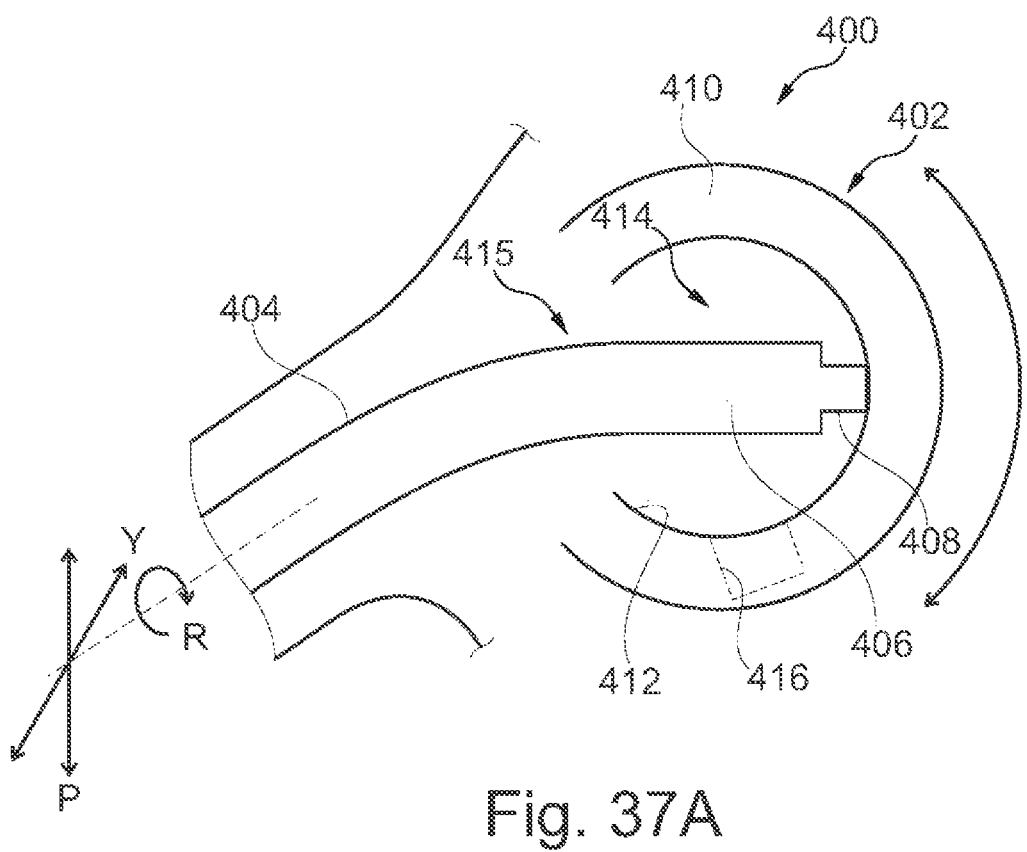
FIG. 37A-FIG. 37F are schematic views of the neophallus implant system illustrated in FIG. 36.

FIG. 37A is a side schematic view of one embodiment of the neophallus implant system 400. The system 400 includes an artificial crus penis 402 supporting a penile prosthetic 404. The neophallus has been formed from tissue and the penile prosthetic 404 has been implanted in the neophallus. The penile prosthetic 404 includes a proximal end portion 406 and a proximal end 408. The artificial crus penis 402 includes a body 410 that is implantable into the pelvis, where the body 410 includes an interior surface 412 that defines a recess 414 and an opening 415 for access to the recess 414. A keyhole opening 416 is formed in the interior surface 412 and is sized to receive the proximal end 408 of the penile prosthetic 404, when the proximal end 404 is manually oriented to a specific orientation by the user.

The penile prosthetic 404 includes several degrees of freedom, including a pitch direction P in which the penile prosthetic pitches up-and-down within the plane of the drawing, a roll direction R in which the penile prosthetic rotates about its longitudinal axis, and a yaw direction Y in which the distal end portion of the penile prosthetic 404 moves laterally into and out of the plane of the drawing.

The user of the implanted penile prosthetic 404 may move the neopenis in several directions. The user of the implanted penile prosthetic 404 may manually move the penile prosthetic 404 in certain specific directions, detail below, that ultimately engage the proximal end 408 of the penile prosthetic 404 within the keyhole opening 416 of the artificial crus penis 402 to provide the neopenis with an erection.

Figure 37B:
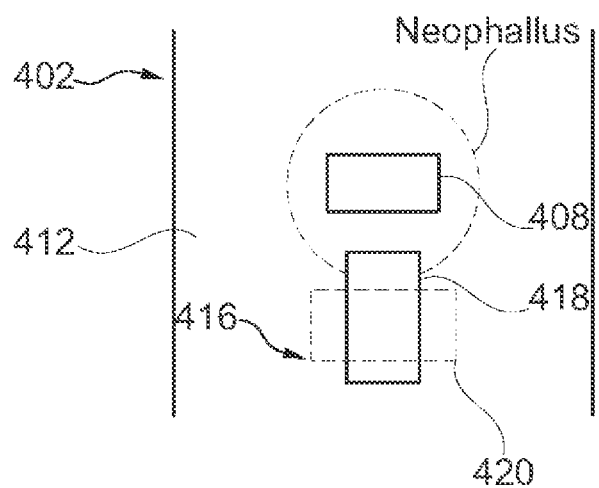

FIG. 37B illustrates the neophallus in the flaccid state with the proximal end 408 located superior relative to the keyhole opening 416. The keyhole opening 416 includes a gate 418 and a fence 420. The gate 418 is a vertical orientation, and the fence 420 has a horizontal orientation. The fence 420 is formed as an opening in the interior surface 412 in a location that is posterior to the gate 418. As described above, the penile prosthetic 404 is movable relative to the interior surface 412. The proximal end 408 of the penile prosthetic 404 may move over the keyhole opening 416 and will not engage with the gate 418 until the proximal end 408 also has a vertical orientation that matches with the orientation of the gate 418.

Figure 37C:
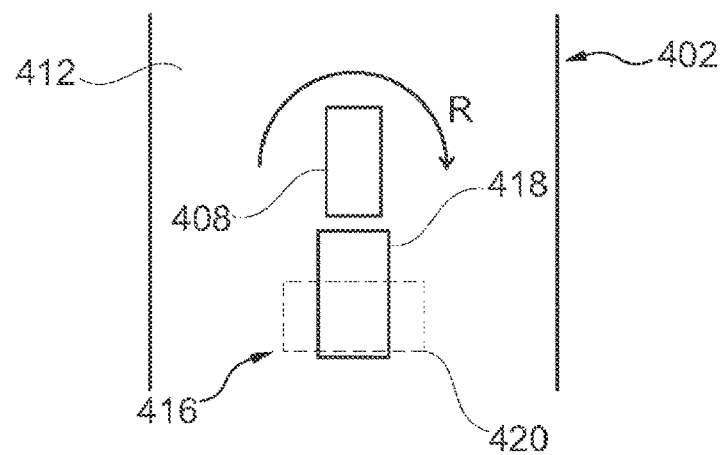

FIG. 37C illustrates the proximal end 408 of the penile prosthetic has been rotated in the roll direction R on its longitudinal axis to orient the proximal end 408 in a vertical orientation that is aligned with the gate 418. Subsequent movement of the proximal end 408 along the interior surface 412 will seat the proximal end 408 into the gate 418.

Figure 37D:
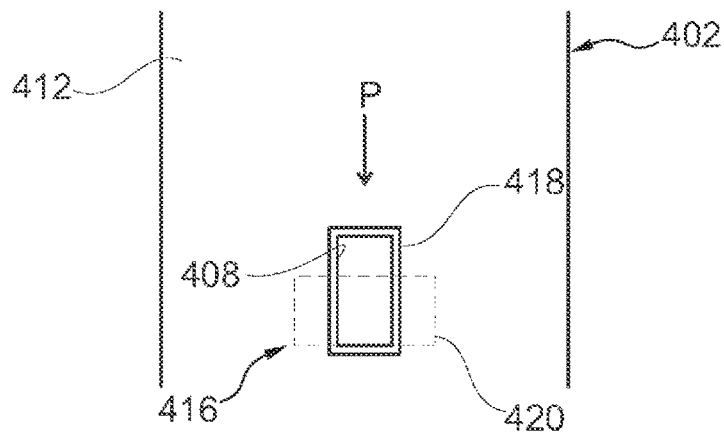

FIG. 37D illustrates the proximal end 408 has been translated and moved down along the interior surface 412 until the proximal end 408 has been seated within the gate 418 of the artificial crus penis 402. Additional movement in a proximal direction will push the proximal end 408 into and through the gate 418.

Figure 37E:
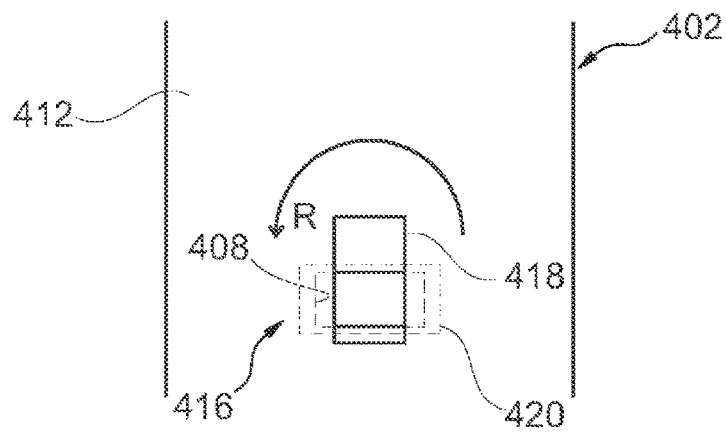

FIG. 37E illustrates that the proximal end 408 has been inserted into the gate 418. The proximal end 408 has been moved into the plane of the drawing, through the gate 418, until the proximal end 408 has dropped into the fence 420. Rotation of the proximal end 408 to the horizontal orientation aligns the proximal end 408 within the fence 420 to effectively "lock" the proximal end 408 of the penile prosthetic into the keyhole opening 416 of the artificial crus penis 402.

Figure 37F:
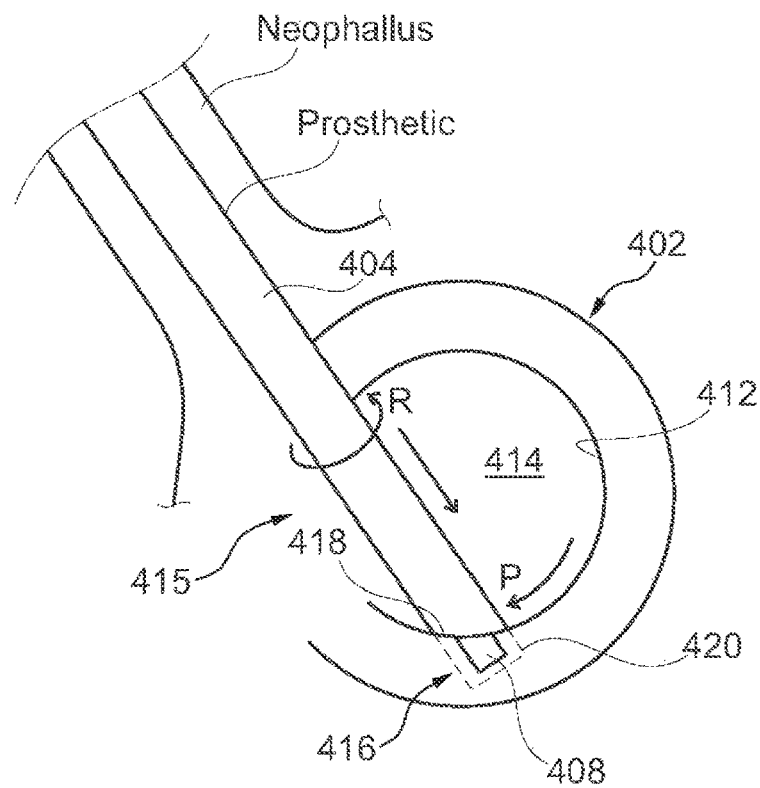

FIG. 37F is a schematic illustration of the movement of the penile prosthetic 404 relative to the artificial crus penis 402. The penile prosthetic 404 has been moved in the pitch direction P such that the proximal end 408 has slid along the interior surface 412 to the gate 418. The penile prosthetic 404 has been rotated in the roll direction R counter-clockwise until the proximal end 408 aligned with the gate 418. Additional movement of the proximal end 408 in a proximal direction moves the proximal end 408 through the gate 418. The penile prosthetic 404 has been rotated clockwise until the proximal end 408 aligns with and engages with the fence 420. The configuration illustrated in FIG. 37F maintains the neopenis in an erect state that is suitable for penetrative intercourse.

Figure 38:
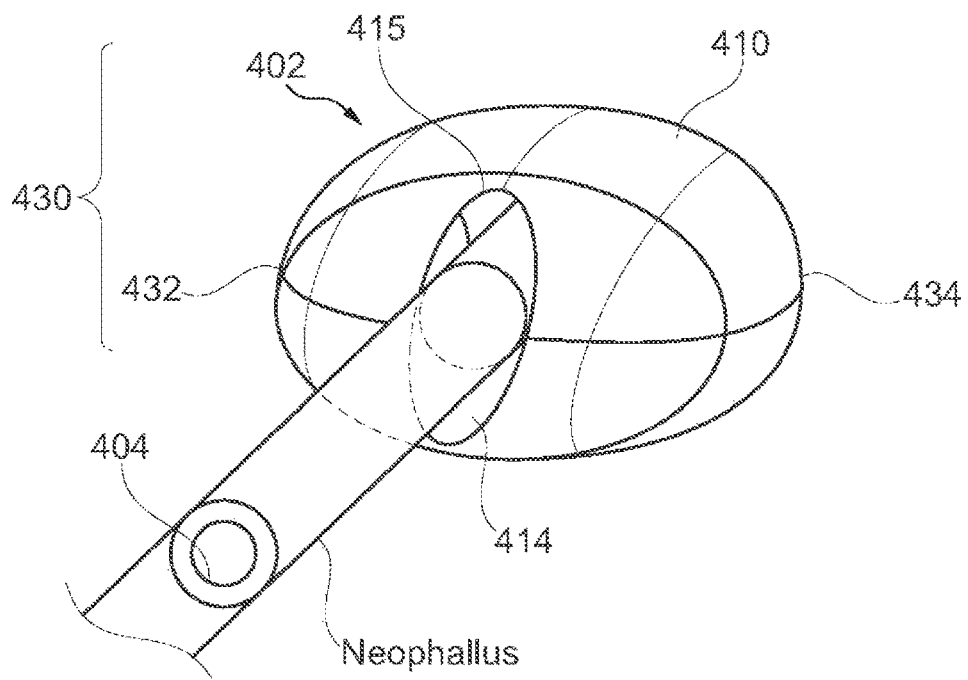
FIG. 38 is a perspective view of one embodiment of a neophallus implant system.

FIG. 38 is a perspective view of one embodiment of an implantable support 430 including one embodiment of the artificial crus penis 402. The body 410 of the implantable support 430 includes a first side 432 that is attachable to a right side ramus and a second side 434 that is attachable to a left side ramus of the patient. The body 410 is oval in both lateral and longitudinal cross-section with smoothly curved sides. The opening 415 is formed in an anterior surface of the body 410, and the penile prosthetic 404 projects in a proximal direction through the opening 415 into the recess 414 of the artificial crus penis 402.

The implantable support 430 is suitably fabricated from polymer, such as polypropylene, reinforced polypropylene, nylon, a carbon fiber reinforced polymer, or metal, such as stainless steel.

Implantation of the implantable support 430 across the ramus bones and inferior relative to the pubic bone provides the patient with a support that is adapted to support a neopenis anatomically in a natal penis position that is suitable for penetrative intercourse.

Figure 39A:
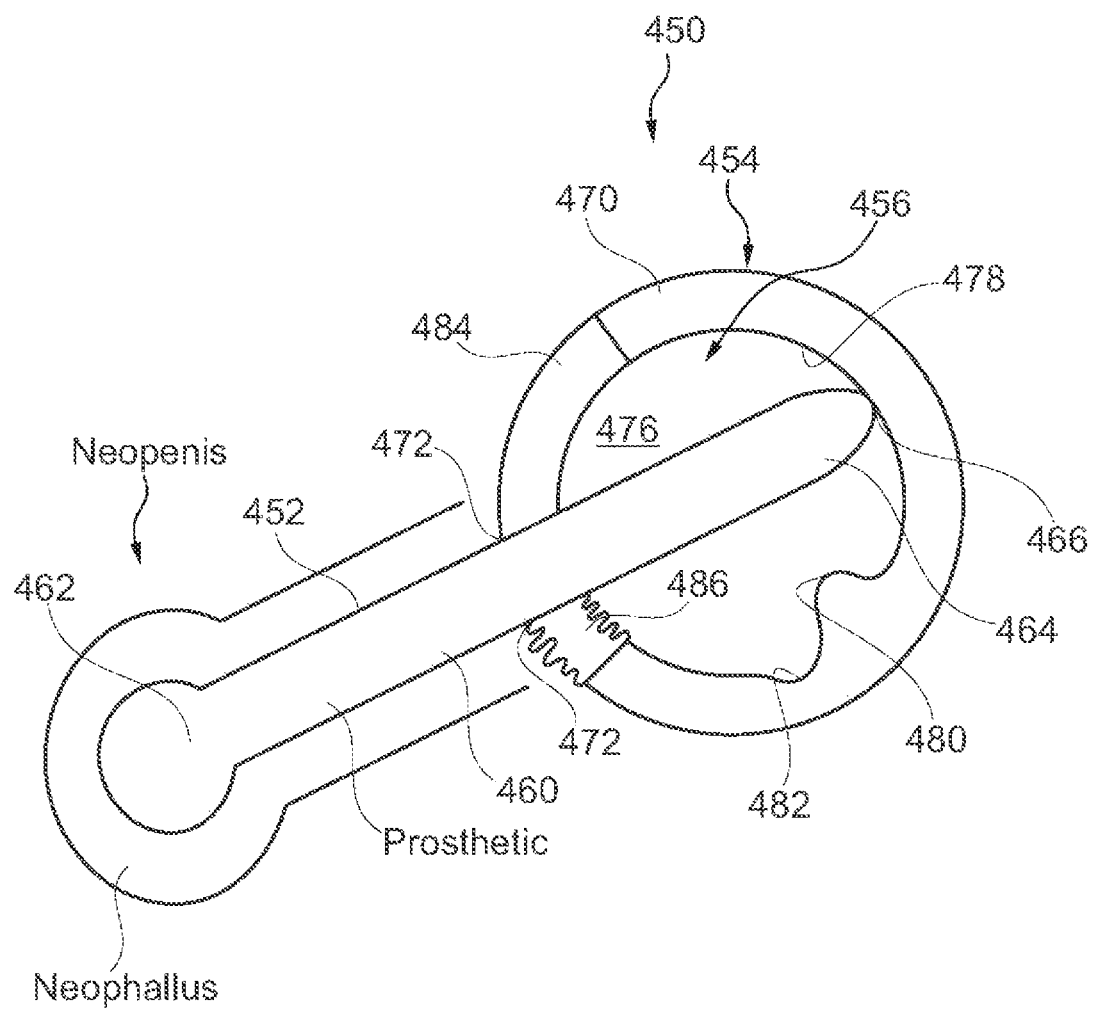
FIG. 39A is a schematic view of one embodiment of a neophallus implant system with a neopenis in a flaccid state.
Figure 39B:
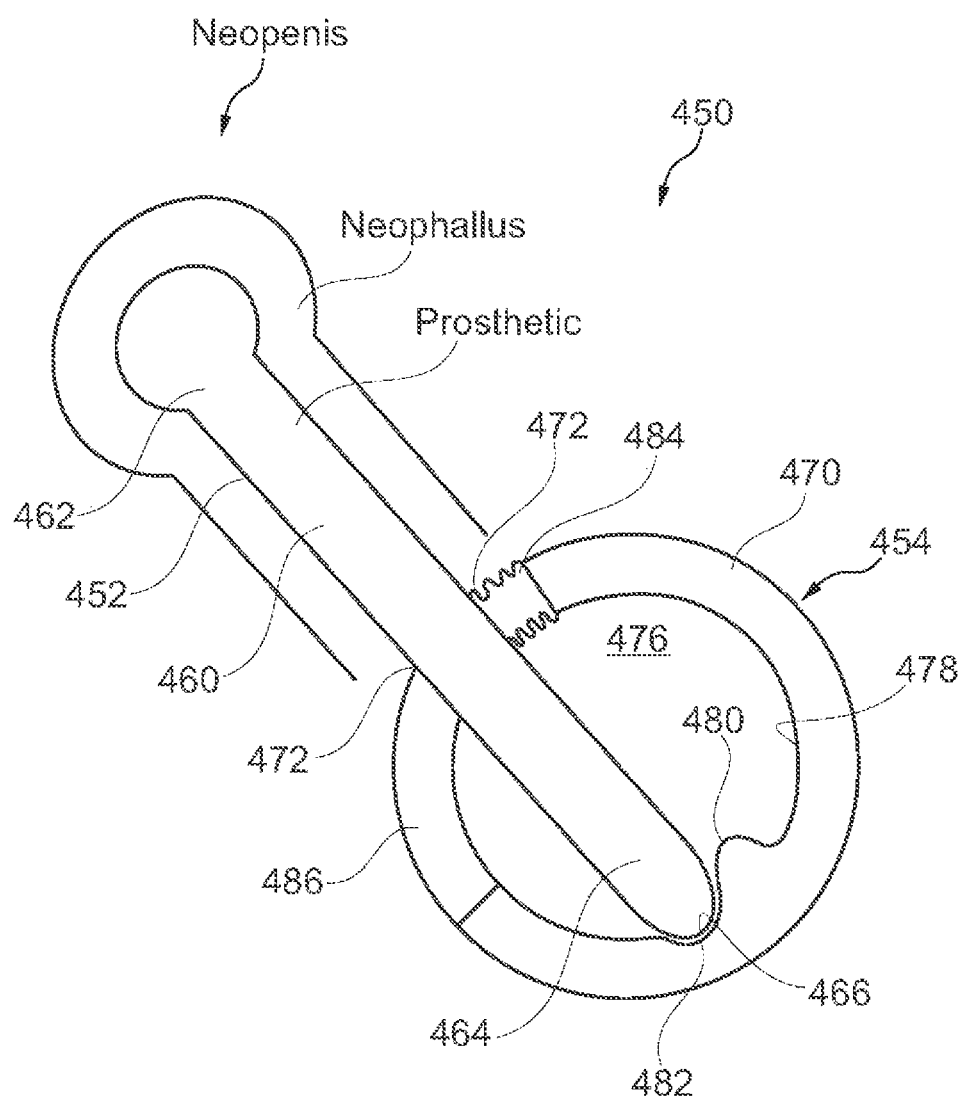
FIG. 39B is a schematic view of the neophallus implant system with the neopenis in an erect state.

FIG. 39A is a side schematic view of a neophallus implant system 450 illustrating a neopenis in a flaccid state, and FIG. 39B is a side schematic view illustrating the neopenis in an erect state.

The neophallus implant system 450 includes a penile prosthetic 452 and an implantable support 454 that is attachable to a descending ramus of a pelvis to provide an artificial crus penis 456 for a patient receiving a neopenis. The implantable support 454 is adapted to resist axial forces experienced by the penile prosthetic 452 during penetrative intercourse, to thus form supporting structure that is provided by the crus penis in the natal male.

The penile prosthetic 452 has a shaft 460 connected between a distal end portion 462 and a proximal end portion 464 that terminates in a proximal end 466. The distal end portion 462 is implantable into a neophallus to provide the user with a neopenis capable of achieving an erection suitable for penetrative intercourse.

In one embodiment, the artificial crus penis 456 of the implantable support 454 includes a receptacle 470 providing an opening 472 into a recess 476. The recess 476 is defined by an interior surface 478 and includes a ridge 480 formed inside of the receptacle 470, where the ridge 480 projects away from the interior surface 478. In one embodiment, the interior surface 478 is smooth and defines an arc of a constant radius between the ridge 480 and the opening 472 in an area that is superior to (counter-clockwise) the ridge 480. In one embodiment, the interior surface 178 includes a well 482 that is inferior to (clockwise) the ridge 480, such that the interior surface 478 does not have a constant radius between the ridge 480 and the opening 472 and an area that is under (or inferior) to the ridge 480.

The artificial crus penis 456 is configured to operate such that, when the proximal end 466 of the penile prosthetic 452 is superior to the ridge 480, the neophallus is in a flaccid state (FIG. 39A). Alternatively, the artificial crus penis 456 is configured to operate such that, when the proximal end 466 of the penile prosthetic 452 is inferior to the ridge 480, the penile prosthetic and the neophallus are maintained in an erect state (FIG. 39B) that adapts the neopenis for penetrative intercourse.

The penile prosthetic 452 is movable between the down position (flaccid state) in which the proximal end 466 is superior to the ridge 480, and the up position (erect state) in which the proximal end 466 is inferior to the ridge 480 and seated within the well 482. In one embodiment, the penile prosthetic 452 is provided as a single shaft that is implanted into a neophallus. An optional embodiment includes providing a dual shaft penile prosthetic 452. The recess 476 is filled, preferably with a gel or a high viscosity liquid that dampens rapid movement of the prosthetic 452 to ensure the prosthetic 452 moves in an anatomically natural manner. The implant system 450 is configured to allow the patient to grasp the shaft 460 within the neopenis and move it from a first desired erect position to an optionally desired flaccid position. The implantable support 454 is adapted to resist the pressures created in those common angles, or orientations, that are associated with penetrative intercourse. The interior surface 478 of the artificial crus penis 456 is suitable for providing multiple locked, or engaged, erect state positions. In one embodiment, the motion to facilitate movement of the penile prosthetic 452 between the flaccid position and the erect position includes a rotational movement of the shaft 460. In one embodiment, an asymmetrical configuration of the interior surface 478 allows the user to move the shaft 460 variety of selected positions. In one embodiment, the proximal end portion 464 of the shaft 460 includes a spring that is adapted to bias the proximal end portion 464 relative to the interior surface 478 of the artificial crus penis receptacle 456 to allow the shaft 460 to compress when moving over the ridge 480 and extend into engagement with the well 482.

In one embodiment, an exterior surface of the artificial crus penis receptacle 456 includes a material that promotes tissue ingrowth or a textured surface adapted to maintain the position of the implant relative to the pelvic structure.

It is desirable to seal the recess 476 from the possibility of undesirable tissue growth into of the implantable support 454. In one embodiment, a first seal 484 is provided in a superior location between the receptacle 470 and the penile prosthetic 452, and a second seal 486 is provided in an inferior location between the receptacle 470 and penile prosthetic 452. The first seal 484 and the second seal 486 are flexible, elastic, and adapted to stretch as the penile prosthetic 452 moves within the opening 472. Suitable materials for the seals 484, 486 include silicone or another suitable elastomer.

The penile prosthetic 452 is connected to the seals 484, 486, with the proximal end portion 464 retained in the recess 476, which configures the prosthetic 452 to pivot relative to the receptacle 470.

FIG. 39A illustrates the penile prosthetic 452 in a flaccid position in which the second seal 486 is compressed and the first seal 484 is elongated (or, in tension). FIG. 39B illustrates the penile prosthetic 452 in an erect position in which the first seal 484 is compressed and the second seal 486 is elongated. The seals 484, 486 seal against the penile prosthetic 452 and the receptacle 470 to reduce the likelihood that tissue will enter and grow within the recess 476 and to prevent the gel or high viscosity liquid (provided to dampen the movement of the prosthetic 452) from escaping the recess 476.

Various advantages of the implantable system 450 include a specific design for trans-gender use, a design that is not reliant on the corpora cavernosa that are present in the natal male anatomy and not present in the trans-male pelvis, a design that obviates a reservoir to contain liquid and a pump to move the liquid, and a design that is compatible for use with those who have limited hand dexterity.

Figure 40:
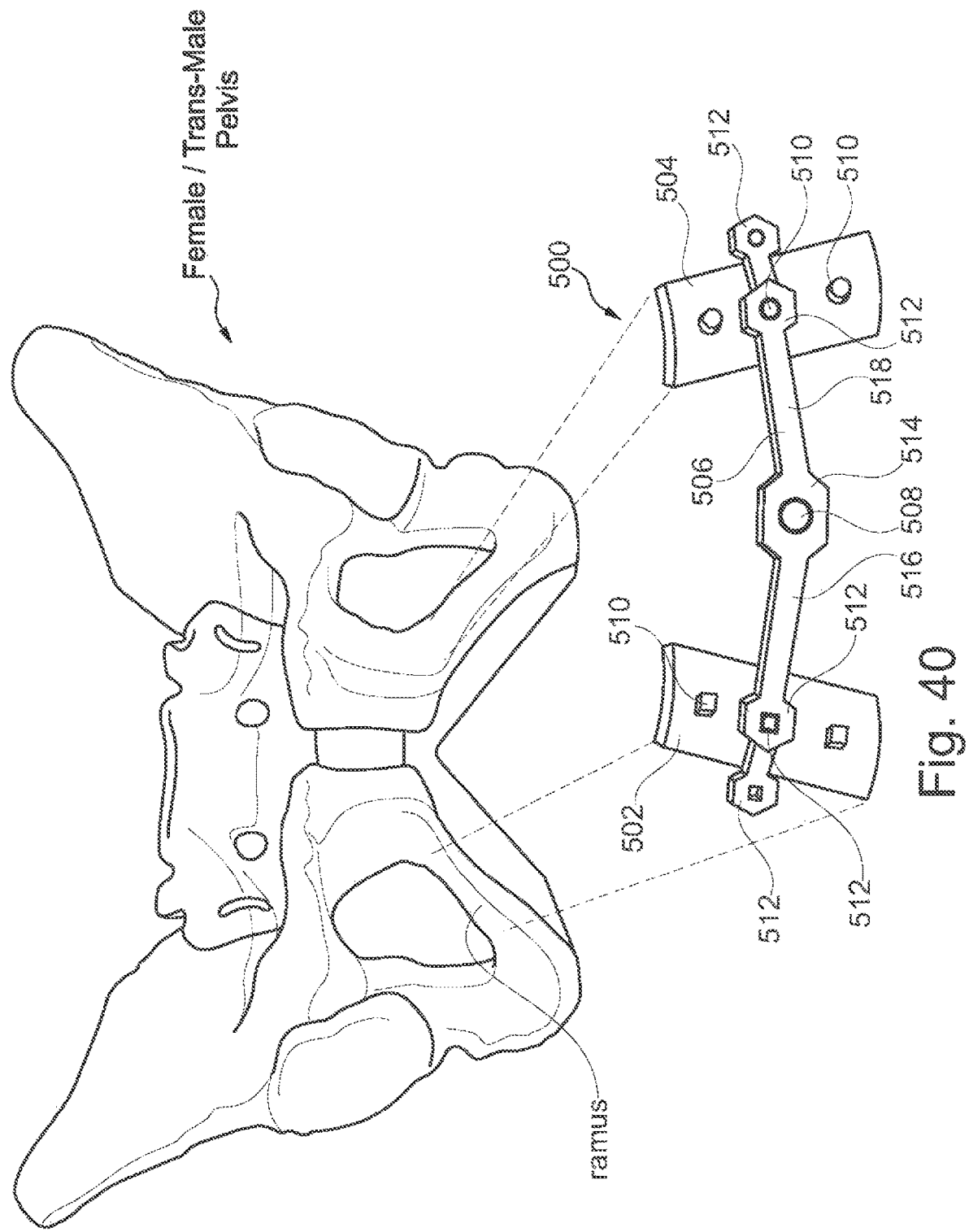
FIG. 40 is a perspective view of one embodiment of an implantable support relative to a trans-male pelvis.

FIG. 40 is a perspective view of one embodiment of an implantable support 500 attachable to a female pelvis that has been surgically prepared as a trans-male pelvis. The support 500 includes a first plate 502, a second plate 504, and a bridge 506 attachable to and extends will between the first plate 502 and the second plate 504. The bridge 506 includes a receptacle 508 that is adapted to receive a proximal end portion of a penile prosthetic. Thus, in one embodiment the receptacle 508 provides an artificial crus penis recess that is adapted to receive and support a penile prosthetic that is implantable into the trans-male.

The first plate 502 is attachable to the trans-male pelvis, for example to the right side descending ramus, and the second plate 504 is attachable to the trans-male pelvis, for example to the left side descending ramus. The first plate 502 and the second plate 504 are attachable to the bone of the pelvis through bonding with bone putty or bone cement, through mechanical attachment with screws, or by biological bonding in which tissue is encouraged to grow into or onto a surface of one of the plates, or a combination of these attachment approaches. In one embodiment, a surface of the plate 502 that is placed in contact with the ramus includes a set of barbs or other projections that will secure the plate 502 to the bone of the pelvis. The first plate 502 and the second plate 504 are suitably fabricated from a polymer, such as polypropylene or silicone, a metal such as stainless steel, or a composite structure. The first plate 502 and the second plate 504 are each provided with multiple attachment locations 510, where the attachment locations 510 include a projection sized to receive the bridge 506 or a recess sized to receive a projection projecting from the bridge 506. The multiple attachment locations 510 provide the surgeon with options for placement of the bridge 506 to allow the implantation of the penile prosthetic to mirror a natal male orientation.

The bridge 506 include multiple plug sites 512 that are adapted to engage with the multiple attachment locations 510. The multiple plug sites 512 provide the surgeon with adjustable fixation options when implanting the support 500. In one embodiment, the bridge 506 is adapted to allow the surgeon to cut off or remove one or more of the superfluous multiple plug sites 512 after attachment of the bridge 506 to the first plate 502 and the second plate 504.

The bridge 506 includes a socket 514 secured between a first arm 516 and a second arm 518. In one embodiment, the receptacle 508 is a tapered conical receptacle formed through a thickness of the socket 514. The multiple plug sites 512 are provided incrementally along each of the arms 516, 518. The bridge 506 is suitably fabricated from a polymer, such as polypropylene, nylon, silicone, or metal such as stainless steel.

Figure 41:
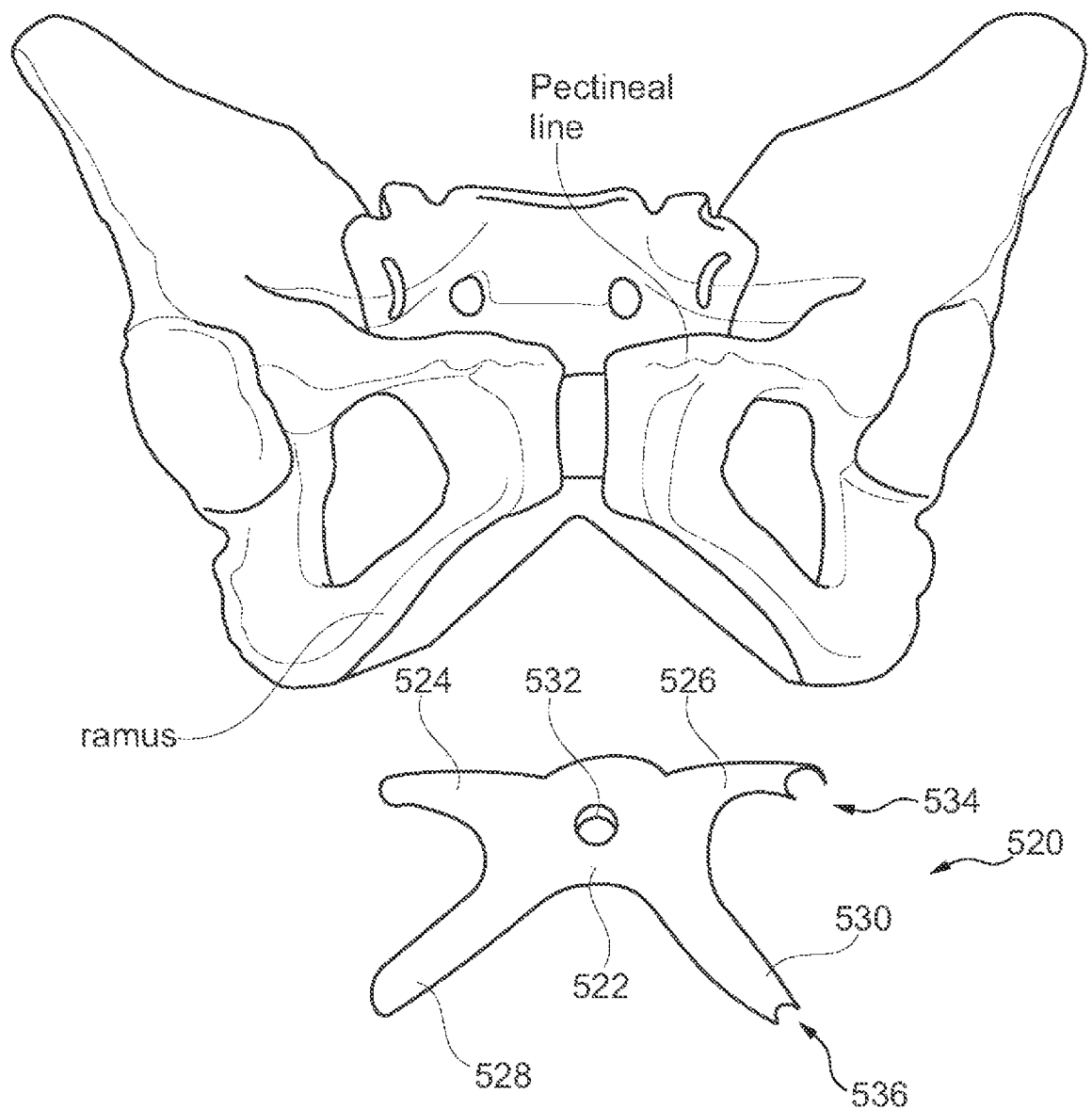
FIG. 41 is a perspective view of one embodiment of an implantable support relative to a trans-male pelvis.

FIG. 41 is a front view of one embodiment of an implantable support 520. The implantable support 520 is implantable on the trans-male pelvis to support an implanted penile prosthetic in a natal male orientation. The implantable support includes a penile crus plate 522, a pair of arms 524, 526 extending from the penile crus plate 522, and a pair of ramus legs 528, 530 extending from the penile crus plate 522. The penile crus plate 522 includes a receptacle 532 that provides an artificial crus penis recess that is adapted to receive and support the implanted penile prosthetic of a trans-male phalloplasty. The pair of arms 524, 526 are adapted for attachment to the pectineal line of the pelvis on either side of the pubic symphysis. In one embodiment, each of the pair of arms 524, 526 includes a back plate that is adapted to receive a bone screw for attachment of the arms 524, 526 to a posterior side of the pectineal line. In one embodiment, each of the arms 524, 526 is provided with a curved clamp profile 534 that adapts the arms 524, 526 for attachment to the pectineal line. The pair of ramus legs 528, 530 are adapted for attachment to the anterior surface of the descending pubic ramus. In one embodiment, each of the pair of ramus legs 528, 530 are configured as a curved clamp 536 that is adapted to be clamped around a portion of the descending pubic ramus to securely hold the implantable support 520 relative to the pelvis such that the implanted penile prosthetic is oriented in a natal male position. The implantable support 520 offers a level of flexibility to the surgeon for location of a proximal end of a penile prosthetic at or below the pubic bone of the pelvis. The implantable support 520 is adapted to mount on the anterior service of the pelvis, anterior to the pubic symphysis. The implantable support 520 is secured to, or around, at least one of the pectineal line for the descending pubic ramus to provide a very secure mount for the proximal portion of the implantable penile prosthetic.

Figure 42:
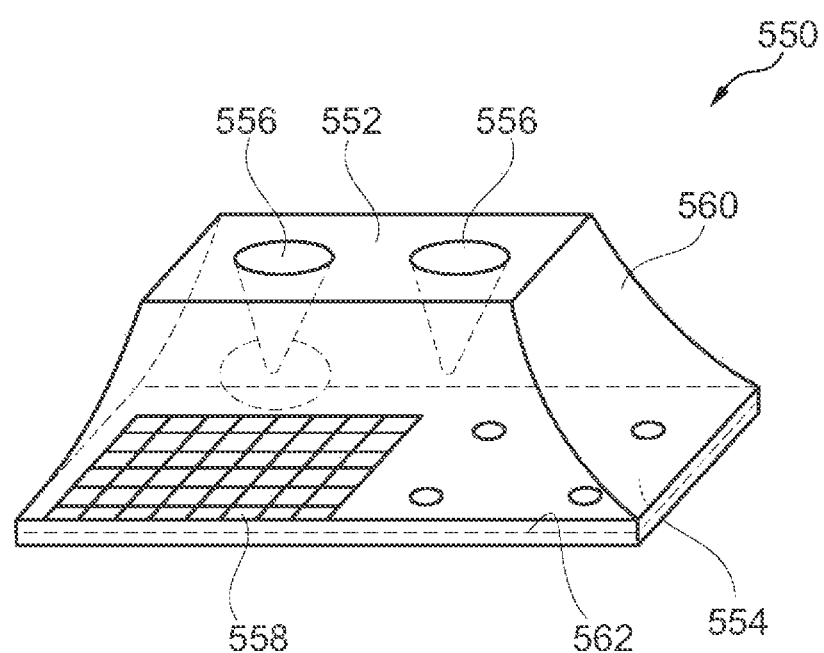
FIG. 42 is a perspective view of one embodiment of an implantable support adapted to receive proximal end portions of a penile prosthetic during a phalloplasty procedure.

FIG. 42 is a perspective view of one embodiment of the implantable support 550. The implantable support 550 includes an anterior face 552 opposite a posterior face 554 and a pair of receptacles 556 formed in the anterior face 552. The pair of receptacles 556 provide a pair of artificial crus penis recesses that are adapted to receive a proximal portion of an implantable penile prosthetic. The implantable support 550 is attachable to a surgically altered trans-male pelvis to provide the trans-male with a support that will maintain a penile prosthetic and a natal male orientation that allows penetrative intercourse. One advantage of the implantable support 550 is that each of receptacles 556 is adapted to receive a proximal end of an implantable penile prosthetic of the style that is implantable into a natal male, where one example of the implantable penile prosthetic is the TITAN® penile prosthetic available from Coloplast Corp., Minneapolis, Minn. Thus, the implantable support 550 is compatible with the currently available penile prosthetics.

In one embodiment, at least a portion of the posterior face 554 includes a mesh grid 558 that is adapted to allow tissue ingrowth into a portion of the implantable support 550. In one embodiment, the implantable support 550 includes a body 560 integrating a stainless steel plate 562, where the stainless steel plate 562 provides a level of rigidity for attachment of the implantable support 550 to the trans-male pelvis. The body 560 is suitably fabricated from a flexible polymer, such as silicone. The mesh grid 558 is applied to a posterior side of the body 562 encouraged tissue ingrowth into the other components of the implantable support 550.

Figure 43:
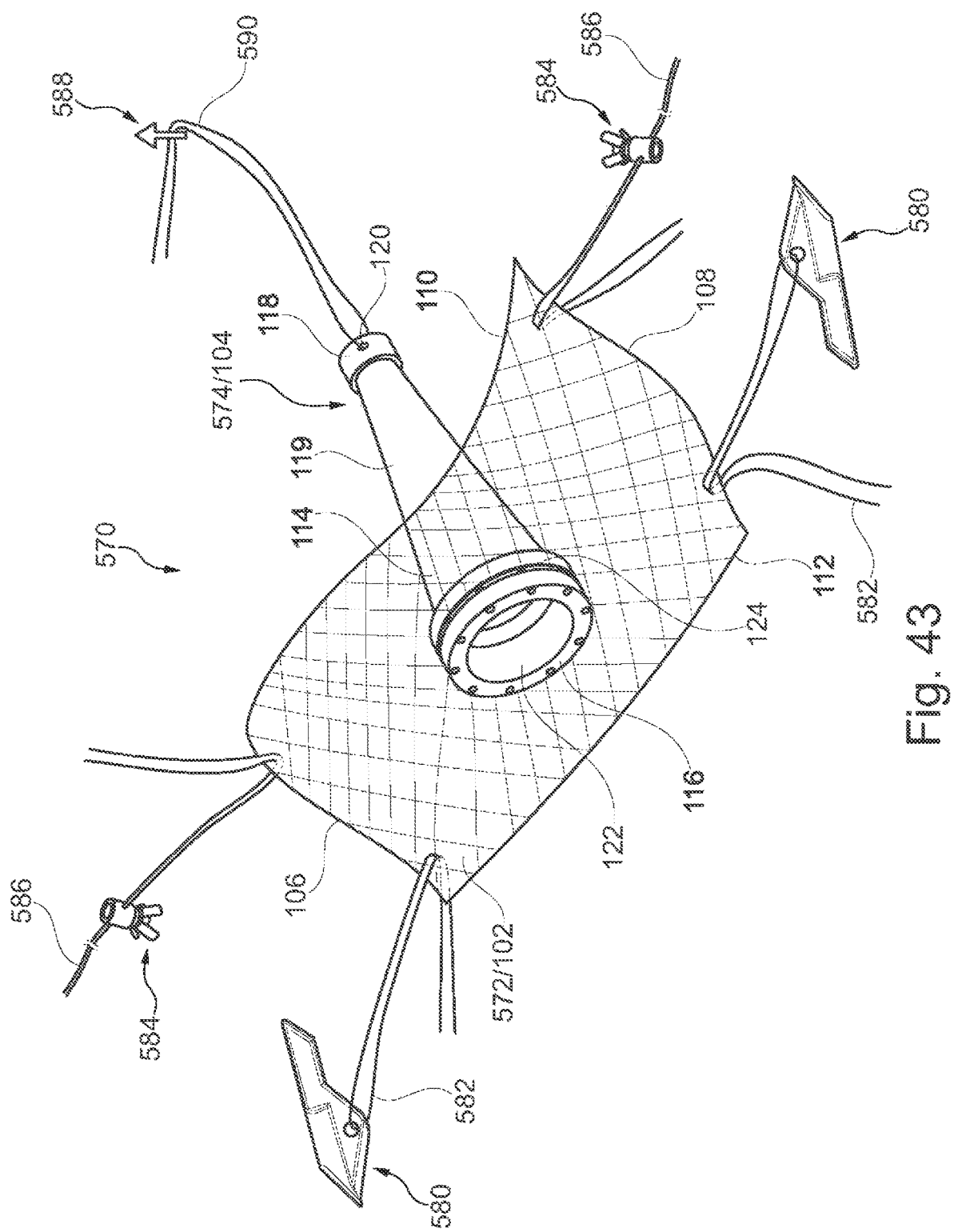
FIG. 43 is a perspective view of one embodiment of an implantable support including a plurality of tissue anchors and an artificial crus penis recess.

FIG. 43 is a perspective view of one embodiment of an implantable support 570 having attachment features that allow fixation of the support 570 to ligaments and tissue of the pelvis, for example the sacrospinous ligament or tissue of the sacrum. The implantable support 570 is analogous to the implantable support 100 described in FIG. 12 and includes a base 572/102 that is attachable to a pelvis of a person assigned the female sex at birth, and an artificial crus penis recess 574/104 connected to the base 572/102. The base 572/102 provides an implant bed that supports the artificial crus penis recess 574/104 to allow a person who was assigned the female sex at birth to have a neopenis that is situated anatomically in the same position as a natal penis. The base 572/102 and the artificial crus penis recess 574/104 share those aspects of the implantable support 100 described in FIG. 12, and thus include common identifying numbers.

The attachment features of the support 570 include anchors that are secured to the base 572 with the suture. A variety of such anchors are illustrated, including anchors that allow the suture to slide relative to the anchor, anchors that toggle to engage with tissue, and push through anchors that are suitable for insertion into tissue such as ligaments that are out of the line of sight of the surgeon. The illustrated anchors are exemplary embodiments. In one embodiment, a set of toggling anchors 580 is attached to the base 572 by sutures 582, and a set of adjustable sliding anchors 584 are attached to the base 572 with separate sutures 586.

The toggling anchors 580 are as described in U.S. Pat. Appln. Pub. 2016/0157845, which issued as U.S. Pat. No. 9,510,822, the disclosure of which is incorporated by reference in its entirety into this application.

The adjustable sliding anchors 584 are as described in U.S. Pat. Appln. Pub. 2010/0198003, which issued as U.S. Pat. No. 8,585,578, the disclosure of which is incorporated by reference in its entirety into this application.

In one embodiment, the support 570 is secured to the patient by attaching one or more anchors to the sacrum and two or more anchors to the tissue of the obturator foramen. In one embodiment, the support 570 is secured to the patient by attaching one or more anchors to the sacrospinous ligament and one or more anchors at or near the tissue of the obturator foramen.

The surgeon may find it useful to insert the toggling anchors 580 into tissue associated with the obturator foramen, and employ the sutures 582 to adjust the tension between the anchor 580 and the base 572. In this sense, the lateral edge 112 would be an inferior edge, or bottom, of the base 572. The surgeon may find it useful to insert the adjustable sliding anchors 584 into a ligament, such as a sacrospinous ligament, and employ the suture 586 to adjust the tension between the anchor 584 and the base 572. The artificial crus penis recess 574 supports a portion of the implantable penile prosthetic and optionally includes a push through anchor 588 secured to the base 572 by a suture 590. It is acceptable to insert the adjustable sliding anchors 584 into tissue of the obturator foramen, and insert the toggling anchors 580 into perineum tissue covering the bone of the pelvis or into a ligament within the pelvis. The push through anchor 588 provides additional support to the proximal end of the artificial crus penis recess 574. This approach to fixation of a penile prosthetic in the trans-male pelvis advantageously employs landmarks that are familiar to the surgeons who implant supports to treat pelvic organ prolapse in the natal female. The multiple fixation points provided by the multiple anchors 580, 584, 588 and the base 572 provided durable and flexible fixation that adapts the support 570 to withstand the axial forces associated with penetrative intercourse.

Figure 44:
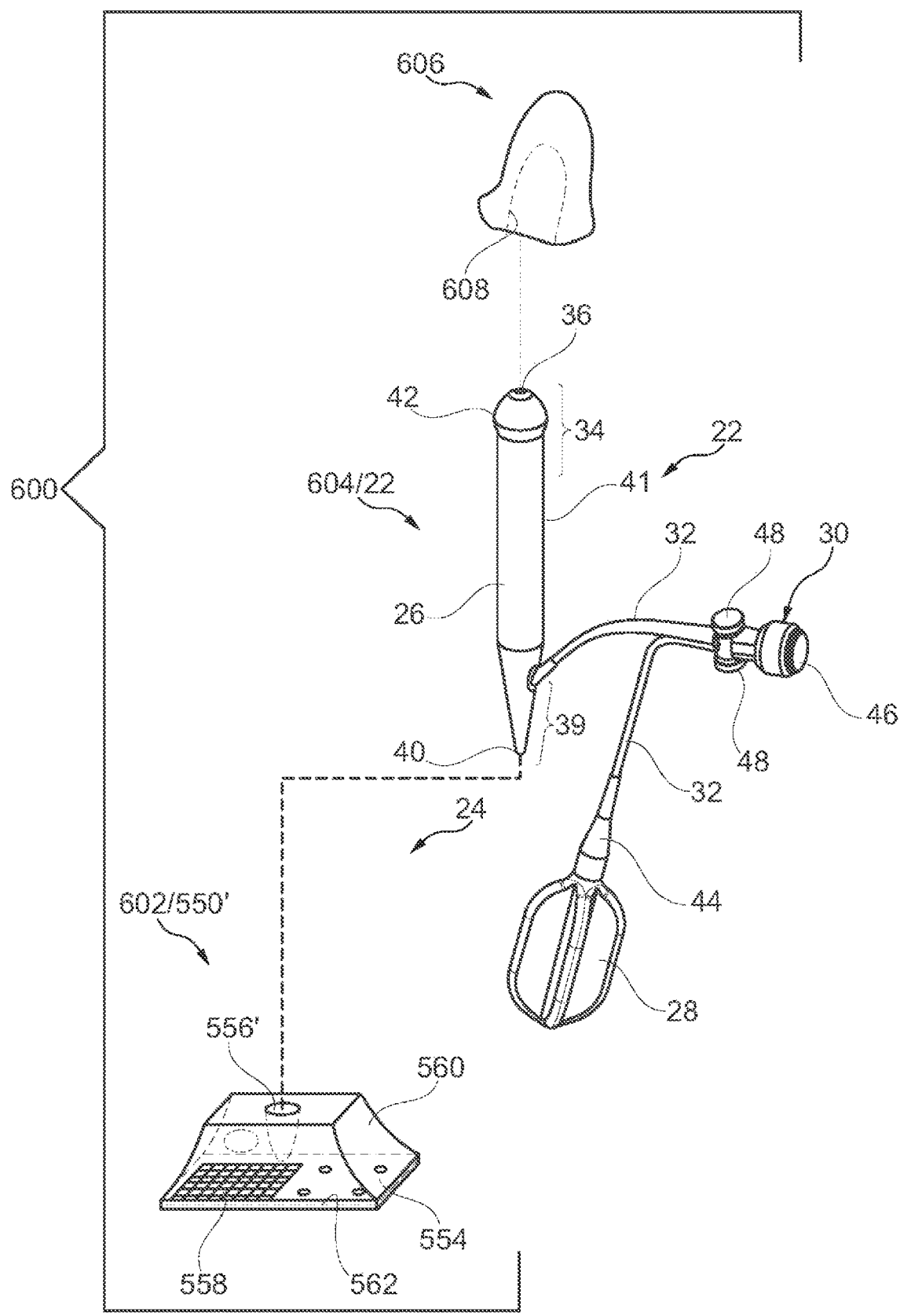
FIG. 44 is a schematic view of one embodiment of a kit of parts including a single penile prosthetic implantable in a neophallus of a trans-male pelvis during a female-to-male (FTM) phalloplasty procedure.

FIG. 44 is a perspective view of one embodiment of a kit of parts 600. The kit of parts 600 includes an implantable support 602, an implantable penile prosthetic 604, and an artificial glans 606. In one embodiment, the implantable support 602 is similar to the implantable support 550 (FIG. 42), although modified to have a single artificial crus receptacle 556'. The implantable support 602 is adapted to support the implantable penile prosthetic 604/22 in the pelvis of a trans-male in an orientation of that of a natal male penis. In one embodiment, the implantable penile prosthetic 604 is similar to the single cylinder implantable penile prosthetic 22 (FIG. 3). The artificial glans 606 is attachable to the distal end portion 34 of the implantable penile prosthetic 604/22. The artificial glans 606 is a synthetic cap portion that is attachable over the distal end 36 of the implantable penile prosthetic 604/22 inside the distal portion of the neophallus. The kit of parts 600 is supplied to a surgeon in a single, sterile package that provides the healthcare facility with components that are suited to implant and support a penile prosthetic in a trans-male after a phalloplasty procedure.

The single shaft 41 of the implantable penile prosthetic 604/22 is inflatable with liquid retained in the reservoir 28. The proximal end portion 38 of the penile prosthetic 604/22 is sized for insertion into the artificial crus penis receptacle 556' of the implantable support 602. The distal end portion 34 of the implantable penile prosthetic 604/22 is sized for insertion into a mating recess 608 formed within the artificial glans 606. The implantable penile prosthetic 604/22 and the artificial glans 606 are adapted for implantation into a surgically formed neophallus after the newly formed neophallus has healed.

Figure 45:
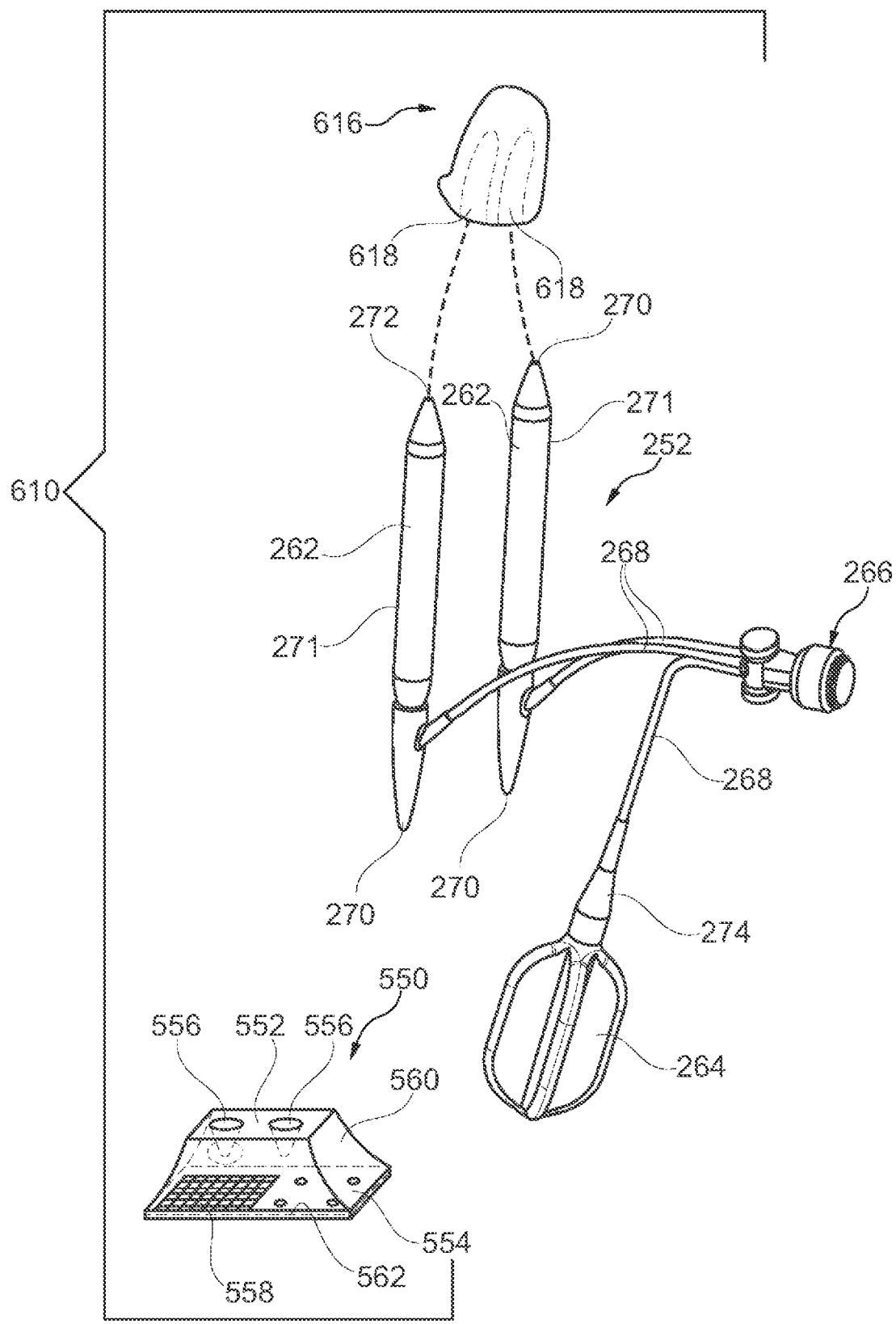
FIG. 45 is a schematic view of one embodiment of a kit of parts including dual, inflatable penile prosthetics implantable in a neophallus of a trans-male pelvis during a FTM phalloplasty procedure.

FIG. 45 is a perspective view of one embodiment of a kit of parts 610. The kit of parts 610 includes an implantable support 550 (see FIG. 42), an implantable penile prosthetic 252 including two inflatable cylinders 271 (see FIG. 27), and an artificial glans 616. The implantable support 550 is adapted to support the implantable penile prosthetic 252 in the pelvis of a trans-male in an orientation of the natal male. The implantable penile prosthetic 252 includes dual inflatable cylinders 271, each having a proximal end 270 that is sized for insertion into one of the artificial crus penis receptacles 556, and a distal end 272 that is sized for insertion into mating recesses 618 of the artificial glans 616. One suitable implantable penile prosthetic 252 is the TITAN® penile prosthetic available from Coloplast Corp., Minneapolis, Minn. The kit of parts 610 is supplied to a surgeon in a single, sterile package that provides a healthcare facility with components that are suited to implant and support a dual cylinder penile prosthetic and a trans-male after a phalloplasty procedure.

Figure 46:
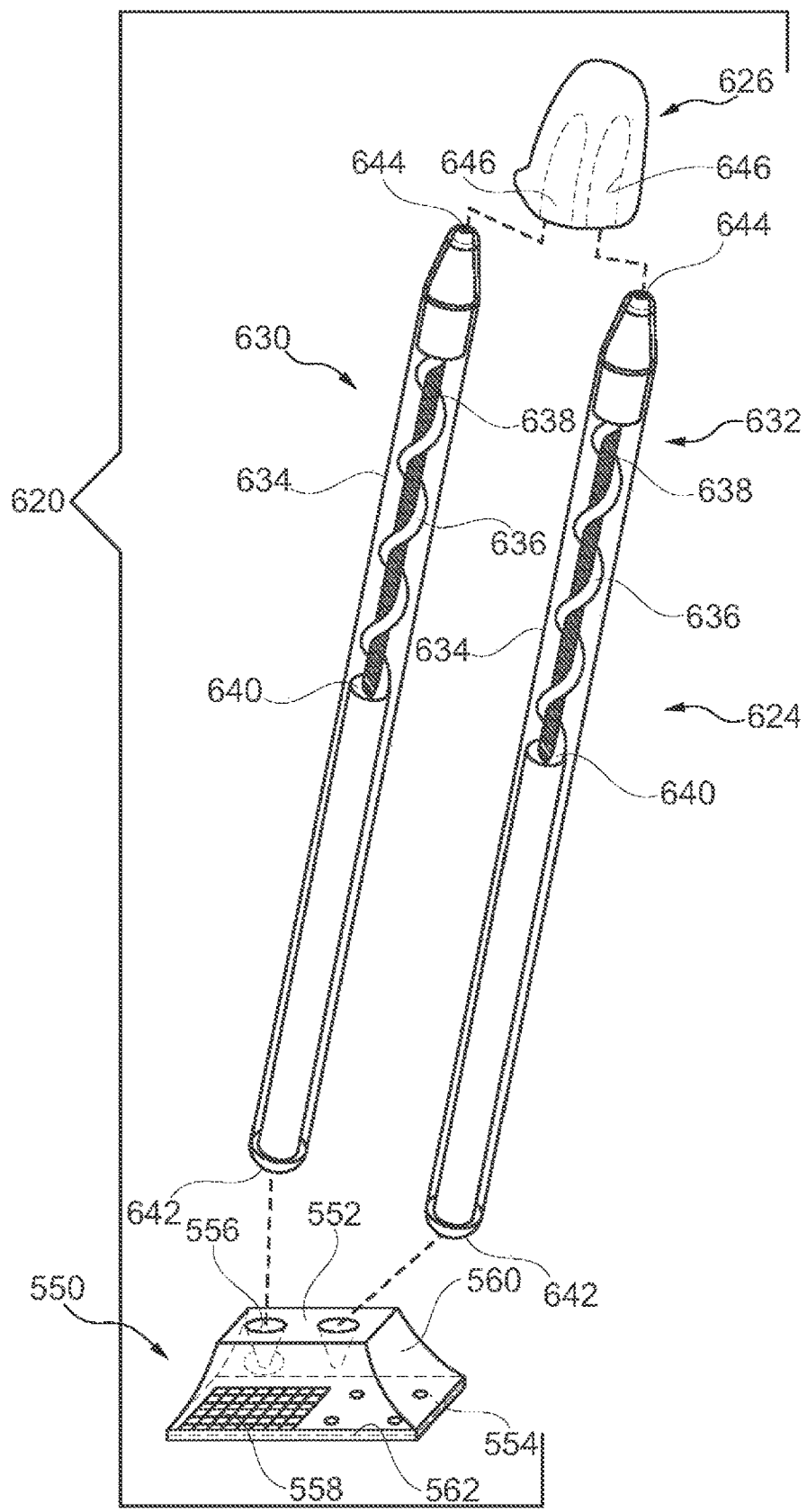
FIG. 46 is a schematic view of one embodiment of a kit of parts of a neophallus implant system including dual, malleable penile prosthetics implantable in a neophallus of a trans-male pelvis during a FTM phalloplasty procedure.

FIG. 46 is a perspective view of one embodiment of a kit of parts 620. The kit of parts 620 includes an implantable support 550 (see FIG. 42), a pair of implantable, malleable penile prosthetics 624, and an artificial glans 626. The implantable, malleable penile prosthetic 624 includes a first malleable prosthetic 630 and a second malleable prosthetic 632. Each of the first and second malleable penile prosthetic 630, 632 includes a silicone elastomer shaft 634 surrounding a silver wire coil 636 that is wound around a silver wire core 638, where the core 638 and coil 636 are contained within a polymer 640, such as a polyester or a polyethylene terephthalate. In one embodiment, both portions are overmolded with the silicone shaft 634 to form a body of the malleable penile prosthetic 624. In one embodiment, a hydrophilic coating is applied to the exterior surface of the malleable penile prosthetic 624. In one embodiment, the hydrophilic coating functions to absorb an antimicrobial agent that is applied to the exterior surface of the malleable penile prosthetic 624 prior to implantation. In one embodiment, an antimicrobial or prophylactic coating is applied to the exterior surface of the malleable penile prosthetic 624.

The silver wire coil 636 and core 638 allows the malleable prosthetic 624 to be bent by the user between an erect position (second state) for penetrative intercourse and a lowered flaccid position (first state). Suitable malleable penile prosthetic includes the GENESIS® malleable penile prosthetic available from Coloplast Corp., Minneapolis, Minn. Each of the first and second malleable penile prosthetic 630, 632 includes a proximal end 642 that is sized for insertion into one of the artificial crus penis receptacles 556, and a distal end 644 that is sized for insertion into mating recesses 646 of the artificial glans 626. The kit of parts 620 is supplied to a surgeon in a single, sterile package that provides a healthcare facility with components that are suited to implant and support a dual cylinder penile prosthetic and a trans-male after a phalloplasty procedure.

Figures 47A, 47B:
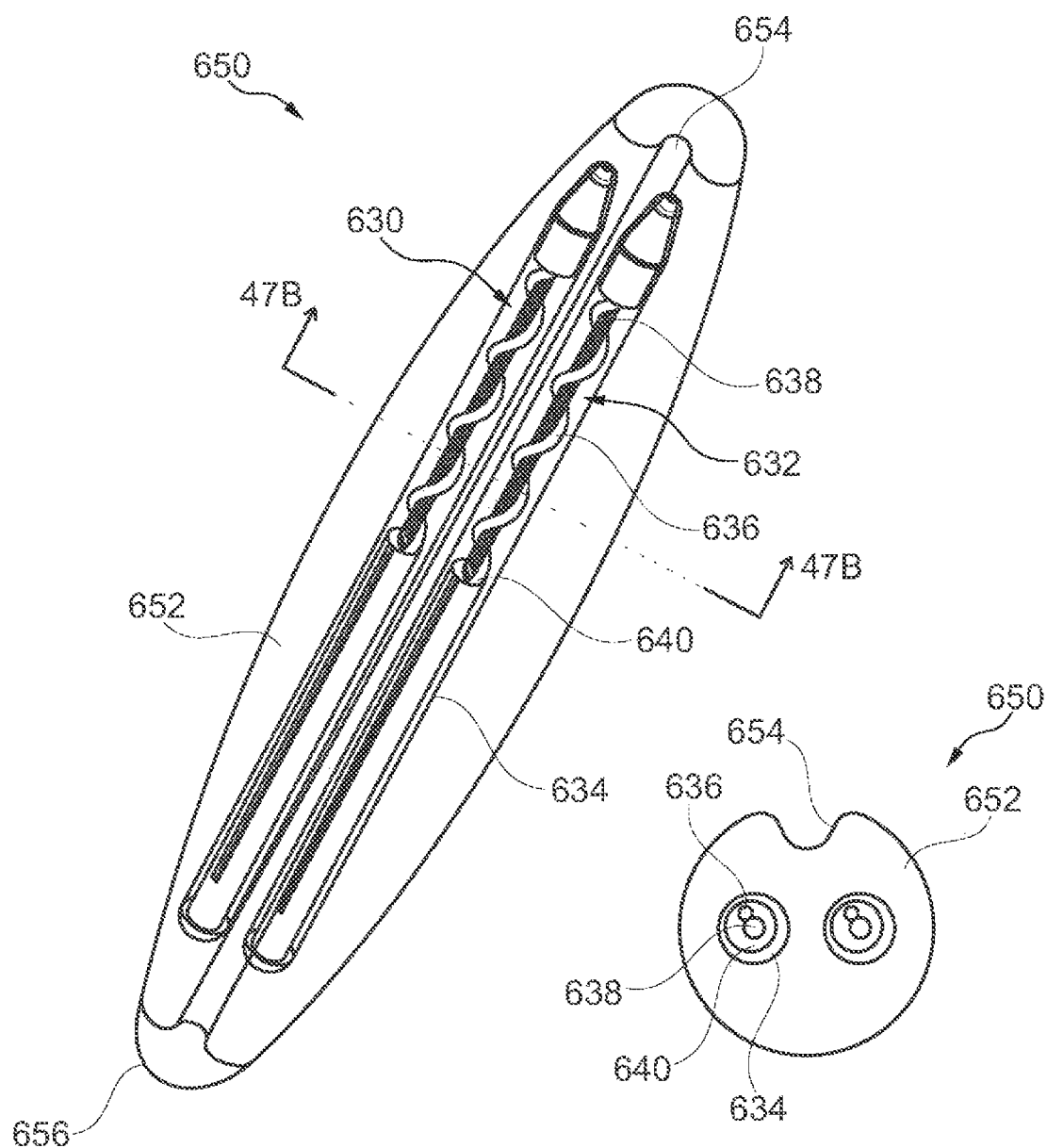
FIG. 47A is a perspective view and FIG. 47B is a cross-sectional view of one embodiment of an implantable penile prosthetic including an artificial tunica.

FIG. 47A is a perspective view and FIG. 47B is a cross-sectional view of one embodiment of an implantable penile prosthetic 650. The trans-male patient does not have a tunica to support the erectile member of the penis as is found in the natal male (see FIG. 1C). The implantable penile prosthetic 650 offers a solution to the trans-male patient to have an implantable component that offers an erection and an artificial tunica portion. In one embodiment, the implantable penile prosthetic 650 includes a pair of malleable penile inserts 630, 632 encased in an artificial tunica 652. Each of the pair of malleable penile inserts 630, 632 is as described above in FIG. 46, and includes the silicone elastomer shaft 634 surrounding the silver wire coil 636 that is wound around the silver wire core 638, where the core 638 and coil 636 are contained within the polymer 640. The artificial tunica 652 is molded around both malleable penile inserts 630, 632 and includes a longitudinal trough 654 extending along an entire length of the artificial tunica 652. The longitudinal trough 654 is adapted to receive the neourethra that is formed during the phalloplasty procedure. The malleable penile inserts 630, 632 are adapted to be bent by the user between an erect position, and a relaxed (non-erect) position. The artificial tunica 652 is also adapted to be malleable to move with both penile inserts 630, 632. The artificial tunica 652 is formed from a malleable and flexible polymer, such as an elastomer, or another silicone. The implantable penile prosthetic 650 includes a proximal end 656 that is adapted to be inserted into one of the implantable supports described above, or otherwise attached to the descending ramus of the trans-male pelvis. The proximal end 656 of the implantable penile prosthetic 650 is thus supported by the pelvis and is enclosed in the neophallus. The artificial tunica provides the means for reducing erosion of an implanted penile prosthetic through the neophallus of a neopenis implanted in a trans-male. The artificial tunica provides the means for supporting the implanted penile prosthetic within the neophallus of the trans-male. The artificial tunica provides the means for reducing or preventing the movement of the implanted penile prosthetic within the neophallus off of the longitudinal axis of the neophallus.

The implantable penile prosthetic 650 is implanted into the patient in one of the stages of the FTM phalloplasty procedure. The phalloplasty procedure can include multiple steps, such as laparoscopic hysterectomy, joining of the lengthened neourethra to the natal urethra, a vaginectomy, a glansplasty at the distal neophallus, placement of testicular prosthetics, and transposition of the clitoris to the base of the neophallus. In one embodiment, a temporary and removable place saver is implanted into the neophallus to maintain an opening in the neophallus that is sized to subsequently receive the implantable penile prosthetic 650. The place saver is an object, such as an oblong balloon, that occupies an interior cavity formed in the neophallus. In one embodiment, the implantable penile prosthetic 650 is implanted into the phalloplasty as one of the multiple steps.

Figure 48:
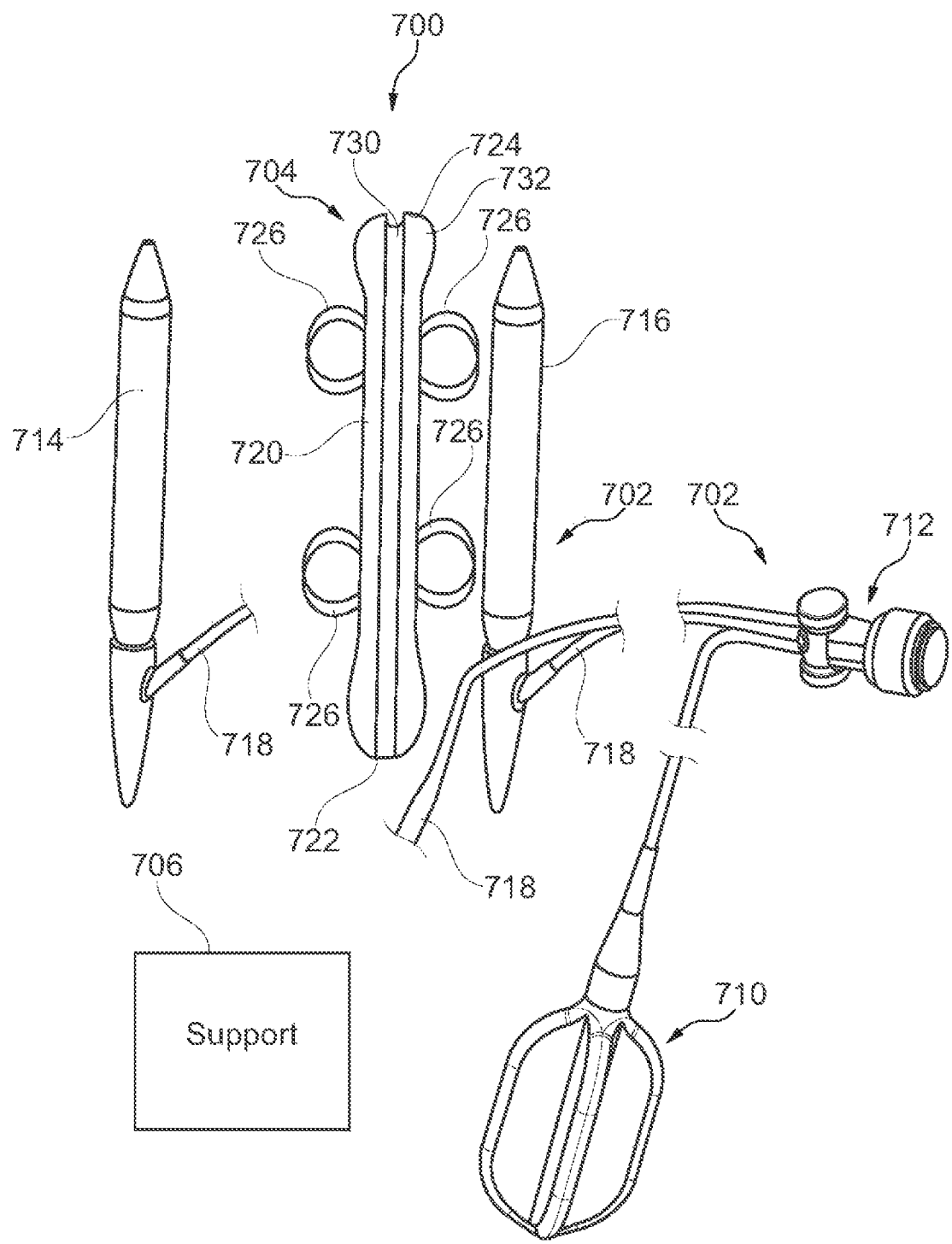
FIG. 48 is a perspective view of one embodiment of a neophallus implant system.

FIG. 48 is a perspective view of one embodiment of a neophallus implant system 700. The implant system 700 includes an inflatable penile prosthetic 702, an artificial septum 704, and an artificial crus recess support 706. The trans-male pelvis is surgically altered to include a neophallus, but the neophallus does not include the tunica that surrounds the erectile tissue or a septum that separates one corpora cavernosum from an adjacent corpora cavernosum (see FIG. 1C). It is desirable to provide the trans-male patient with a neophallus that includes an effective penile prosthetic having as many characteristics of the natal male penis as possible. The artificial septum 704 provides a structure that supports the penile implants, provides a septum to separate the inflatable prosthetics of the penile implant, and provides a level of rigidity associated with the natal male penis. The artificial septum 704 provides the means for reducing erosion of an implanted penile prosthetic through the neophallus of a neopenis implanted in a trans-male. The artificial septum 704 provides the means for supporting the implanted penile prosthetic within the neophallus of the trans-male. The artificial septum 704 provides the means for reducing or preventing the movement of the implanted penile prosthetic within the neophallus off of the longitudinal axis of the neophallus.

The inflatable penile prosthetic 702 includes a reservoir 710 that is adapted to hold a volume of liquid, a pump 712 that is adapted to move the liquid out of the reservoir 710, and a pair of inflatable prosthetics including a first inflatable penile prosthetic 714 and a second inflatable penile prosthetic 716 that are coupled to the reservoir 710 in the pump 712 by tubing 718. One suitable implantable penile prosthetic 252 is the TITAN® penile prosthetic available from Coloplast Corp., Minneapolis, Minn.

The artificial septum 704 includes a longitudinal body 720 that extends between a proximal end 722 and a distal end 724, and a plurality of clasps 726 that are adapted to secure the first and second inflatable penile prosthetics 714, 716 to the artificial septum 704. In one embodiment, the longitudinal body 720 is formed to include a longitudinal trough 730 that extends an entire length between the proximal and distal ends 722, 724. The longitudinal trough 730 is adapted and sized to receive a neourethra of the neophallus. In one embodiment, the proximal end 722 of the artificial septum 704 is adapted to engage with the support 706, where the support 706 includes any of the supports described in this application, two examples of which include the support 84 (FIG. 11A) or the support 220 (FIG. 25). In one embodiment, the distal ends 724 of the artificial septum 704 has a bulbous shape 732 that provides stability at the distal end of the penile prosthetic 702 as well as lateral support to each of the inflatable penile prosthetics 714, 716. In one embodiment, the clasps 726 are adjustable clasps that have an adjustable diameter that can be secured around a diameter of each of the inflatable penile prosthetics. The clasps 726 include elastic clasps that stretch as the inflatable penile prosthetics 714, 716 inflate and expand. The proximal end 722 has a bulbous shape that expands laterally to provide support to the tapered proximal ends of each of the inflatable penile prosthetics 714, 716. The body 720 of the artificial septum 704 is adapted to have a level of flexibility similar to the flexibility of the flaccid male penis, for example by being molded from an elastomeric polymer. The body 720 also supports the inflatable penile prosthetics 714, 716 to provide the inflatable penile prosthetic 702 with a level of longitudinal rigidity when the inflatable penile prosthetics 714, 716 are inflated. One suitable material for the formation of the artificial septum 704 includes silicone, where the clasps 726 are monolithically formed to the body 720. A suitable silicone includes a silicone elastomeric polymer having a durometer of 50-60 Shore A.

Alternatively, the clasps 726 may be added to the body 720 separately. Although FIG. 48 illustrates two clasps 726 on each lateral side of the body 720, it is to be understood that a single clasp on each side of the body 720 in the shape of a sleeve such as the implantable support 200 (FIG. 23A) is acceptable, as are three or more clasps on each side of the body 720.

Figure 49B:
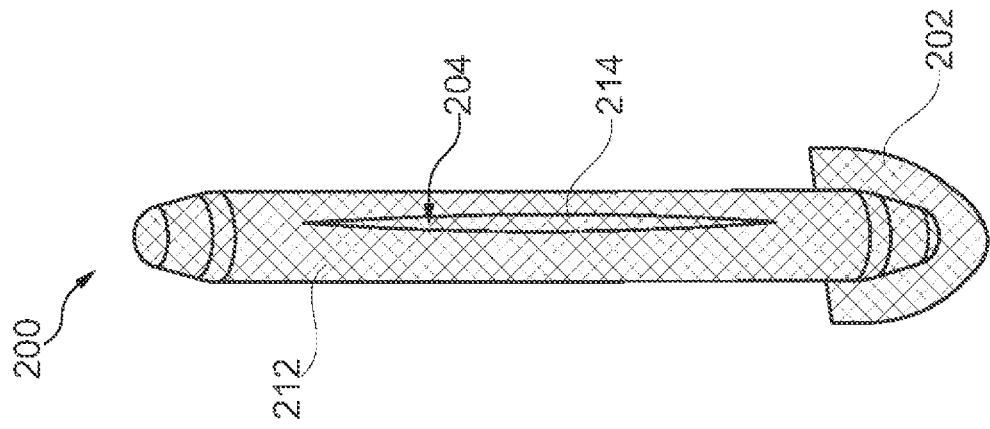
FIG. 49B is a perspective view of the support illustrated in FIG. 23A and illustrated on the same drawing sheet alongside the implantable support of FIG. 49A.
Figure 49A:
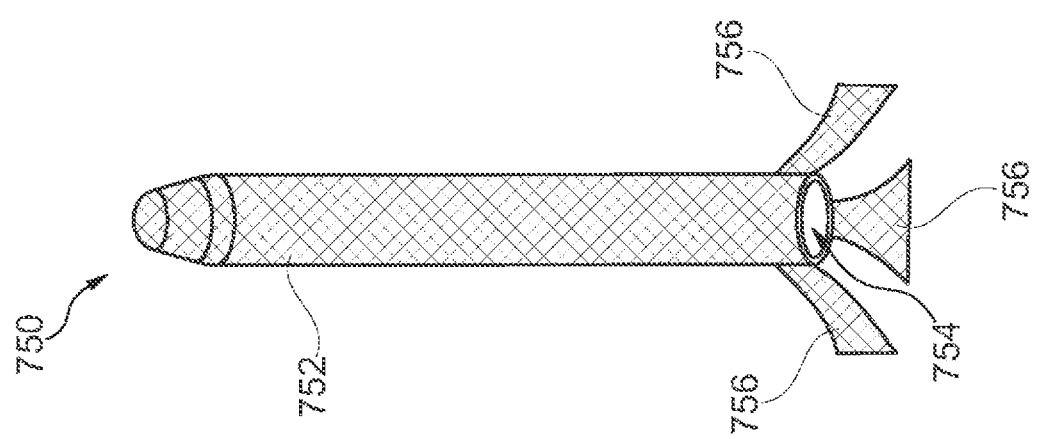
FIG. 49A is a perspective view of one embodiment of an implantable support.

FIG. 49A is a perspective view of one embodiment of an implantable support 750, and FIG. 49B is a perspective view of one embodiment of the implantable support 200 (FIG. 23A). Embodiments described below include fabricating each of the implantable supports 750, 200 through 3-D printing with expanded polytetrafluoroethylene (ePTFE).

The implantable support 750 includes a sleeve 752 provided with a recess 754 and a base that is provided with securement flaps 756. At least the sleeve 752 of the implantable support 750 is porous, where the remainder of the sleeve is fabricated by 3-D printing the ePTFE. In one embodiment, at least the sleeve 752 of the implantable support 750 is seeded with tissue growth factors to encourage tissue growth through the sleeve 752. The recess 754 is sized to receive an implantable penile prosthetic, such as the inflatable style of penile prosthetic or the malleable style of penile prosthetic described above. The securement flaps 756 are adapted to be secured to the periosteum tissue that covers the bone of the pelvis, for example the ramus, to provide the implantable support 750 with an artificial fundiform ligament. To this end, the securement flaps 756 contribute to anchoring the implantable support 750 in the orientation associated with the natal male penis. The implantable support 750 is adapted for insertion into a neophallus of a trans-male pelvis, either before or after a penile prosthetic is secured within the recess 754.

The implantable support 200 of FIG. 49B is described above in FIG. 23 and includes the sleeve 212 that has an opening 214 into the recess 204, where the recess 204 is sized to receive a penile prosthetic. The base 202 is analogous to the securement flaps 756, and are described above in FIG. 23. In one embodiment, the implantable support 200 is fabricated by 3-D printing with ePTFE, where at least the sleeve 212 is porous to encourage tissue ingrowth. In one embodiment, at least the sleeve 212 is seeded with tissue growth factors. The implantable support 200 is adapted to receive one implantable penile prosthetic. The implantable support 220 (FIG. 25) is adapted to receive two implantable penile prosthetics. In one embodiment, the dual style support 220 is fabricated by 3-D printing with ePTFE, where at least the sleeve portion 232 is porous to encourage tissue ingrowth. In one embodiment, at least the sleeve 232 is seeded with tissue growth factors.

Embodiments of the implantable supports 750, 200, 220 provide the neopenis of the trans-male with an artificial tunica that provides lateral and longitudinal support to whichever style of implantable penile prosthetic is selected by the surgeon. The artificial tunica provides the means for reducing erosion of an implanted penile prosthetic through the neophallus of a neopenis implanted in a trans-male. The artificial tunica provides the means for supporting the implanted penile prosthetic within the neophallus of the trans-male. The artificial tunica provides the means for reducing or preventing the movement of the implanted penile prosthetic within the neophallus off of the longitudinal axis of the neophallus.

Figures 50A, 50B:
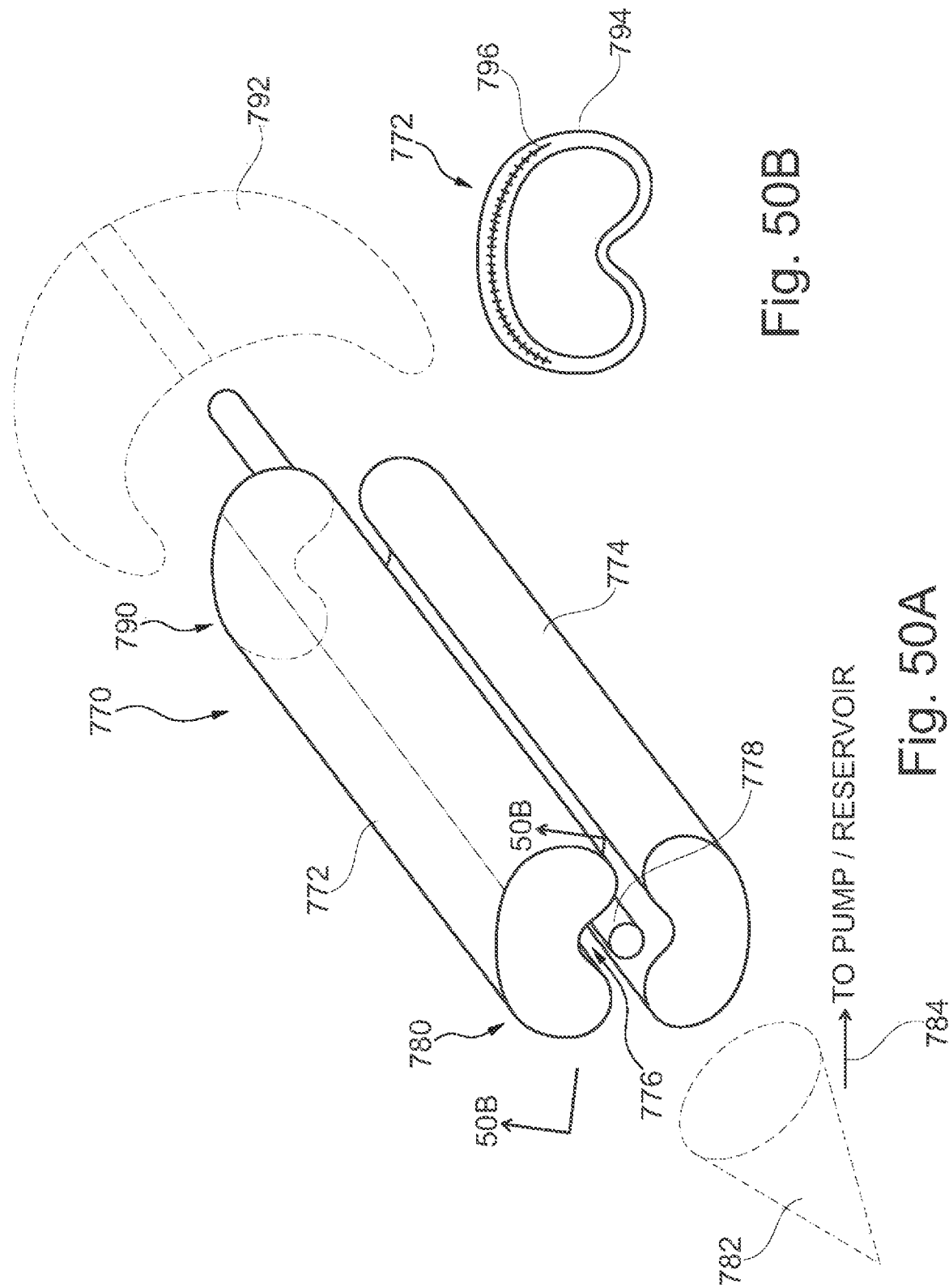
FIG. 50A is a perspective view of one embodiment of an implantable support.
FIG. 50B is a cross-sectional view of one-half of the implantable support.

FIG. 50A is a perspective view of one embodiment of an implantable support 770. FIG. 50B is a cross-sectional view of one half of the implantable support 770 of FIG. 50A.

Implantable support 770 includes a first portion 772 that meets with a second portion 774 to provide a passageway 776 for a neourethra 778 formed during a phalloplasty procedure with a trans-male patient. The first portion 772 is formed to have a cross-sectional kidney shaped profile that is symmetric with a kidney shaped profile of the second portion 774. The implantable support 770 includes a proximal end portion 780 that is adapted to be coupled to a proximal end 782 that communicates with a pump and a reservoir at 784, similar to the system illustrated in FIG. 48. The implantable support 770 includes a distal end portion 790 that is insertable into the neophallus, and in one embodiment is adapted to be coupled to an artificial glans 792. The combination of the implantable support 770, the proximal end 782, and the artificial glans 792 are adapted to provide the trans-male with an implantable neophallus system that will provide the trans-male with a neopenis that is suitable for penetrative intercourse. In one embodiment, the first portion 772 and the second portion 774 are inflatable with liquid supplied by the reservoir and are suitably formed from an elastomeric polymer system, examples of which include polyurethane or silicone.

FIG. 50B is a cross-sectional view of the first portion 772 where a wall 794 has been reinforced with a composite structure 796. In one embodiment, the wall 794 is fabricated from an elastomeric polymer and the composite structure 796 is a reinforcing mesh. The reinforcing mesh is suitably selected from polymeric meshes formed from polypropylene, nylon, polyurethane, polyethylene, or other elastomeric materials. The composite structure 796 provides a limit stop to the lateral expansion of the wall 794 of the first portion 772 to thus provided an analogous structure to the tunica of the natal male penis.

FIG. 51A is a perspective view of one embodiment of a neophallus implant 800. The neophallus implant 800 includes a spine 802 supporting a first inflatable penile prosthetic 804 and a second inflatable penile prosthetic 806, and an artificial glans penis 808. The neophallus implant 800 is implantable into a neophallus of a trans-male to provide the trans-male with a neopenis that is suitable for penetrative intercourse. Embodiments include fixation of the proximal end portion of the neophallus implant 800 to an appropriate implantable support, such as any one of those described above, to allow the neophallus implant 800 to have the orientation of a natal male penis and to support penetrative intercourse.

FIG. 51B is a perspective view of the spine 802. The spine 802 includes a first portion 810 and a second portion 812. The first portion 810 includes a first concave surface 814 adapted to receive the first inflatable prosthetic 804 and a second concave surface 816 adapted to receive the second inflatable prosthetic 806. Located between the first concave surface 814 and the second concave surface 816 is a third concave surface 818 that has a radius of curvature. The third concave surface 818 is adapted to receive a neourethra of the neophallus created for the trans-male. The second portion 812 of the spine 802 is symmetric to the first portion 810 and includes a first concave surface 824, a second concave surface 826, and a third concave surface 828 that are symmetric and complementary to the concave surfaces 814, 816, 818, respectively. The first portion 810 is adapted to snap together with the second portion 812 at location 830, for example by a snap-fit coupling. The spine 802 provides a semi-rigid elongate body that supports the neophallus implant 800 and both protects and supports the neourethra of the trans-male.

FIG. 51C is a cross-sectional view of the proximal portion of the neophallus implant 800. The first portion 810 has been snapped together with the second portion 812 such that the concave surfaces 818, 828 combine to form a recess 832 that is sized to receive the neourethra. The concave surfaces 814, 824 combine to provide a supporting surface that is sized to receive the inflatable prosthetic 804. The concave surfaces 816, 826 combine to provide a supporting surface that is sized to receive the inflatable penile prosthetic 806. One suitable material for forming the spine 802 is a silicone material with a suitable durometer to allow movement of the neophallus between an erect position in a flaccid position.

Figure 52:
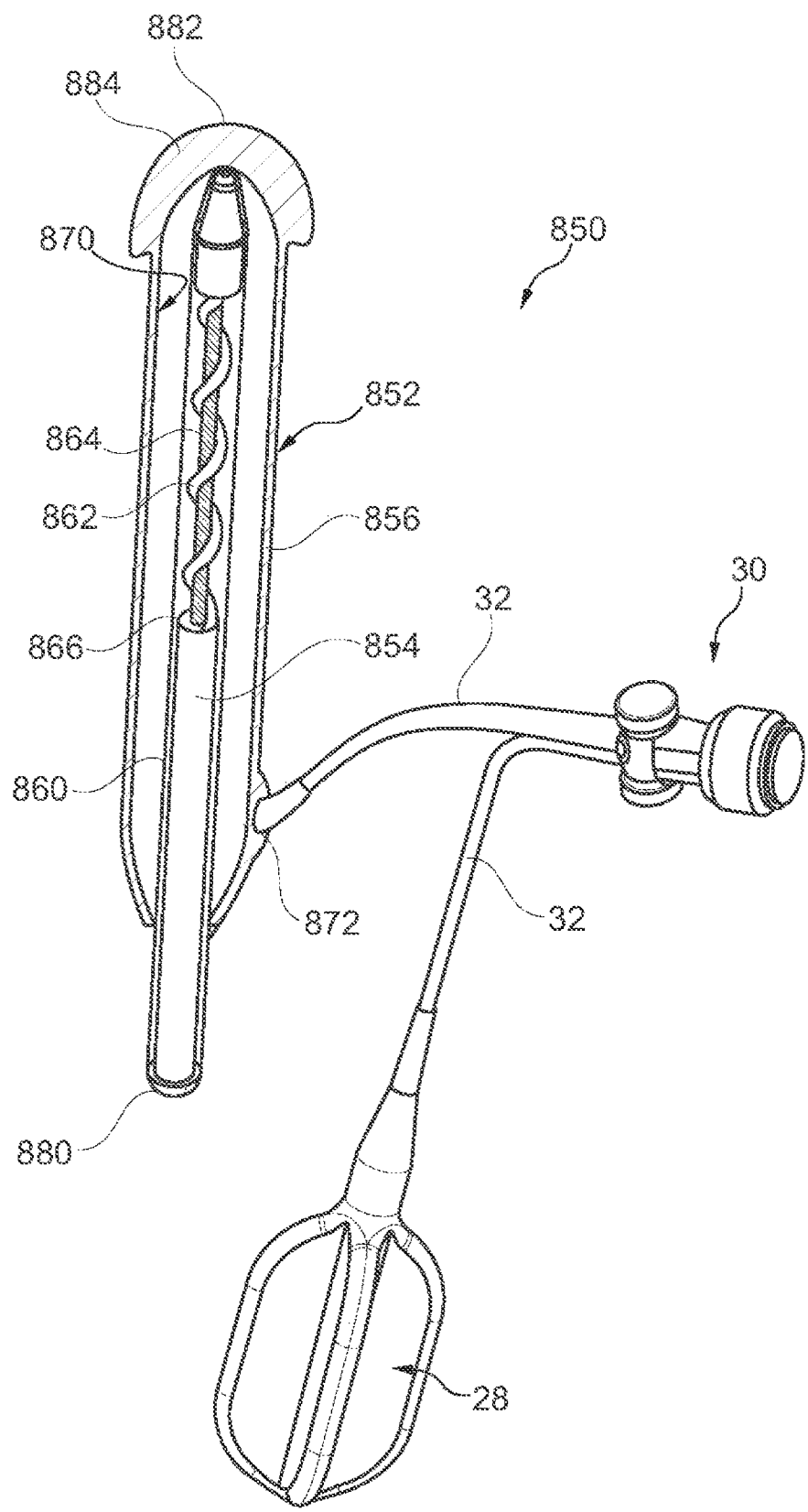
FIG. 52 is a perspective view of one embodiment of a neophallus implant system.

FIG. 52 is a perspective view of one embodiment of a neophallus implant system 850. The neophallus implant system includes the reservoir 28 and the pump 30 connected to a penile prosthetic 852 by the tubing 32. The reservoir 28, the pump 30, and the tubing 32 are as described in U.S. Pat. Appln. Pub. 2011/0118540, which issued as U.S. Pat. No. 8,337,392, the disclosure of which is incorporated by reference in its entirety into this application.

The penile prosthetic 852 includes a malleable core 854 retained inside of an inflatable implant 856. The malleable core 854 is similar to the malleable prosthetics described above, and includes a silicone elastomer shaft 860 surrounding a silver wire coil 862 that is wound around a silver wire core 864, where the silver wire core 864 and coil 862 are contained within a polymer 866.

The inflatable implant 856 includes an inflatable bladder 870 that communicates with the reservoir 28 and the pump 30 by a tube connector 872. The liquid retained inside of the reservoir 28 is moved by the pump 30 into the inflatable bladder 870, and subsequent pumping motion increases the pressure within the inflatable bladder 870.

In one embodiment, the penile prosthetic 852 has a proximal end 880 that is defined by the malleable core 854 and a distal end 882 that is provided by an artificial glans penis 884. In one embodiment, the artificial glans penis 884 is integrated with a distal end of the malleable core 854. The inflatable bladder 870 extends a distance in the proximal direction beyond the tube connector 872 and is connected to the malleable core 854 by a fluid tight bond. The malleable core 854 provides enhanced column strength and girth for the penile prosthetic 852. The inflatable implant 856 provides enhanced fullness and an improved erection.

The neophallus implant system 850 is compatible with implantation along with any of the implantable supports described above, and thus provide the trans-male with a neopenis that functions and has an orientation, after implantation, of that of the natal male penis.

Figure 53:
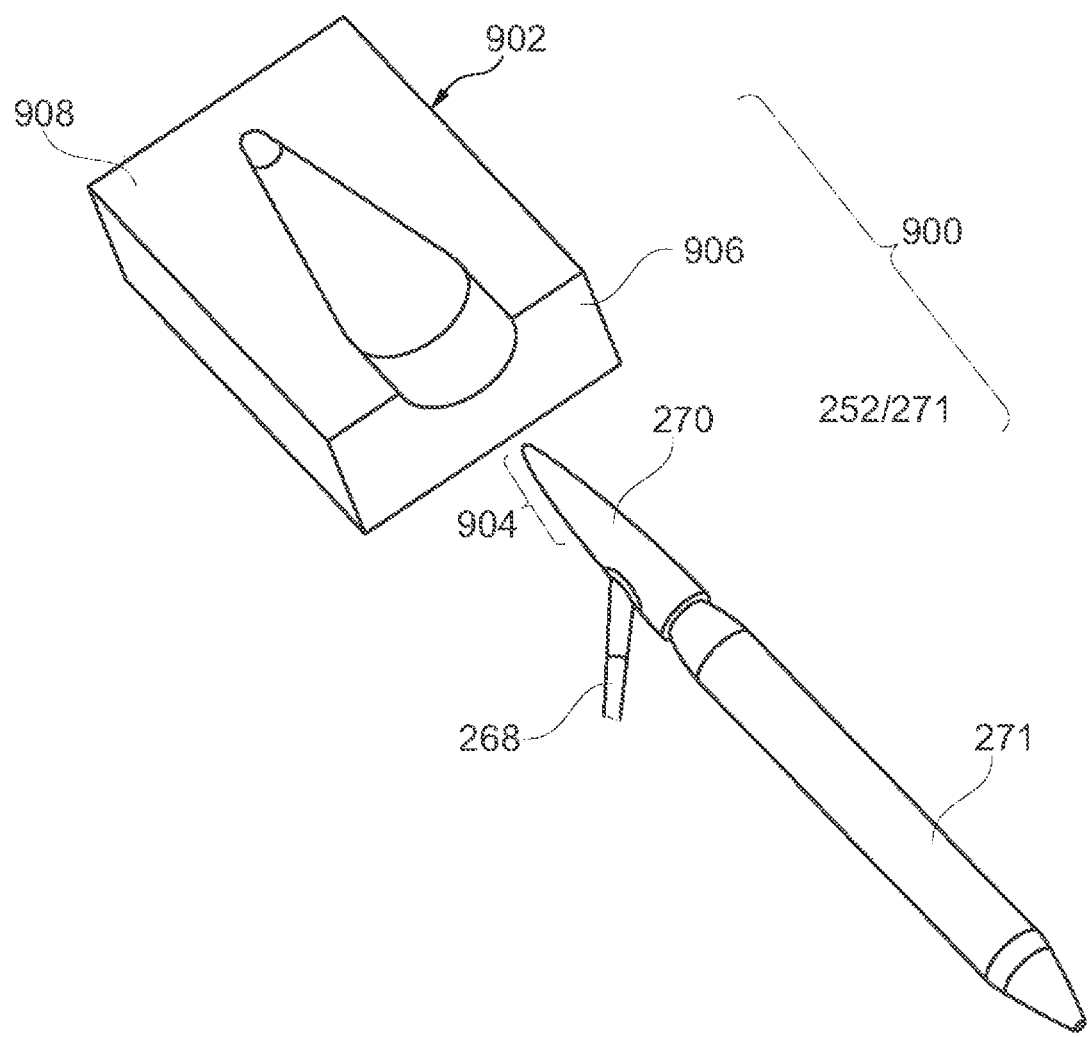
FIG. 53 is a perspective view of one embodiment of a kit of parts suitable for customizing an implant during a phalloplasty procedure.

FIG. 53 is a perspective view of one embodiment of a kit of parts 900 suitable for a phalloplasty procedure. The kit of parts includes a cutting jig 902 that offers utility to a surgeon to customize the proximal tip angle for an inflatable cylinder 271 if employed to treat erectile dysfunction in a natal male. For example, the surgeon may decide to adjust the proximal tip angle for an inflatable cylinder 271 to accommodate a necrotic crus penis recess. The implantable penile prosthetic 252 has been described above in FIG. 27. Surgeons have developed familiarity and techniques for implanting this style of the implantable penile prosthetic 252.

The neophallus of the trans-male is constructed from the patient's own tissue. It can be desirable to have the ability to customize aspects of the implantable penile prosthetic 252 to more closely agree with the newly created anatomy in the trans-male. The cutting jig 902 allows customization of the proximal portion of the inflatable cylinder 271 during a phalloplasty procedure.

In embodiment, the implantable penile prosthetic 252 includes the dual inflatable cylinders 271, each having the proximal end 270 that is sized for insertion into one of the artificial crus penis receptacles described above 556. One suitable implantable penile prosthetic 252 is the TITAN® penile prosthetic available from Coloplast Corp., Minneapolis, Minn. The proximal end 270 includes a pointed portion 904. It is desirable in some cases to shorten the length of the proximal end 270 of the inflatable cylinder 271 by inserting the proximal end 270 into the cutting jig 902 and cutting along the face 906. It is desirable in some cases to alter an attachment angle of the proximal end 270 of the inflatable cylinder 271 by inserting the proximal end 270 into the cutting jig 902 and cutting along the face 908. The cutting jig 902 allows the surgeon to shorten the length of the inflatable cylinder 271 and to adjust the contact angle of the proximal end 270 by adjusting the angle of the proximal end 270 of the inflatable cylinder 271. The surgeon may desire to shorten the length of the inflatable cylinder 271 depending upon the location of the implanted artificial crus penis receptacle. The surgeon may desire to adjust the contact angle of the proximal end 270 of the inflatable cylinder 271 depending upon the arch angle of the pelvis, as measured between the pair of descending rami for the patient. The cutting jig 902 allows the surgeon to shape the proximal end 270 by adjusting a length in the angle of the pointed portion 904.

Figure 54:
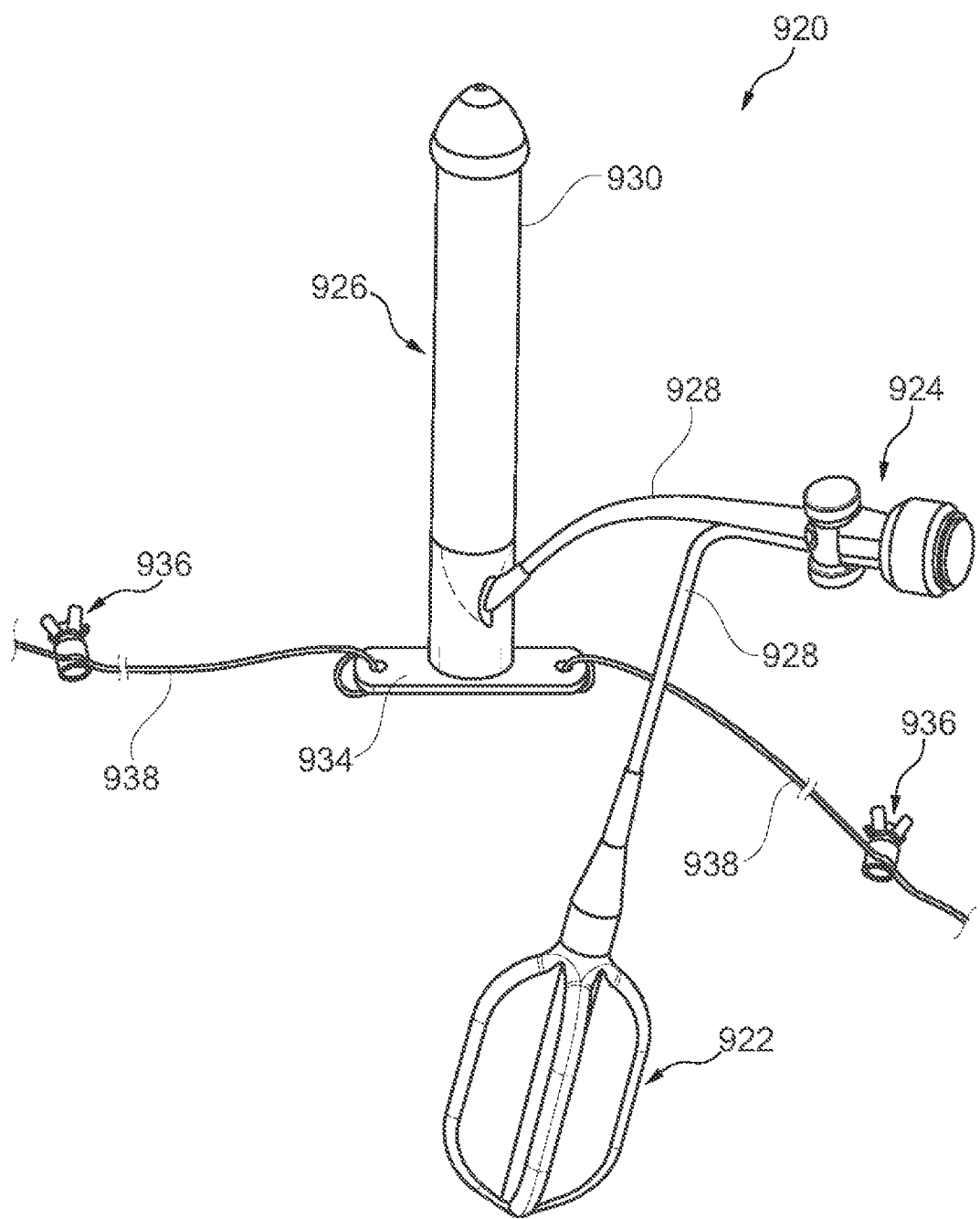
FIG. 54 is a perspective view of one embodiment of a neophallus implant system.

FIG. 54 is a perspective view of one embodiment of a neophallus implant system 920. The neophallus implant system 920 includes a reservoir 922 that is configured to contain a volume of liquid, a pump 924 that is configured to move the liquid out of the reservoir 922 and into the penile prosthetic 926. Flexible tubing 928 is adapted to connect the reservoir 922 and the pump 924 to the penile prosthetic 926.

The penile prosthetic 926 includes an inflatable distal portion 930 connected to a base 934. The base is attachable relative to the pelvis of a trans-male by the anchors 936. In one embodiment, the anchors 936 are adjustable anchors that are adapted to adjust the tension of the implant system 920 by moving any biaxial direction along a length of a strand 938. One suitable strand 938 is a polypropylene suture strand.

The reservoir 922 is sized to maintain a volume of liquid between about 50-300 ml and is adapted for implantation into the abdomen of the user, ectopically under the skin and anterior of the rectus sheath, in the space that was formerly the vaginal vault, or in the space of Retzius depending upon the procedure and the preference of the surgeon. One suitable reservoir 28 is sized to retain approximately 130 mL of liquid and is available from Coloplast Corp., Minneapolis, Minn.

The pump 924 is as described in U.S. Pat. Appln. Pub. 2007/0142700, which issued as U.S. Pat. No. 8,167,788, the disclosure of which is incorporated by reference in its entirety into this application.

The adjustable anchors 936 are as described in U.S. Pat. Appln. Pub. 2010/0198003, which issued as U.S. Pat. No. 8,585,578, the disclosure of which is incorporated by reference in its entirety into this application.

Figure 55:
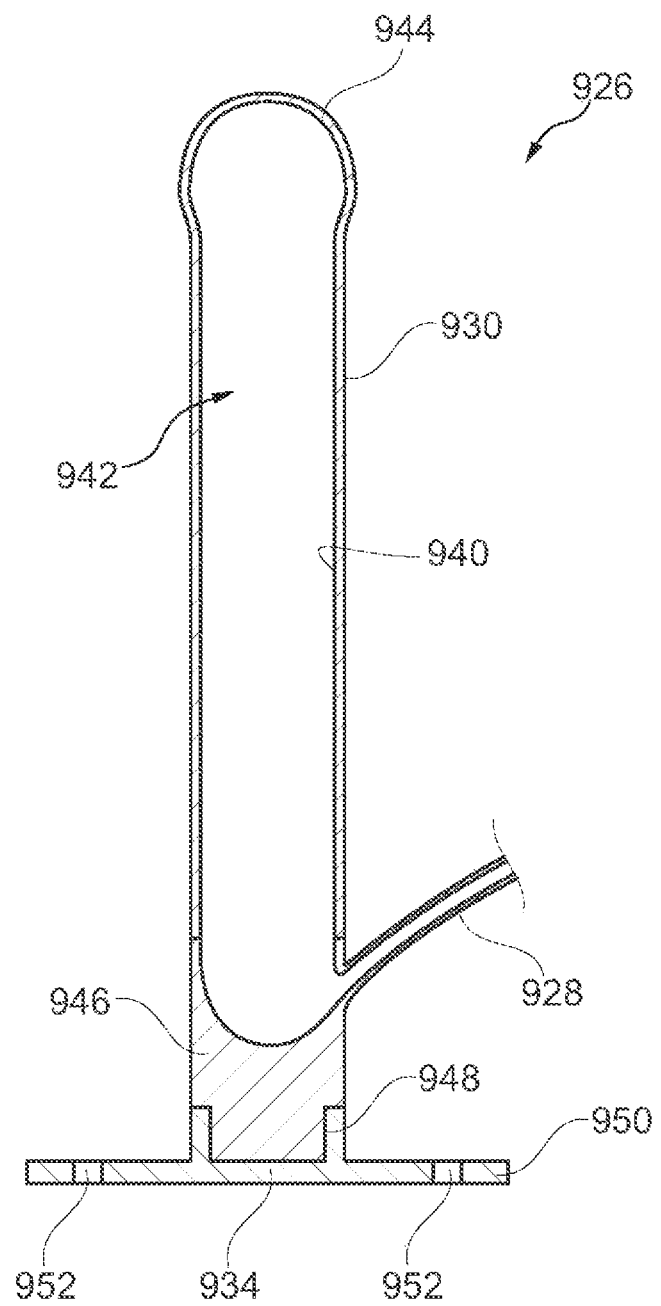
FIG. 55 is a cross-sectional view of a penile prosthetic of the neophallus implant system of FIG. 54.

FIG. 55 is a cross-sectional view of one embodiment of the penile prosthetic 926. The inflatable distal portion 930 is provided by an elastomeric wall 940 that defines a cavity 942. The cavity 942 receives the liquid from the reservoir 922 (FIG. 54), which operates to inflate and pressurize the elastomeric wall 940. In one embodiment, a bulbous artificial glans penis is provided on a distal end 944 of the inflatable distal portion 930. A proximal portion 946 of the inflatable distal portion 930 is coupled with the base 934. Suitable material for the inflatable distal portion 930 include elastomeric polymers, of which silicone is one example. The proximal portion 946 is provided as a solid cross-sectional portion that provide support and rigidity to the distal end portion 930.

The base 930 includes a bracket 948 extending from a flange 950, where the bracket 948 is integrated with the proximal portion 946 of the inflatable distal portion 930. In one embodiment, the base 934 includes eyelets 952 that are adapted to receive the strands 938 (FIG. 54).

Regarding FIG. 54 and FIG. 55, the base 934 is generally shaped to extend the distance between the descending pubic rami across the pubic arch of the trans-male. The adjustable anchors 936 are provided to fixate the neophallus implant 920 into the soft tissue of the pelvis, for example into the membrane of the obturator foramen, or into a ligament, such as the Cooper's ligament. At least one of the adjustable anchors 936 is generally attached to one side of the base 934 and at least one adjustable anchor 936 is attached to an opposite side of the base 934. In one embodiment, two adjustable anchors 936 are secured through eyelets 952 of the base 934 on each lateral side of the neophallus implant system 920, for a total of at least four anchors. Two of the adjustable anchors 936 are desirably attachable to the membrane of the obturator foramen. The other of the two adjustable anchors 936 are desirably attached to either the membrane of the obturator foramen or to a ligament.

The neophallus implant system 920 is adapted for attachment to the pelvis of the trans male, where the base 934 provides support to allow penetrative intercourse and aids in the placement of the neophallus implant system 920 in an orientation that replicates the penis in a natal male.

Figure 56:
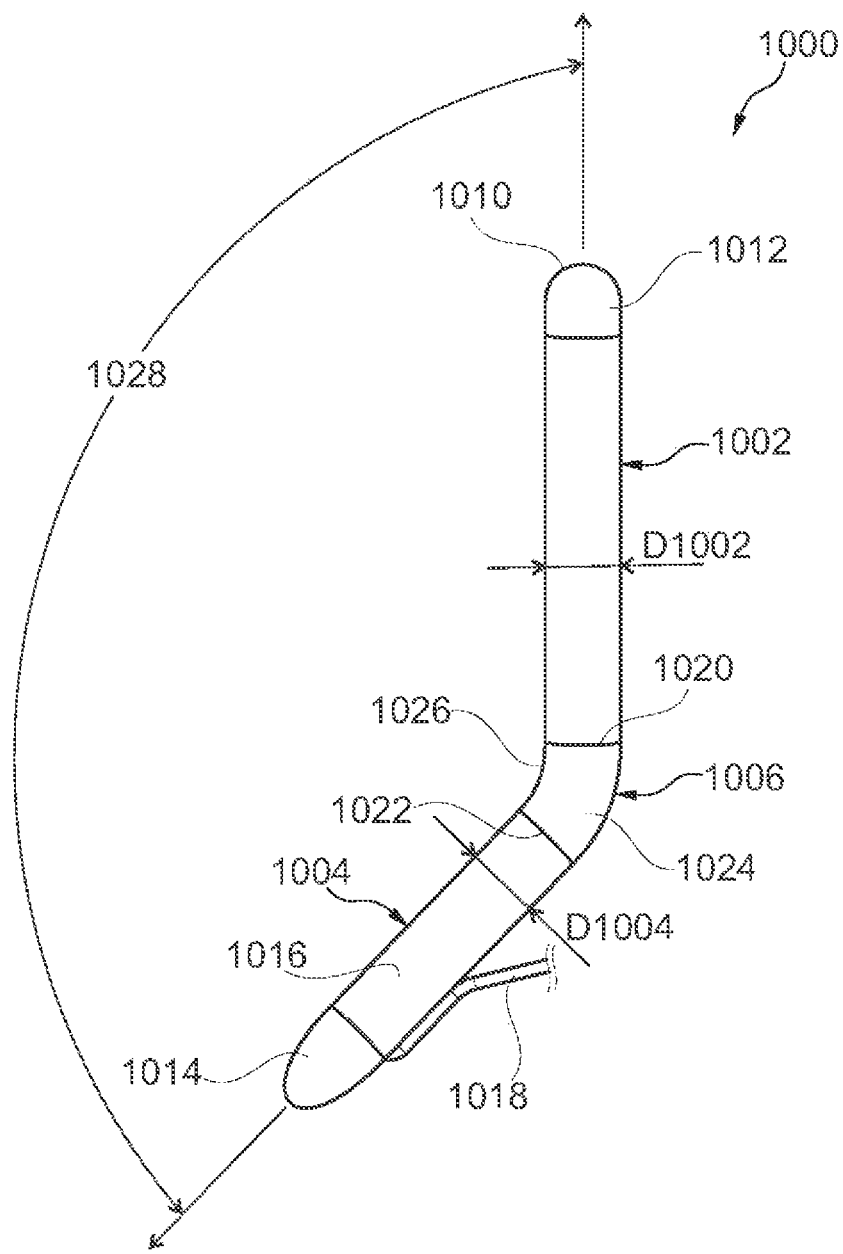
FIG. 56 is a perspective view of one embodiment of a neophallus implant.

FIG. 56 is a perspective view of one embodiment of a neophallus implant 1000. The neophallus implant 1000 includes a distal tubular portion 1002, a first proximal portion 1004, and a transfer joint 1006 connected between the distal tubular portion 1002 and the first proximal portion 1004. The neophallus implant 1000 is illustrated in an assembled state in which the transfer joint 1006 has been attached to the distal tubular portion 1002 and the first proximal portion 1004.

In one embodiment, the distal tubular portion 1002 is provided as an inflatable prosthetic having a distal end 1010 and a glans portion 1012; the first proximal portion 1004 is provided as an inflatable prosthetic having a rear tip portion 1014 coupled to an inflatable portion 1016, with a liquid port 1018 coupled to the inflatable portion 1016. The transfer joint 1006 has a distal end 1020 connected to the distal tubular portion 1002, a first proximal end 1022 connected to the first proximal portion 1004, and a body 1024 extending continuously from the distal end 1020 to the proximal end 1022.

In one embodiment, the body 1024 of the transfer joint 1006 is formed to have a fixed bend 1026. The fixed bend 1026 is configured to orient the distal tubular portion 1002 at an obtuse angle 1028 relative to the first proximal portion 1004. The fixed bend 1026 is formed into the transfer joint 1006 to ensure that the transfer joint 1006 is permanently bent and to suitably orient the implant to provide a neopenis with a conformation of that of a natal male penis. The fixed bend 1026 positions the distal tubular 1002 portion at an offset angle relative to the first proximal portion 1004. The complement to the obtuse angle 1028 is a half arch angle HAA illustrated in FIG. 57. The transfer joint 1006 has an angle that aligns the distal tubular portion 1002 off of a longitudinal axis of the first proximal portion 1004. Thus, the fixed bend 1026 accommodates the curvature for the implant allowing the proximal portion to be fixated within the pelvis alongside the ramus and allowing the distal portion to be offset from the proximal portion and to extend away from and be centered on the body of the trans-male. The transfer joint 1006 allows the first proximal portion 1004 to angle in a direction into the pelvis and away from the center line of the patient, while maintaining the distal portion on that center line of the patient.

In one embodiment, the body 1024 of the transfer joint 1006 is flexible to allow the surgeon to bend the body 1024 to achieve a desired angle that will orient the first proximal portion 1004 along the ramus and the distal tubular portion 1002 anterior the pubic bone. For example, a suitably bent body 1024 will orient the distal tubular portion 1002 at an obtuse angle 1028 relative to the first proximal portion 1004. The flexibility of the transfer joint 1006 is achieved by providing an accordion pleat, for example, or another flexible surface for the transfer joint 1006 that will allow the transfer joint 1006 to be bent at the half arch angle HAA (FIG. 57) to suitably orient the implant to provide a neopenis with a conformation of that of a natal male penis. In one embodiment, the transfer joint 1006 is formed from an elastomeric polymer that allows the joint 1006 to be bent to a desired non-zero (and non-180 degree) angle, and the surgeon subsequently fixates the implant 1000 into the body with the transfer joint 1006 in that desired angle. The flexibility of the transfer joint 1006 is adapted to position the distal tubular 1002 portion at a trans-male pelvic half arch angle HAA relative to the first proximal portion 1004. The transfer joint 1006 angle will align the distal tubular portion 1002 off of a longitudinal axis of the first proximal portion 1004. Thus, the angle of the transfer joint 1006 accommodates a curvature for the implant allowing the proximal portion to be fixated within the pelvis alongside the ramus and allowing the distal portion to be offset from the proximal portion and to extend away from the center line of the body of the trans-male. The transfer joint 1006 allows the first proximal portion 1004 to angle in a direction into the pelvis away from the center line of the patient, while maintaining the distal portion on that center line of the patient. In one embodiment, the distal tubular portion 1002 is provided as a malleable penile prosthetic (not inflatable) and the first proximal portion 1004 is provided as one of a rigid plastic or metal rod or a malleable penile prosthetic. Suitable malleable penile prosthetic includes the GENESIS® malleable penile prosthetic available from Coloplast Corp., Minneapolis, Minn. The transfer joint 1006 couples the portions 1002, 1004 together in an angled fashion where the first proximal portion 1004 is oriented for attachment to a descending ramus and the distal tubular portion 1002 has an orientation adapted for insertion into a neophallus.

Penile implants for the natal male penis are generally straight tubular shaped devices (i.e., linear along a longitudinal axis) and sized for insertion into an existing crus penis recess through the corpus cavernosum. The corpora cavernosa, the crura penis, and the tunicae of the natal male penis provide support and resist off-axis bending of the implanted penile implant laterally relative to the axis of the penis. Sometimes dual inflatable implants are implanted in the male penis to treat erectile dysfunction, and the tunica supports the dual inflatable implants to prevent either implant from crossing inside of the tissue of the penis.

The trans-male anatomy does not have corpora cavernosa, the crura penis, or the tunicae. Thus, the penile implants for the natal male are not well suited for implantation into the pelvis of the trans-male since the supporting structure of the natal male is absent. One consequence of this anatomical reality for the trans-male pelvis is that a penile implant designed for the natal male may not have adequate support to allow for penetrative intercourse after implantation into the trans-male. Embodiments provide a transfer joint 1006 that allows the implantation of a penile implant into a trans-male pelvis alongside, or adjacent, to the descending ramus in a configuration that supports the proximal portion and the transfer joint of the penile implant to facilitate penetrative intercourse. The transfer joint 1006 provides the means for coupling a proximal portion of a penile implant to a distal portion of a penile implant, such that when the neophallus implant is implanted, the proximal portion is supported to allow for penetrative intercourse and the distal portion is oriented in a position associated with the position of a penis of a natal male. The transfer joint 1006 provides the means for associating a proximal portion of a penile implant in a supporting location adapted to withstand the axial thrust associated with penetrative intercourse, and aligning a distal portion of the penile implant off of the longitudinal axis of the proximal portion to assume a natural position that is associated with the position of a penis of a natal male. The transfer joint 1006 provides the means for coupling a proximal support of a neophallus implant to a distal portion of the neophallus implant, where the proximal support is connected to a portion of the pelvis and the distal portion is implanted inside of the neophallus for penetrative intercourse.

In one embodiment, the distal tubular portion 1002 and the inflatable portion 1016 are fabricated as an expandable tube or balloon that is adapted to expand when inflated with a liquid that is injected through the liquid port 1018. The liquid port 1018 is attachable to a reservoir that contains liquid and a pump that is provided to move the liquid out of the reservoir and into the implant 1000. A suitable reservoir and a suitable pump are described above in FIG. 54. The reservoir and the pump are typically coupled to the implant 1000 after first placing the implant 1000 within the tissue of the neophallus and connecting the first proximal portion 1004 to the pelvis.

In one embodiment, the distal tubular portion 1002 has a diameter D1002 that is larger than a diameter D1004 of the first proximal portion 1004. In other words, the first proximal portion 1004 is narrower than the distal tubular portion 1002. The smaller diameter D1004 of the proximal portion can improve comfort after implantation while providing sufficient anchoring support for the neophallus implant 1000. The diameter D1004 of the proximal portion 1004 has a range from 0.5-1.5 cm. The diameter D1002 of the distal tubular portion 1002 is selected to have a girth to fill the neophallus, and the diameter D1002 is generally about two times as large as the diameter of a penile prosthetic for a natal male penis. The diameter D1002 of the distal tubular portion 1002 is a range from 1-4 cm.

The neophallus implant 1000 is implantable within a neophallus to provide a trans-male with a neopenis that is adapted for penetrative intercourse. The distal tubular portion 1002 is implantable within tissue of the neophallus, and the first proximal portion 1004 is attachable to the pelvis to orient the distal tubular portion 1002 and the newly constructed neopenis in a conformation that replicates the conformation of a natal male penis.

The neophallus implant 1000 is a prosthetic implant useful in trans-gender phalloplasty procedures or in reconstructive neopenis procedures. Embodiments provide a single distal cylinder sized and adapted for implantation into the neophallus and a proximal portion (or two proximal portions) sized and adapted for attachment to one or both of the descending pubic rami. This general structure is suitable to accommodate both inflatable prosthetics and malleable prosthetics.

Figure 57:
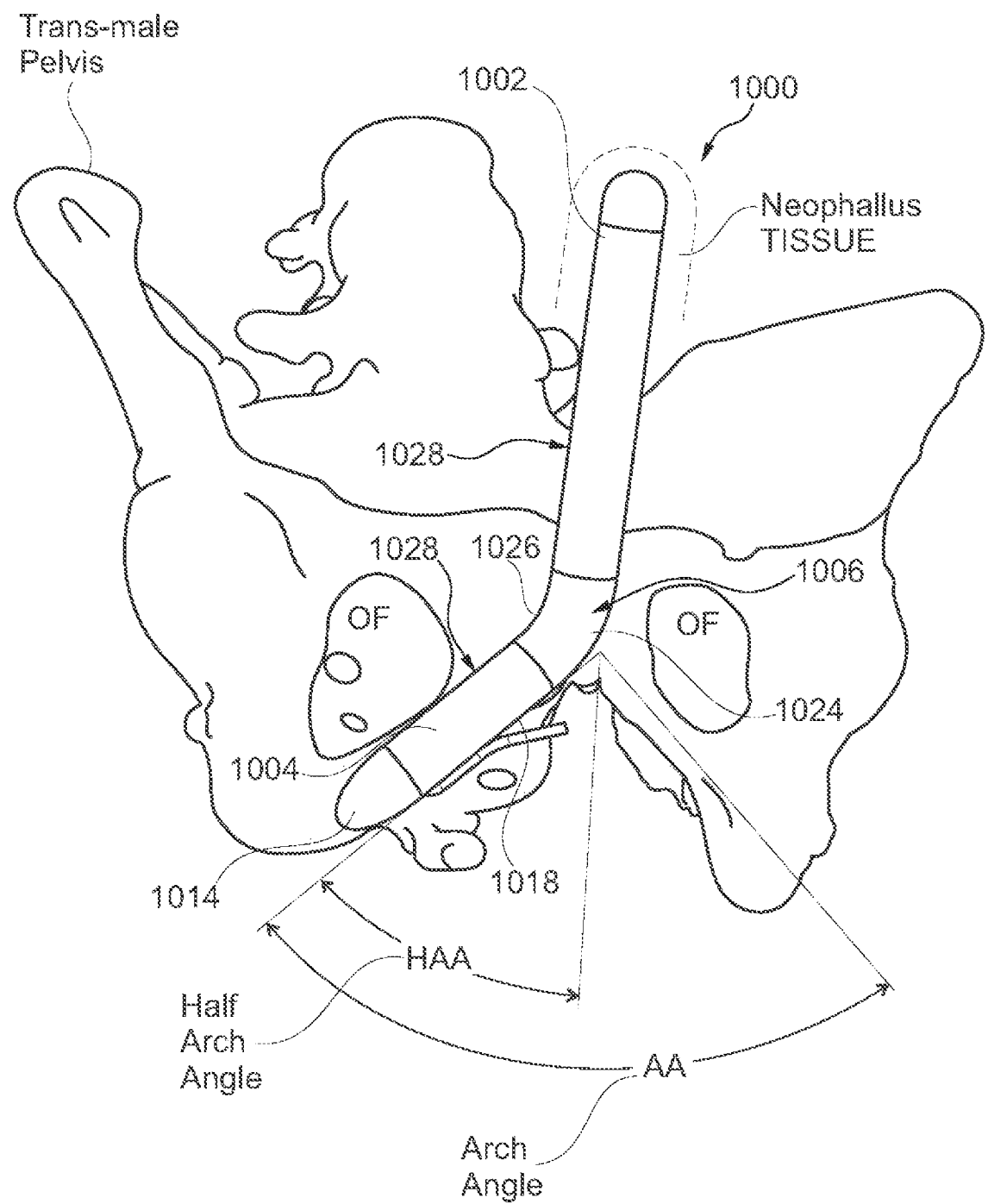
FIG. 57 is a schematic view of the neophallus implant illustrated in FIG. 56 implanted in the pelvis of a trans-male.

FIG. 57 is a schematic view of the neophallus implant 1000 implanted in and attached to a trans-male pelvis. The first proximal portion 1004 is attached to the descending pubic ramus on the right side of the patient and the transfer joint 1006 is attached to the pubic bone near the pubic symphysis. The distal tubular portion 1002 extends away from the pelvis at a non-zero and non-180 degree angle in a conformation that replicates the angle and conformation of the natal male penis on a male pelvis. The trans-male pelvis is a female pelvis that is associated with an arch angle AA measured between the descending rami. The arch angle AA of the trans-male pelvis is generally understood to be in a range from about 75-105 degrees, with an arch angle AA of about 90 degrees considered to be common. In contrast, the natal male pelvis has a narrower opening and a narrower arch angle of about 60 degrees. The body 1024 of the transfer joint 1006 has the bend 1026 that is selected to orient the distal tubular portion 1002 at a female pubic arch half angle HAA relative to the first proximal portion 1004 to so adapt the implant 1000 to provide the trans-male pelvis with an implant that has a conformation of that of the natal male. This configuration improves the stability of the neophallus implant 1000 and better approximates the male proximal penile structures of the natal male corpora cavernosa.

The first proximal portion 1004 is attachable to the ramus by suturing the rear tip portion 1014 to the ramus with suture stitches, or attaching the first proximal portion 1004 to one of the implantable supports described above. Alternatively, the surgeon may choose to wrap the first proximal portion 1004 with an implantable fabric that secures the first proximal portion 1004 to the descending pubic ramus.

Figure 58:
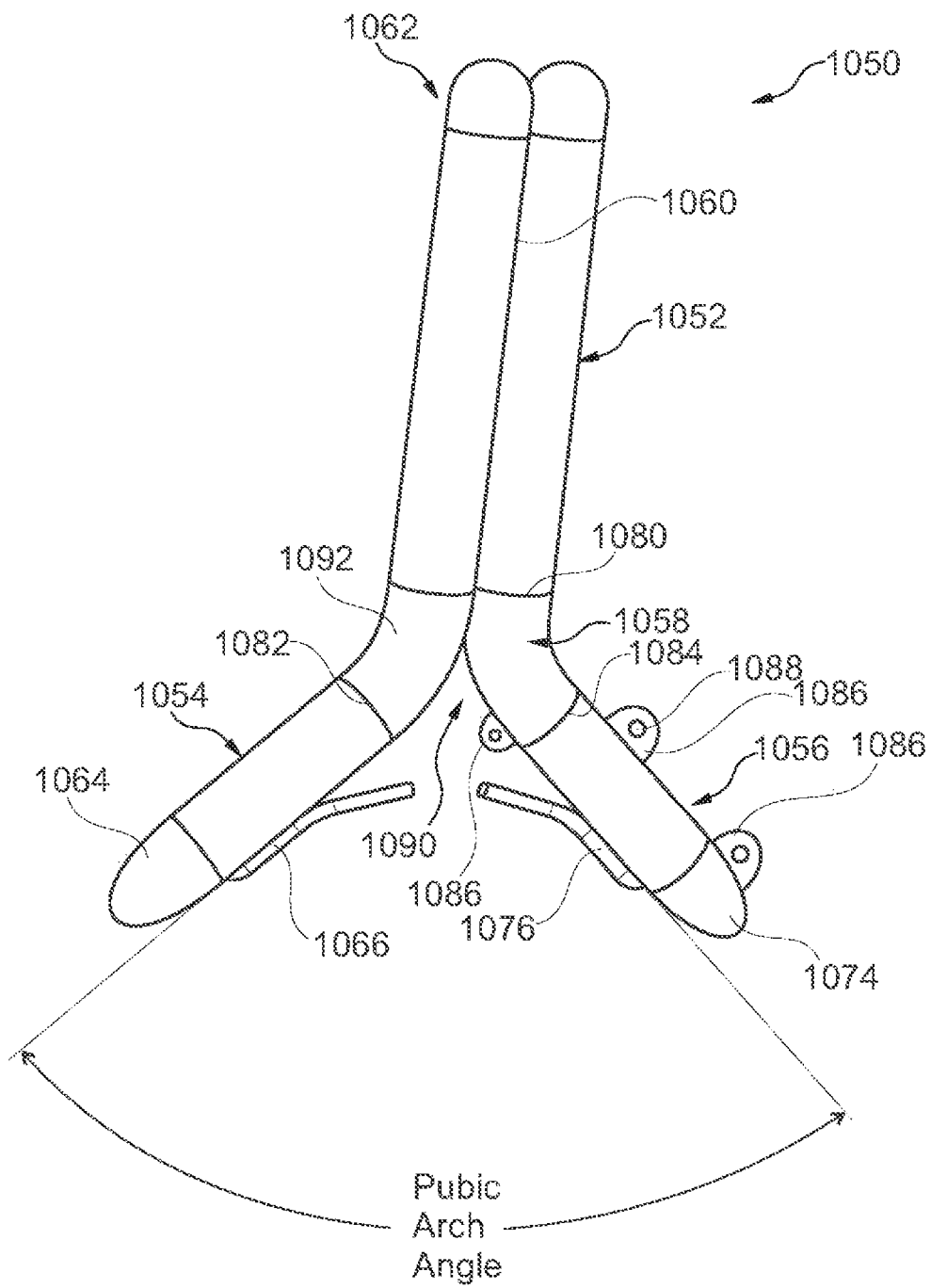
FIG. 58 is a perspective view of one embodiment of a neophallus implant including bifurcated proximal portions.

FIG. 58 is a perspective view of one embodiment of a neophallus implant 1050. The neophallus implant 1050 includes a distal tubular portion 1052, a first proximal portion 1054, a second proximal portion 1056, and a transfer joint 1058 connected between the distal tubular portion 1052 and the first and second proximal portions 1054, 1056. Embodiments of a neophallus implant 1050 provide a bifurcated set of proximal portions that communicate with the distal tubular portion 1052. In one embodiment, the bifurcated neophallus implant 1050 is symmetric about a longitudinal axis centered on the distal tubular portion 1052.

In one embodiment, the distal tubular portion 1052 is provided as an inflatable penile prosthetic having a first inflatable cavity coupled along a septum 1060 to a second inflatable cavity. In one embodiment, the distal tubular portion 1052 has one and only one inflatable cavity. The distal tubular portion 1052 is suitably provided as a single cavity that is inflatable with liquid, or alternatively, with two inflatable cavities that are joined along the septum 1060. The distal tubular portion 1052 extends from the transfer joint 1058 to a distal end portion 1062. The distal tubular portion 1052 is adapted for insertion into the neophallus tissue to provide the neophallus with an erection that is suitable for penetrative intercourse.

The natal male penis has a first (left side) corpus cavernosum and a second (right side) corpus cavernosum, where the corpora cavernosa are separated by a septum. Neither of the embodiments above (two inflatable cavities or a single cavity) are appropriate for implantation into a natal male because of the dual and separate nature of the natal male corpora cavernosa could not receive the distal portion of the device inside of the penis. The natal male also has a pair of crura, and each crus diverges away from the midline of the patient in the proximal direction and is attached to the ischiopubic ramus. The diverging nature of the crura prevents the natal male anatomy from receiving the unitized first and second proximal portions 1054, 1056. Thus, the neophallus implant 1050 is adapted for implantation into the trans-male anatomy and is not appropriate for implantation into the natal male anatomy.

The first proximal portion 1054 extends from a first rear tip portion 1064 to the transfer joint 1058 and includes a liquid port 1066. The rear tip portion 1064 is adapted to secure the implant 1050 to the pelvis of a trans-male. The liquid port 1066 is configured for attachment to a reservoir holding a volume of liquid and a pump adapted to move the liquid out of the reservoir. A suitable reservoir and a suitable pump are described above in FIG. 54.

The second proximal portion 1056 extends from a second rear tip portion 1074 to the transfer joint 1058 and includes a second liquid port 1076. The second liquid port 1076 is also configured for attachment to a reservoir holding a volume of liquid and a pump adapted to move the liquid out of the reservoir. A suitable reservoir and a suitable pump are described above in FIG. 54.

The transfer joint 1058 includes a distal end 1080 coupled with the distal tubular portion 1052, a first proximal end 1082 connected to the first proximal portion 1054, a second proximal end 1084 connected with the second proximal portion 1056, and a fixed bend 1090 that is configured to orient the first proximal portion 1054 of the implant 1050 at a pubic arch angle of 110 degrees or less relative to the second proximal portion of the implant 1056. In one embodiment, the fixed bend 1090 in the transfer joint 1058 has the effect of orienting the first proximal portion 1054 at an angle in a range from 80-110 degrees relative to the second proximal portion 1056, where this angle conforms with the generally wider female pubic arch of the trans-male pelvis. In contrast, the natal male pelvis has a pubic arch angle of approximately 60 degrees.

In one embodiment, a diameter of the distal tubular portion 1052 of the implant 1050 is larger than a dimeter of the first proximal portion 1054 and a diameter of the second proximal portion 1056. One effect of this diameter relationship is to provide the trans-male neopenis with an enhanced girth while also affording comfort along the internally implanted (and narrower diameter) proximal portions 1054, 1056.

In one embodiment, one or more attachment tabs 1086 is provided on one or both of the proximal portions of the implant. In one exemplary embodiment, attachment tabs 1086 are secured to a portion of the transfer joint 1058, the second rear tip portion 1074, and at a location between the transfer joint 1058 and the rear tip portion 1074. The surgeon will use the attachment tabs 1086 for securing the implant 1050 to the tissue of the pelvis. In one embodiment, the attachment tabs 1086 are provided with suture eyelets 1088 that are positioned to allow the surgeon to suture the implant 1050 to the tissue structure of the pelvis. Although attachment tabs 1086 are illustrated on the second proximal portion 1056, it is to be understood that embodiments include attachment tabs provided on both of the proximal portions 1054, 1056 and along at least two sides of the transfer joint 1058.

The neophallus implant 1050 is a Y-shaped penile prosthetic, where a body 1092 of the transfer joint 1058 includes the fixed bend 1090 that is adapted to orient the distal tubular portion 1052 in the same or similar conformation of a natal male penis of the male pelvis. The Y-shaped penile prosthetic 1050 includes the first proximal portion 1054 that is attachable to one of the descending pubic rami of the patient, and the second proximal portion 1056 that is attachable to another of the descending pubic rami of the patient, with the transfer joint 1058 adapted to support and orient the distal tubular portion 1052 in a cis-male orientation configured for penetrative intercourse.

The neophallus implants 1000, 1050 are suitably fabricated to be a monolithic, one-piece component. For example, the bifurcated neophallus implant 1050 is fabricated from a single thin-walled polymer suitably reinforced by the transfer joint 1058 to include the bifurcated angle. In an alternative embodiment, the neophallus implants 1000, 1050 are suitably constructed from discrete components, for example an inflatable distal portion coupled to the transfer joint, and a proximal portion coupled to another side of the transfer joint, where the proximal portion is either inflatable, or a rigid malleable (non-inflatable) structure.

Figure 59A:
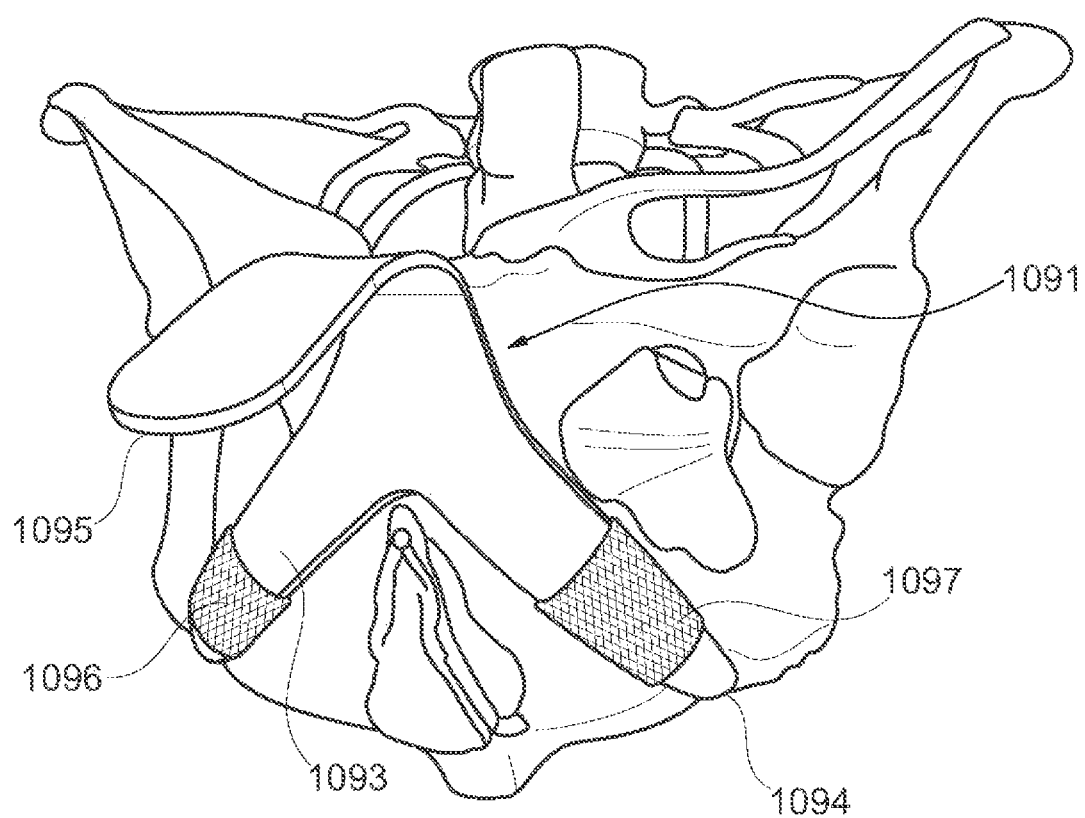
FIG. 59A is a schematic view of one embodiment of an implantable place holder implanted into a trans-male pelvis.

FIG. 59A illustrates one embodiment of implanting the Y-shaped neophallus implant 1050 (FIG. 58). In one embodiment, and implantation space is created during the phalloplasty, where the implantation space is sized to receive the Y-shaped neophallus implant 1050 (FIG. 58) or the Y-shaped neophallus implant 1120 (FIG. 60C). The surgeon may choose to have a period of between several weeks to several months between the creation of the phalloplasty and the implantation of the neophallus implant. Embodiments described provide a method of maintaining the space created during the phalloplasty to allow for implantation of one of the described the neophallus implants into that space. This approach reduces or eliminates coring out (or dilation) of the neophallus. Dilating the tissue within the neophallus can give rise to undesirable outcomes such as perforating the neourethra, damaging the nurse within the neophallus, or puncturing a wall of the neophallus.

In one embodiment, a place holder 1091 is implanted after formation of the neophallus. The place holder 1091 includes a first proximal portion 1093 and a second proximal portion 1094 diverging from a body 1095. The first proximal portion 1093 is sized and shaped to maintain a space sized to receive the first proximal portion 1054 of the neophallus implant 1050 (FIG. 58) and the second proximal portion 1095 is sized and shaped to maintain a space sized to receive the second proximal portion 1056 of the neophallus implant 1050. The first and second proximal portions 1054, 1056 of the neophallus implant 1050 are generally cylindrical, and embodiments of the place holder 1091 include a cylindrical shape for the first and second proximal portions 1093, 1094. The body 1095 is a lateral dimension that is generally larger than the first and second proximal portions 1093, 1094 and is sized to maintain a shape within the neophallus that will receive the increased with of the distal portion 1052 of the neophallus implant 1050. In some embodiments, the body 1095 has a rectangular cross-section, and in other embodiments, the body 1095 has an oval or circular cross-sectional sheet.

The surgeon implants the place holder 1091 into the trans-male pelvis after forming the neophallus. In one embodiment, the surgeon connects an artificial crus penis recess 1096 to the descending ramus on the patient's right hand side and a second artificial crus penis recess 1097 to the descending ramus on the patient's left hand side. The first proximal portion 1093 of the place holder 1091 is inserted into the artificial crus penis recess 1096 and the second proximal portion 1094 of the place holder 1091 is inserted into the artificial crus penis recess 1097. The body 1095 is inserted and implanted into the neophallus.

In one embodiment, the place holder 1091 is implanted into the trans-male pelvis after forming the neophallus without the aid of artificial recesses or attachment devices. For example, instructions are provided directing the surgeon to dissect the tissue down to the muscle that is attached to each descending ramus and to subsequently form a pocket with the subcutaneous tissue. The place holder 1091 is inserted into the pockets formed under the subcutaneous tissue and over the muscle on the ramus, and into the neophallus. Thus, the artificial crus penis recesses 1096, 1097 are optional.

The place holder 1091 reduces or eliminates the growth of tissue into the space where the neophallus implant 1015 will be implanted. After implantation of the place holder 1091, tissue will grow around the place holder 1091 to form a tissue capsule in the shape of the place holder 1091, which is also the shape of the neophallus implant 1050. After suitable period for healing, the surgeon removes the place holder 1091 to access the tissue capsule. The neophallus implant 1050 is inserted into the tissue capsule, which is sized and shaped receive the neophallus implant 1050. The artificial crus penis recesses 1096, 1097 are encapsulated in the tissue capsule to more closely represent the crus penis recess of a natal male. The place holder 1091 obviates the tissue dilation that can lead to the undesirable consequences identified above.

It is desirable that the tissue capsule form around the place holder 1091 and not attach to the surface of the place holder 1091. Embodiments include incorporating a tissue release complement under the place holder 1091. Alternatively, the place holder 1091 is formed or silicone, to which the tissue is unlikely to adhere.

Figure 59B:
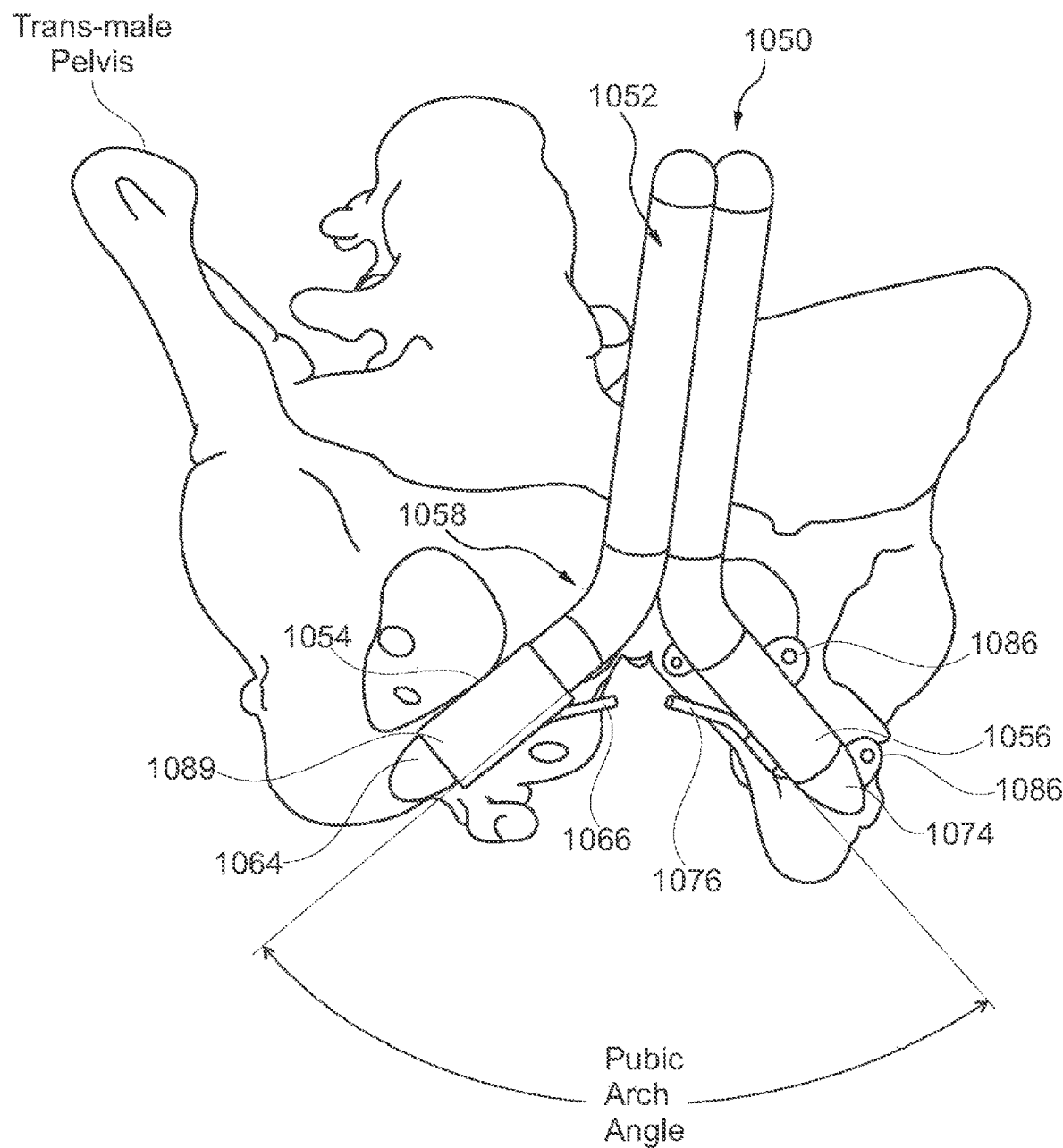
FIG. 59B is a schematic view of the neophallus implant illustrated in FIG. 58 implanted in a space formed by the implantable place holder within the pelvis of a trans-male.

FIG. 59B is a schematic view of another embodiment of an approach for implanting the neophallus implant 1050 in a trans-male pelvis by securing the attachment tabs 1086 and the fabric 1089 to the trans-male pelvis. The first proximal portion 1054 is secured to the descending ramus on the right side of the patient and a second proximal portion 1056 is secured to the descending ramus on the left side of the patient. Suitable approaches for connecting the proximal portions 1054, 1056 include sutures placed through the rear tip portions 1064, 1074, for example by employing the attachment tabs 1086, or any of the implantable supports described above that provide an artificial crus penis recess. The first proximal portion 1054 has been secured to the descending ramus on the right side of the patient using the fabric 1089. The second proximal portion 1056 has been secured to the descending ramus on the left side of the patient by suturing through the attachment tabs 1086. The transfer joint 1058 is coupled to the first and second proximal portions 1054, 1056 and supports the distal tubular portion 1052 in a position relative to the trans-male pelvis that mirrors the position of the penis of a cis-male. The liquid ports 1066, 1076 are attachable to the liquid reservoir and the pump. The liquid reservoir is typically implanted somewhere within the abdomen, and the pump is implanted in a neoscrotum.

In one exemplary embodiment, one or both proximal portions 1054, 1056 are secured to a descending ramus with a fabric 1089 that is wrapped around one or both of the proximal portions 1054, 1056 and secured to the tissue of the pelvis. Suitable fabrics include synthetic mesh fabrics that are porous and allow for tissue ingrowth. One suitable fabric is RESTORELLE® Flat Mesh available from Coloplast Corp., Minneapolis, Minn. Another suitable fabric is the GORE-TEX® synthetic permeable membrane available from W. L. Gore & Associates.

The transfer joint 1058 provides a Y-shaped transfer joint. When assembled as illustrated, the neophallus implant 1050 provides a Y-shaped inflatable penile prosthetic. The neophallus implant 1050 is inflatable through the ports 1066, 1076. The Y-shaped geometry of the neophallus implant 1050 constrains movement of the implanted neophallus system since the fixed bend 1090 is supported by tissue under and around the fixed bend 1090. The support provided by the tissue under the fixed bend 1090 interferes with movement of the implanted neophallus system, one advantage of which is to provide resistance to the axial thrust associated with penetrative intercourse. The tissue under the fixed bend 1090 holds and supports the neophallus implant 1050 after implantation and healing by the patient.

Figure 60A:
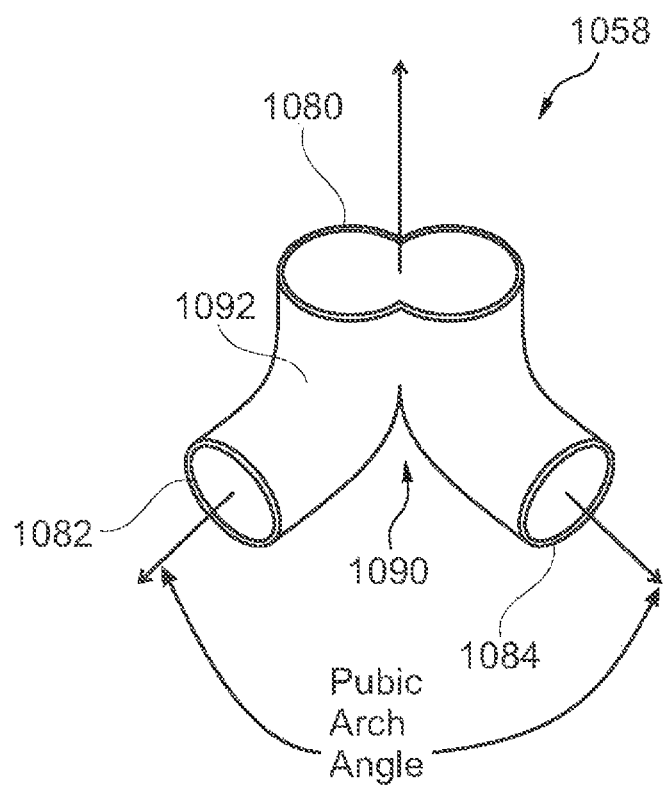
FIG. 60A is a perspective view of one embodiment of a transfer joint adapted for use with a neophallus implant having dual penile prosthetic distal portions.

FIG. 60A is a perspective view of one embodiment of the transfer joint 1058. The transfer joint 1058 includes the body 1092 that extends between the distal end 1080, the first proximal end 1082, and the second proximal end 1084. In one embodiment, the transfer joint 1058 is a Y-shaped joint for the body 1092 extends continuously between the distal end 1080 and the first and second proximal ends 1082, 1084 to provide the fixed bend 1090 that is selected to have a pubic arch angle adapted to match the pubic arch angle of the trans-male pelvis.

Figure 60B:
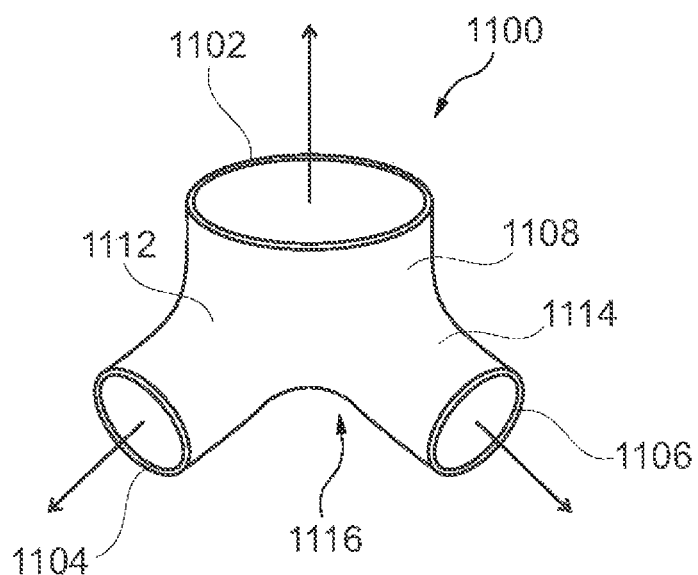
FIG. 60B is one embodiment of a transfer joint adapted for use with a neophallus implant having a single penile prosthetic distal portion.
Figure 60C:
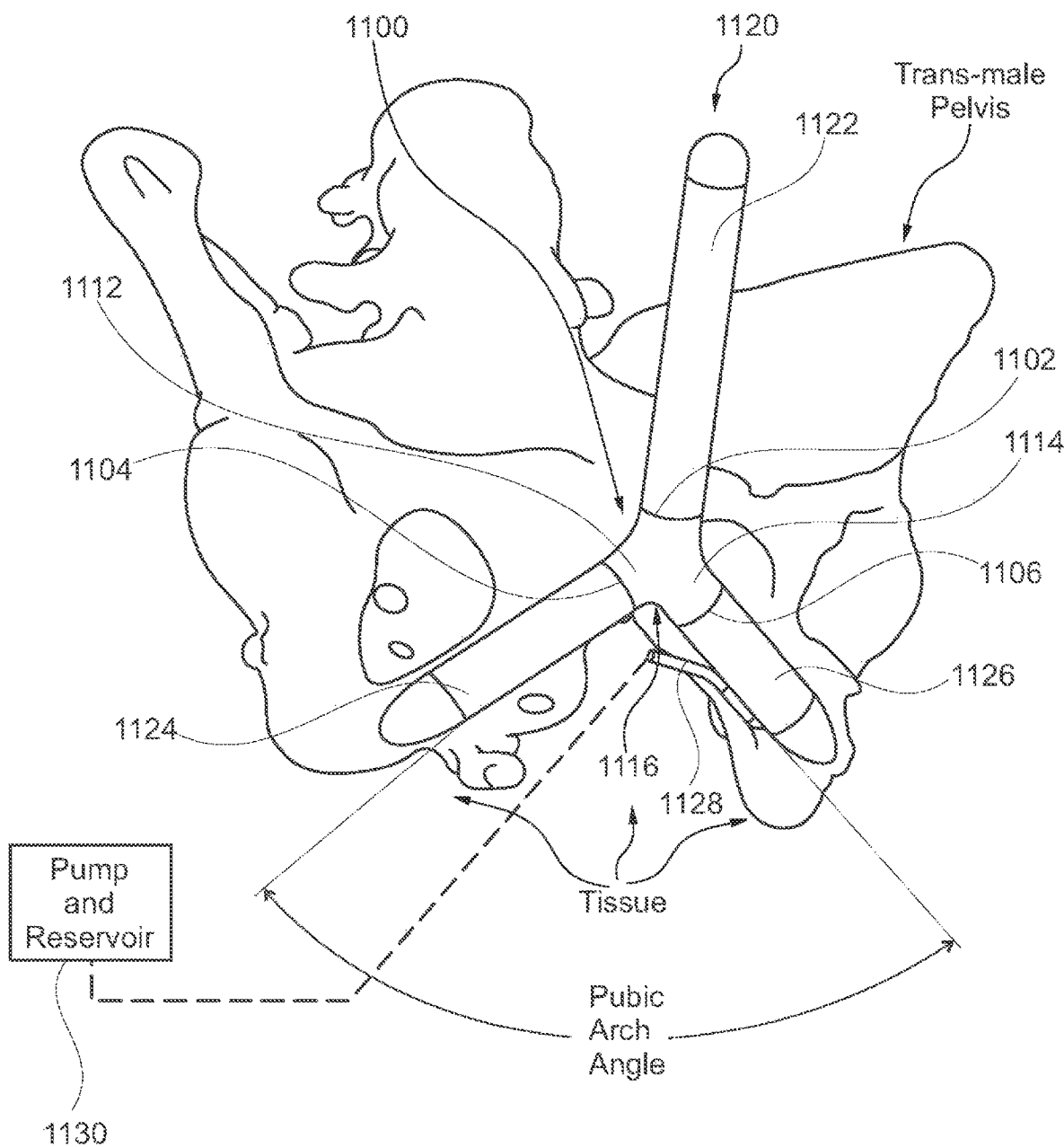
FIG. 60C is a schematic view of one embodiment of a neophallus implant implanted in a trans-male pelvis.

FIG. 60B is a perspective view of one embodiment of a transfer joint 1100. The transfer joint 1100 includes a distal end 1102, a first proximal end 1104, and a second proximal end 1106. The transfer joint 1100 includes a body 1108 that extends continuously between the distal end 1102 and the first and second proximal ends 1104, 1106. The transfer joint 1100 is configured as a Y-shaped transfer joint having a first branch 1112 oriented relative to a second branch 1114 by a fixed bend 1116.

The distal end 1102 has a diameter that is sized to receive a distal penile prosthetic. The first and second proximal ends 1104, 1106 each have a diameter that is sized to couple with a proximal portion. The transfer joint 1100 provides an implantable portion for a trans-male that provides a wider girth distal penile prosthetic (as compared to the girth of a penile prosthetic of a natal male that is sized to fit inside of a corpus cavernosum). The transfer joint 1100 has first and second proximal ends 1104, 1106 that receive proximal portions of the implant, and it is desired that the proximal portions are fixated relative to the pubic body, or rami. In one embodiment, the diameter of the distal end 1102 is larger than either diameter of the first and second proximal ends 1104, 1106, one effect of which is to provide enhanced girth to the distal portion of the implant and increased comfort of the proximal portions of the implant.

FIG. 60C is a schematic view of one embodiment of a neophallus implant 1120 implanted in a trans-male pelvis. The neophallus implant 1120 includes a distal portion 1122 coupled to the distal end 1102 of the transfer joint 1100, a first proximal portion 1124 coupled to the first proximal end 1104 of the transfer joint 1100, and a second proximal portion 1126 coupled to the second proximal end 1106 of the transfer joint 1100. At least the distal portion 1122 is an inflatable penile prosthetic and is inflated through the port 1128. The liquid port 1128 is connected to one of the first proximal portion 1124 or the second proximal portion 1126. In one embodiment, the implant 1120 is monolithically formed as a single unit to include the transfer joint 1100, the distal portion 1122, the first proximal portion 1124, and the second proximal portion 1126. For example, the distal portion is formed as a thin walled polymer sheet that is connected to the transfer joint 1100, and the first and second proximal portions, whether inflatable or not inflatable, are connected to the proximal ends of the transfer joint 1100. In one embodiment, the distal portion 1122 and the first and second proximal portions 1124, 1126 are provided as tubular cylinders and are inflatable through the port 1128. The port 1128 is adapted to be attached to a reservoir at 1130 holding a volume of liquid and a pump at 1130 provided to move the liquid out of and into the pump. One suitable pump P and one suitable reservoir R are described above in FIG. 3 and are available from Coloplast Corp., Minneapolis, Minn. In one embodiment, the distal portion 1122 is inflatable through the port 1128 and the first and second proximal portions 1124, 1126 are not inflatable but are formed to have a solid cross-section having an interior channel formed in the solid portion, where the channel communicates between the port 1128 and the inflatable distal portion 1122.

In one embodiment, the distal portion 1122 is an inflatable penile prosthetic and the first and second proximal portions 1124, 1126 are not inflatable. In one embodiment, the distal portion 1122 of the implant 1120 is an inflatable penile prosthetic having one and only one inflatable cavity.

In one embodiment, the first and second proximal portions 1124, 1126 are solid components having a circular lateral cross-sectional shape that tapers to a narrower proximal end. In this case, the port 1128 is moved in a distal direction and attached to one of the transfer joint 1100 or to the distal portion 1122. In one embodiment, the first and second proximal portions 1124, 1126 have a flat profile that is rectangular in cross-section, where the flat profile adapts the first and second proximal portions 1124, 1126 to lay flat against the muscle that is attached to the ramus.

The transfer joint 1100 provides a Y-shaped transfer joint having the first branch 1112 oriented relative to the second branch 1114 by the fixed bend 1116. When assembled as illustrated, the neophallus implant 1120 provides a Y-shaped inflatable penile prosthetic. The neophallus implant 1120 is inflatable through a single port 1128, which is an advantage over the dual port neophallus implant 1050 (FIG. 59B) since fewer parts are employed. In one embodiment, the fixed bend 1116 in the transfer joint 1100 orients the first proximal portion 1124 at an angle in a range from 80-110 degrees relative to the second proximal portion 1126 to adapt the first proximal portion 1124 and the second proximal portion 1126 of the implant 1120 to align with a female pubic arch. The angle is shown as a pubic arch angle for a trans-male pelvis. The Y-shaped geometry of the neophallus implant 1120 constrains movement of the implanted neophallus system since the fixed bend 1116 is supported by tissue under and around the fixed bend 1116. The support provided by the tissue (subcutaneous or perineal) under the fixed bend 1116 interferes with movement of the implanted neophallus system, one advantage of which is to provide resistance to the axial thrust associated with penetrative intercourse. One advantage of this tissue-style of support is that the attachment tabs 1086 (FIG. 59B) and the fabric 1089 (FIG. 59B) is not used to achieve firm fixation. One effect of adapting the neophallus implant 1120 to be implanted and supported by the tissue within the fixed bend 1116 is that the implantation procedure is simplified since no suture attachments or other fixation devices are used. If the surgeon determines that the neophallus implant 1120 should later be removed, there are no suture attachments or other fixation devices to be cut or dissected. The neophallus implant 1120 is implanted with the first and second proximal portions 1124, 1126 inserted into a tissue pocket alongside the rami without using attachment devices or fixation. The tissue under the fixed bend 1116 holds and supports the neophallus implant 1120 within the trans-male pelvis without sutures or fabric wraps.

One method of implantation includes forming a neophallus in a phalloplasty procedure. The neophallus implant 1120 is implanted in the neophallus by inserting the distal portion 1122 into the neophallus and inserting the first and second proximal portions 1124, 1126 alongside each ramus, respectively, between the muscle attached to the ramus and the tissue over the muscle. The surgeon may dissect or dilate tissue along each ramus to form a pocket that is sized to receive each of the first and second proximal portions 1124, 1126.

In an alternative method, a neophallus and the surgeon forms a tissue pocket over the muscle attached to each ramus and the tissue over the muscle. The place holder 1091 (FIG. 59A) is inserted into each of the tissue pockets and the neophallus, for example with each of the first and second proximal portions 1093, 1094 located in one of the respective tissue pockets and the distal portion 1095 located in the neophallus. The surgical site is allowed to heal. The surgeon surgically removes the place holder 1091 to reveal openings formed in each tissue pocket alongside each ramus and within the neophallus. The neophallus implant 1120 is inserted into the open tissue pockets with the first and second proximal portions 1124, 1126 placed in the tissue pockets alongside of each descending ramus and the distal portion 1122 placed in the opening formed in the neophallus. The surgeon may opt to use a tool to push the first and second proximal portions 1124, 1126 into the tissue pockets formed alongside of the rami. Suitable tools include blunt-styled pushing devices such as the flat blade Boyarskogo or Petrovsky tools. A suitable tool for placing the distal portion 1122 includes the flat bladed pushing tools or a Furlow-style of device that employs a Keith needle to place a penile prosthetic into penile tissue.

One aspect of the method includes forming the fixed bend 1116 in the transfer joint 1100 at a pubic arch angle to align the first proximal portion 1124 of Y-shaped inflatable implant 1120 and the second proximal portion 1126 of Y-shaped inflatable implant with a pubic arch of the trans-male pelvis.

The pump and reservoir 1130 are implanted, for example with the pump located in the neoscrotum and the reservoir implanted subcutaneously or inside of the abdomen. The pump and the reservoir are connected to the port 1128 and the distal portion 1122 of the neophallus implant 1120 is inflated to ensure appropriate operation of the implanted device. The patient is allowed to heal. The Y-shaped geometry of the neophallus implant 1120 limits or prevents movement of the implanted neophallus system (implant 1120 and pump/reservoir 1130) since the fixed bend 1116 is supported by tissue under and around the fixed bend 1116. The support provided by the tissue (subcutaneous or perineal) under the fixed bend 1116 interferes with movement of the implanted neophallus system, one advantage of which is to provide resistance to the axial thrust associated with penetrative intercourse.

Figure 61:
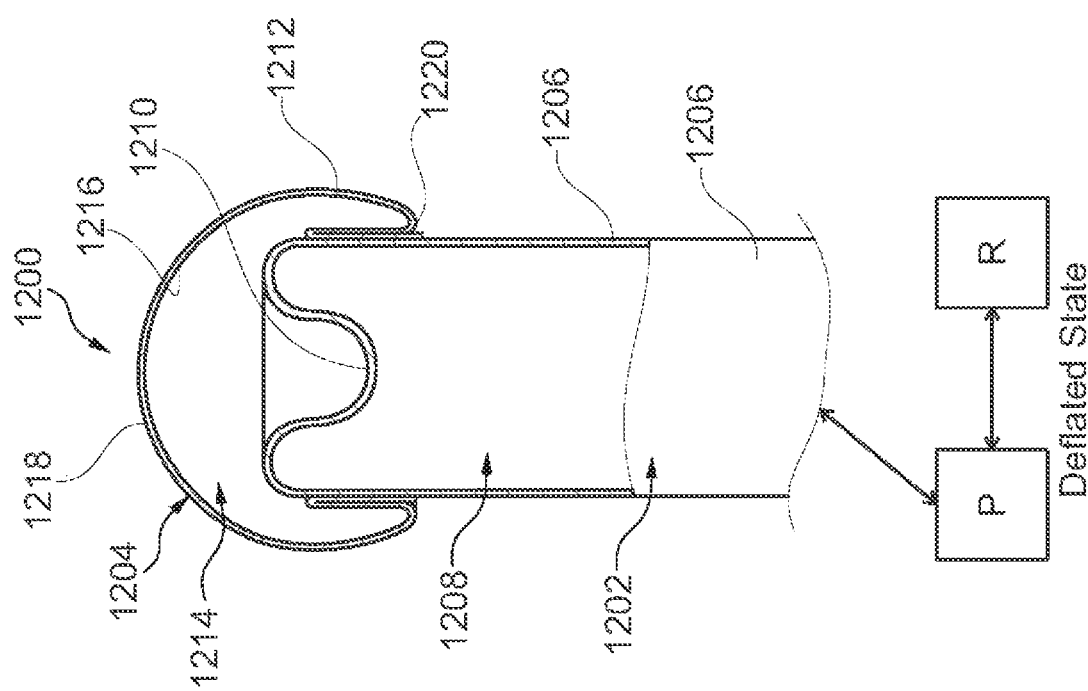
FIG. 61 is a partial cross-sectional view of one embodiment of a deflated neophallus implant.

FIG. 61 is a partial cross-sectional view of one embodiment of a neophallus implant 1200. The neophallus implant 1200 includes an inflatable body 1202 and an artificial glans penis 1204 coupled to the inflatable body 1202. The inflatable body 1202 includes a wall 1206 that defines a cavity 1208. The pump P is operable to move liquid stored in the reservoir R into the cavity 1208 to inflate the inflatable body 1202. The liquid is retained in the reservoir and the illustration of FIG. 61 such that the inflatable body 1202 is deflated. The inflatable body 1202 includes a distal tip 1210 that is configured to move between an inverted shape, as illustrated, to an erect state. One suitable pump P and a reservoir R are described above in FIG. 3 and is available from Coloplast Corp., Minneapolis, Minn.

The artificial glans penis 1204 includes a wall 1212 that defines a cavity 1214. The wall 1212 includes an interior surface 1216 and an exterior surface 1218. The wall 1212 is folded on itself and the exterior surface 1218 is bonded to an exterior surface of the wall 1206 to form a hem 1220. The artificial glans penis 1204 is separate from and sealed against the inflatable body 1202 such that the artificial glans penis 1204 is not in fluid communication with the inflatable body 1202.

In one embodiment, the reservoir R is filled with saline or other liquid that is movable by the pump P into and out of the inflatable body 1202. One suitable pump P and reservoir R are described above in FIG. 3 both are available from Coloplast Corp., Minneapolis, Minn.

The cavity 1214 is filled with a liquid. In one embodiment, the cavity 1214 is filled with a gel. When inflatable body 1202 is pressurized, the distal tip 1210 moves into a portion of the cavity 1214 to displace a portion of the gel, which increases the firmness of the artificial glans penis 1204. In this manner, the tumescence that occurs within the glans penis of a natal male penis is artificially replicated in a neophallus implant that is suitable for implantation into a trans-male. One suitable gel is a silicone gel. Other suitable gels include gels formed from hydrocolloids.

Figure 62:
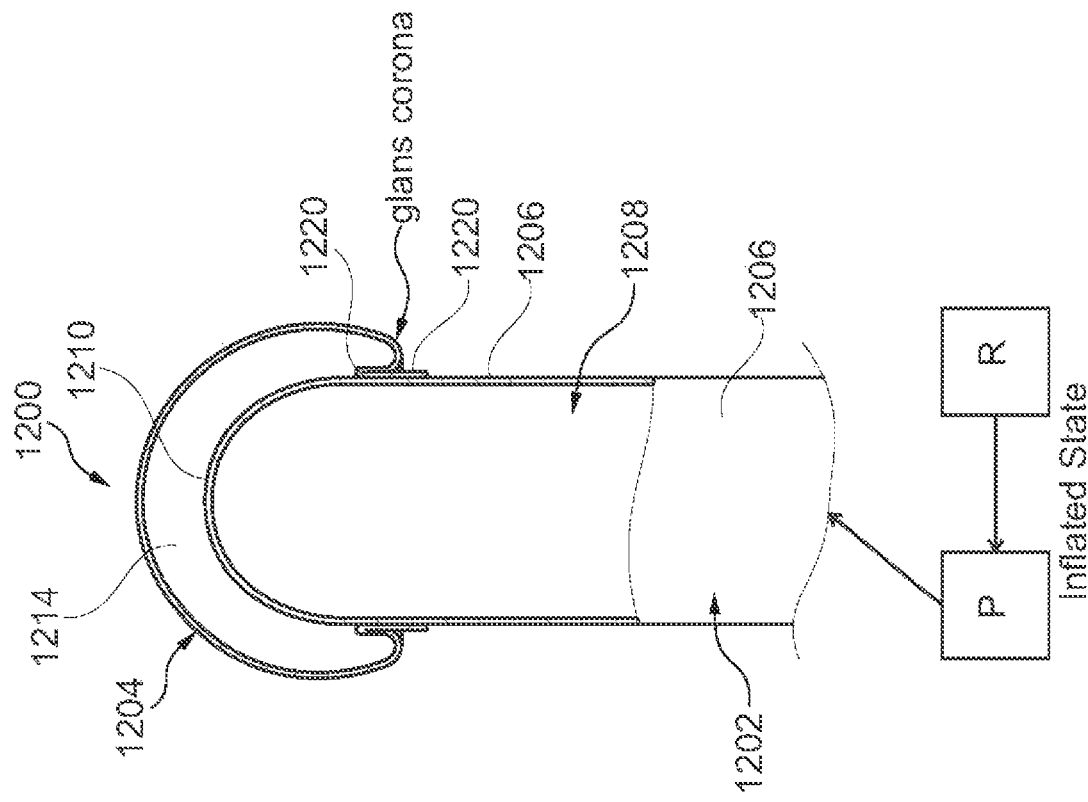
FIG. 62 is a partial cross-sectional view of the neophallus implant illustrated in FIG. 61 after inflation.

FIG. 62 is a partial cross-sectional view of the neophallus implant 1200 after the liquid has been moved from the reservoir R into the inflatable body 1202. The pressure inside of the cavity 1208 is thus increased, which results in an inflation and expansion of the wall 1206. The expansion of the wall 1206 causes the distal tip 1210 to move in a distal direction into the cavity 1214 of the artificial glans penis 1204. The artificial glans penis 1204 becomes firm and forms a glans corona adjacent to hem 1220. The firmness of the artificial glans penis 1204 is controlled by controlling the pressure inside of the inflatable body 1202, the elasticity of the wall 1204, the volume within the cavity 1214, and the amount of expansion of the distal tip 1210 into the artificial glans penis 1204.

The artificial glans penis 1204 provides the means for reducing or preventing erosion of a neophallus implant through a neophallus of a trans-male. The artificial glans penis 1204 provides the means for increasing the girth of the distal portion of a neopenis implanted in a trans-male.

Figure 63:
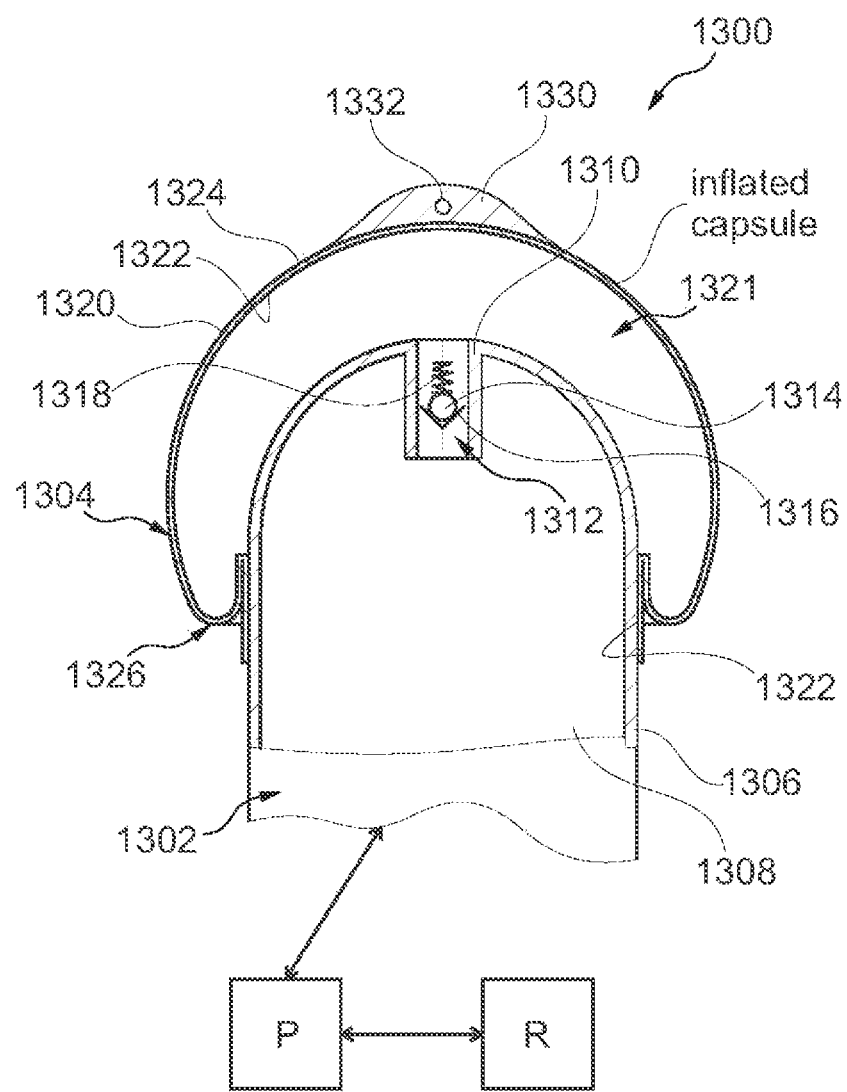
FIG. 63 is a partial cross-sectional view of one embodiment of a neophallus implant.

FIG. 63 is a partial cross-sectional view of one embodiment of a neophallus implant 1300. The neophallus implant 1300 includes an inflatable body 1302 coupled to an artificial glans penis 1304. The inflatable body 1302 includes a wall 1306 that defines a liquid receptacle, or cavity 1308, and terminates at a distal tip 1310. The artificial glans penis 1304 is in fluid communication with the inflatable body 1302 by the valve 1312. The valve 1312 includes a ball 1314 that is biased against a valve seat 1316 by a spring 1318. In one embodiment, the valve 1312 is a check valve that includes a selected cracking pressure. The pump P is operable to move liquid out of the reservoir R and into the inflatable body 1302 to thus increase the pressure within the cavity 1308. The cracking pressure of the valve 1312 is selected to open within the pressure range of the inflation of the inflatable body 1302 to allow liquid to move from the cavity 1308 and into the artificial glans penis 1304. In one embodiment, the inflatable body 1302 is inflatable to a pressure in a range from 5-20 pounds per square inch (34-138 kPa) and the cracking pressure is selected to be of value that is less than the inflatable pressure within the cavity 1308. As one example, the inflatable body 1302 is inflatable to a pressure of approximately 15 pounds per square inch (103 kPa) and the cracking pressure of the valve 1312 is selected to be approximately 10 pounds per square inch (69 kPa).

The artificial glans penis 1304 includes a wall 1320 defining a cavity 1321, where the wall 1320 includes an interior surface 1322 and an exterior surface 1324. In one embodiment, the wall 1320 is folded on itself to form a hem 1326, for example by folding a portion of the wall 1320 onto itself and sealing the interior surface 1322 to an exterior surface of the wall 1306. The neophallus implant 1300 is adapted for implantation into the tissue of a neophallus, and an embodiment includes providing the surgeon with a nub 1330 having a hole 1332 that allows the surgeon to push or direct the artificial glans penis 1304 into a distal portion of the neophallus.

The artificial glans penis 1304 is in fluid communication with the cavity 1308. One consequence of this is that the neophallus implant 1300 is self-contained and the artificial glans penis 1304 is eventually filled with whatever liquid is employed to inflate the inflatable body 1302. Thus, no fill port or other valve structure is needed to fill the artificial glans penis 1304 with liquid.

The artificial glans penis 1304 provides the means for reducing or preventing erosion of a neophallus implant through a neophallus of a trans-male. The artificial glans penis 1304 provides the means for increasing the girth of the distal portion of a neopenis implanted in a trans-male.

Figure 64:
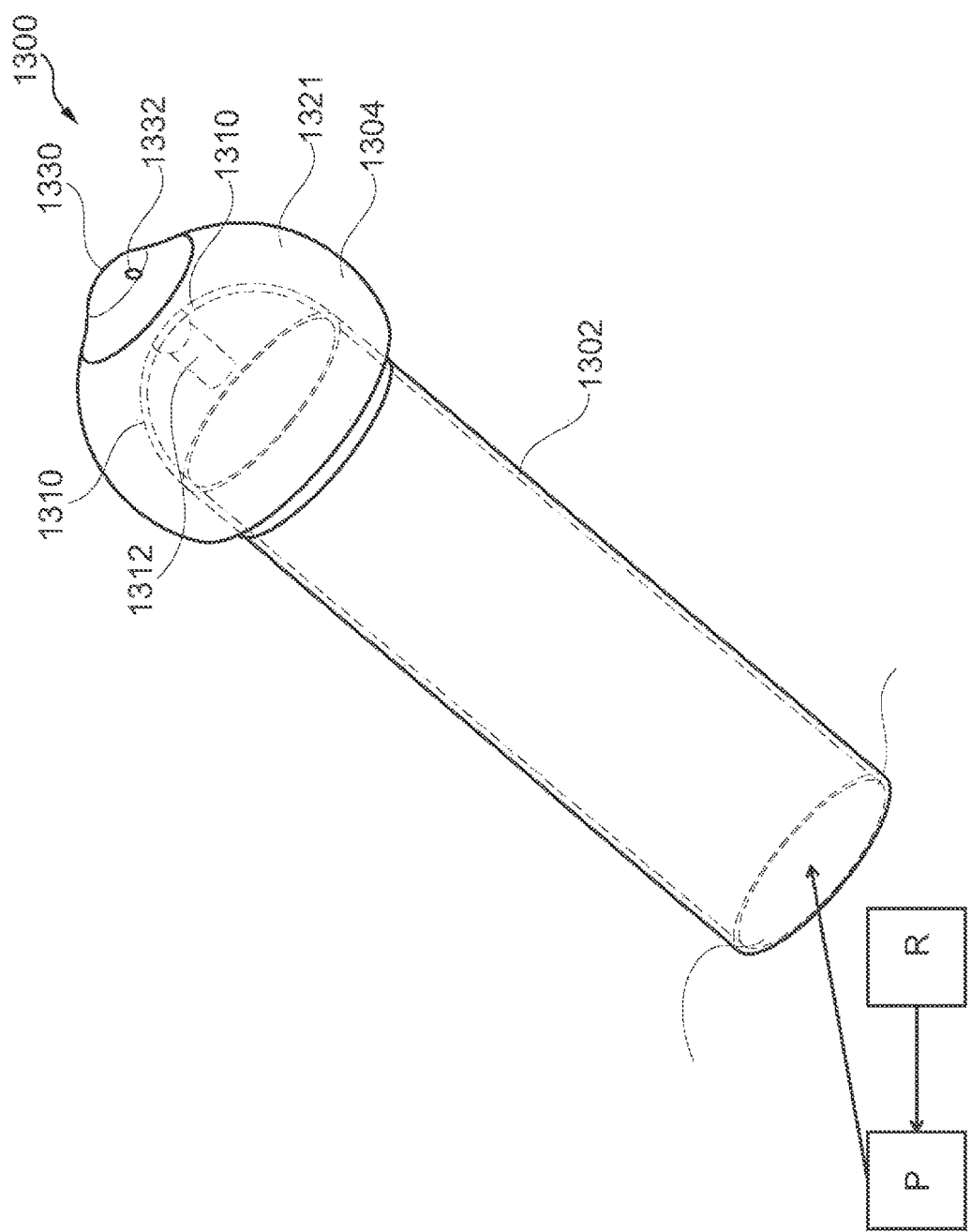
FIG. 64 is a perspective view of the neophallus implant illustrated in FIG. 63.

FIG. 64 is a perspective view of the neophallus implant 1300 inflated with liquid to provide an erection. The liquid contained in the reservoir R has been moved by the pump P into the inflatable body 1302. The increasing pressure in the inflatable body 1302 displaces the distal tip 1310 in a distal direction and delivers liquid through the valve 1312 and into the artificial glans penis 1304. The pump P operates to inflate both the inflatable body 1302 and the artificial glans penis 1304. The neophallus implant 1300 is adapted to be deflated to a flaccid state, and during deflation of the inflatable body 1302 the pressure inside of the cavity 1321 will be reduced as the distal tip 1310 inverts.

The artificial glans penis 1204 (FIG. 61) and 1304 (FIG. 63) are provided in a dome shape that provides the distal end of the neophallus with a firm and expandable artificial glans penis.

Figure 65:
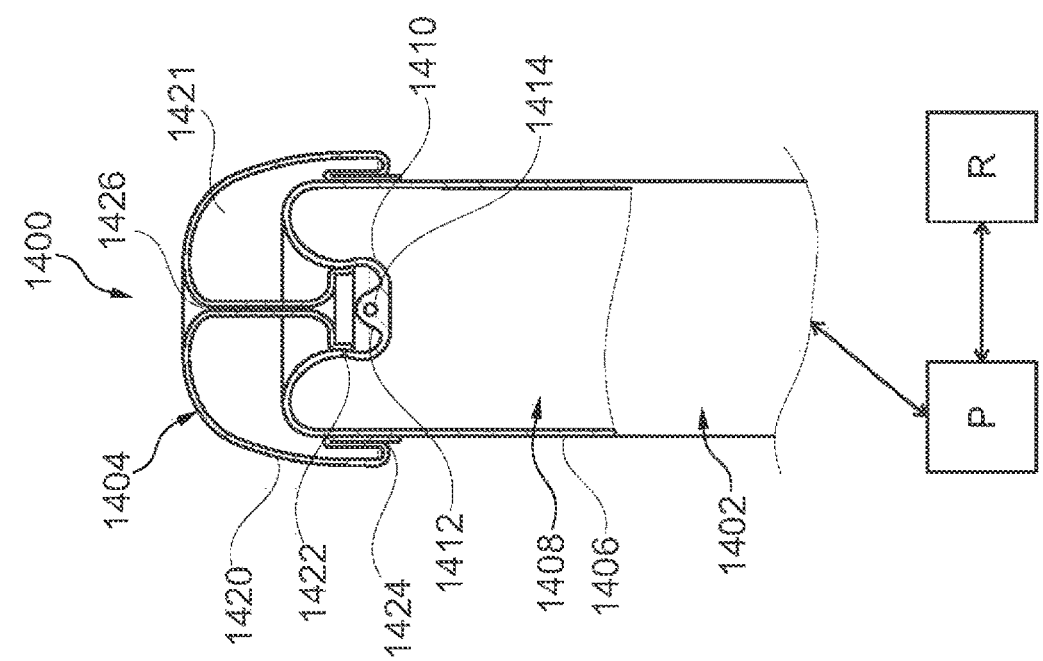
FIG. 65 is a partial cross-sectional view of one embodiment of a deflated neophallus implant.

FIG. 65 is a partial cross-sectional view of one embodiment of a neophallus implant 1400. The neophallus implant 1400 includes an inflatable body 1402 coupled to an artificial glans penis 1404. The inflatable body 1402 includes a wall 1406 that defines a cavity 1408 and terminates in a distal tip 1410. A nub 1412 is provided at the distal tip 1410 and includes a suture hole 1414 to facilitate implantation of the implant 1400 into a neophallus. The nub 1412 is coupled to a portion of the inflatable body 1402 to provide the surgeon with a familiar implantation feature.

The artificial glans penis 1404 includes a wall that forms a cavity 1421, where the wall 1420 is attached to the inflatable body 1402 at a distal seam 1422 and at a proximal seam 1424. The attachment of the artificial glans penis 1404 along the to seams 1422, 1424 forms a generally annular shape that forms a suture channel 1426. The artificial glans penis 1404 is sealed such that the cavity 1421 is separated from the cavity 1408. The inflatable body 1402 is inflatable with liquid moved by the pump P out of the reservoir R. Inflation of the inflatable body 1402 will expand the distal tip 1410 and increase the pressure within the cavity 1421.

Figure 66:
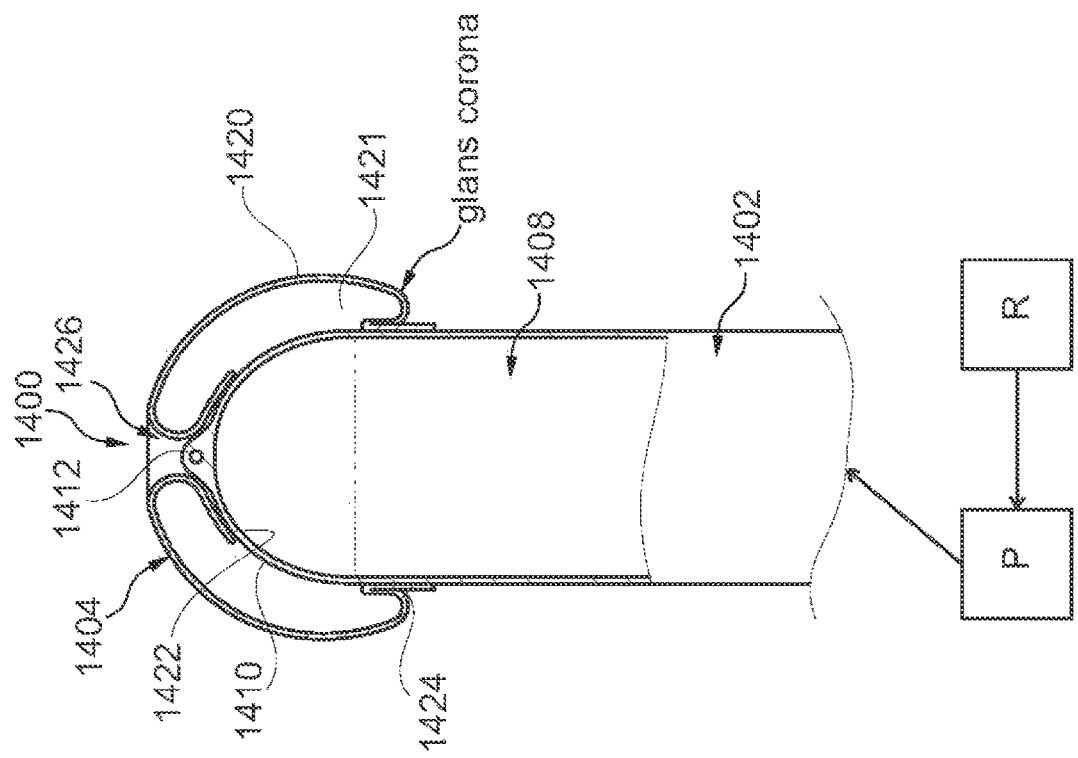
FIG. 66 is a partial cross-sectional view of the neophallus implant illustrated in FIG. 65 after inflation.

FIG. 66 is a partial cross-sectional view of the neophallus implant 1400 inflated with liquid. The liquid has been moved from the reservoir R into the inflatable body 1402 by the pump P. The increased pressure in the inflatable body 1402 displaces the distal tip 1410 in a distal direction to subsequently displace the annular artificial glans penis 1404 to form a glans corona. Expansion of the annular artificial glans penis 1404 expands and opens the suture channel 1426 in a manner that protectively covers the nub 1412 by extending a longitudinal distance past the nub 1412.

One method of providing a trans-male with a neopenis includes inverting the vagina to create a neophallus. The method includes dissecting tissue to disconnect the internal organs (cervix, uterus) and connective tissue from the vagina to form a complete prolapse of the vagina. One step includes removing the cervix from the apex of the vagina. Alternatively, the cervix is not removed from the vagina and tissue from the cervix is shaped into a glans penis.

The tissue of the inverted vagina is employed, in whole or in part, to form the tissue of the neophallus. One of the neophallus implant systems described above, for example system 20, 300, 400, 600, 610, 620, 650, or 700 is implanted within the trans-male with the penile prosthetic implanted within the neophallus, a pump implanted within the neoscrotum, and the reservoir implanted within the abdomen. In one embodiment, the reservoir is implanted within the internal space of the abdomen/pelvis that was previously occupied by the vagina. One alternative step of the method includes adding bulking material around the penile prosthetic to increase the girth of the neopenis. Suitable bulking material includes cadaver tissue, animal tissue, collagen, a collagen sponge, a mesh, a bioabsorbable sponge, synthetic material, or a bioabsorbable material. In one embodiment, the bulking material is pre-shaped to receive the penile prosthetic. In one embodiment, the method includes folding an inferior portion of the tissue of the inverted vagina unto itself (for example, the anterior and interior wall of the vagina); closing a portion of the folded tissue to itself at an inferior (underneath) location; and thus forming a channel that is sized to receive a portion of the urethra or a portion of the neourethra of the trans-male, or both a portion of the urethra and a portion of the neourethra of the trans-male.

Aspects of methods of providing a trans-male with a neopenis include attaching an artificial crus penis recess to the tissue of the pelvis, and supporting the proximal portion of the penile prosthetic by inserting the proximal portion of the penile prosthetic into the artificial crus penis recess.

Aspects of methods of providing a trans-male with a neopenis include forming a tissue pocket alongside of each descending ramus of the pelvis, and supporting the proximal portion of the penile prosthetic by inserting the proximal portion of the penile prosthetic into the tissue pocket.

Aspects of methods of providing a trans-male with a neopenis include forming a glans penis at a distal end of the neopenis with tissue of a cervix.

Aspects of methods of providing a trans-male with a neopenis include metoidioplasty. Metoidioplasty is completed in two stages: testosterone treatment followed by surgery. During the testosterone treatment, the clitoris responds by growing longer. During surgery, the surgeon severs the ligament that holds the clitoris in place under the pubic bone, resulting in "clitoral release" that allows the enlarged clitoris to have the appearance of a small penis. The metoidioplasty is followed by the release of the vagina and inversion of the vagina outside of the pelvis. In one embodiment, a portion of the enlarged clitoris is surgically transported to a distal portion of the inverted vagina to increase sensitivity in this area of the neophallus. The trans-male has a urethra that is approximately 2 cm long, and aspects of the method includes attaching a neourethra to the natal urethra to construct a neourethra through the neophallus.

The glans penis is formed at the distal portion of the inverted vagina, and can include aspects of the artificial glans penis structures described above, or additional tissue formed as a glans corona. A penile prosthetic is implanted within the inverted vagina and can include aspects of the neophallus implant system described above, such as a pump and a reservoir, to facilitate inflation of an inflatable penile prosthetic. The implanted penile prosthetic is secured to the pelvis of a trans-male, for example using one of the artificial crus penis receptacles described above. In this way, the implanted penile prosthetic is supported to resist the axial forces associated with penetrative intercourse and is positioned to appropriately replicate the position of the penis in a natal male.

One exemplary method of surgically creating a neopenis includes dissecting tissue away from a vagina to disconnect the vagina from organs and connective tissue inside of a pelvis; inverting the vagina out of the pelvis to provide an inverted vagina by exposing an interior wall of the vagina outside of the pelvis; inserting a penile prosthetic into the inverted vagina and inside a portion of the pelvis; and supporting a proximal portion of the penile prosthetic by attaching the proximal portion of the penile prosthetic to the pelvis.

The method can include inserting a bulking material and the penile prosthetic into the inverted vagina.

The method can include removing a cervix by dissecting the cervix away from the vagina.

The method can include removing tissue from a cervix and forming a glans penis with the tissue removed from the cervix; and attaching the glans penis to the inverted vagina.

The method can include folding a superior portion of tissue of the inverted vagina and closing the superior portion of tissue of the inverted vagina to a second portion of the inverted vagina thus forming a channel; and placing a portion of a urethra of the trans-male and a portion of a neourethra of the trans-male into the channel.

The method can include inserting a malleable and non-inflatable penile prosthetic into the inverted vagina and inside the portion of the pelvis; and attaching a proximal portion of the malleable and non-inflatable penile prosthetic to a descending ramus of the pelvis.

The method can include inserting an inflatable penile prosthetic into the inverted vagina and inside the portion of the pelvis; attaching a proximal portion of the inflatable penile prosthetic to a descending ramus of the pelvis; coupling a reservoir and a pump to the inflatable penile prosthetic with tubing; and implanting the reservoir and the pump into the trans-male.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

The invention claimed is:

1. A method of surgically providing a trans-male patient with a neopenis, the method comprising:
    dissecting tissue away from at least an apex of a vagina to disconnect the vagina from organs and connective tissue inside of a pelvis;
    inverting the vagina out of the pelvis to provide an inverted vagina by exposing an interior wall of the vagina outside of the pelvis;
    providing a neopenis by inserting an implantable penile prosthesis into the inverted vagina, where the implantable penile prosthesis comprises a pair of malleable penile inserts inside an artificial tunica; and
    supporting the neopenis by attaching a proximal end of the implantable penile prosthesis to a descending ramus of the pelvis.

2. The method of claim 1, comprising supporting the neopenis by attaching the artificial tunica to the descending ramus of the pelvis.

3. The method of claim 1, wherein the artificial tunica is configured to reduce movement of the pair of malleable penile inserts off a longitudinal axis of the neopenis.

4. The method of claim 1, wherein the artificial tunica comprises an elastomer molded around the pair of malleable penile inserts and a longitudinal trough formed in the elastomer on an exterior of the artificial tunica, the method further comprising placing a neourethra in the longitudinal trough of the artificial tunica.

5. The method of claim 1, further comprising:
    attaching an artificial crus penis recess to the tissue of the pelvis; and
    supporting the neopenis by securing the proximal end of the implantable penile prosthesis within the artificial crus penis recess.

6. The method of claim 1, further comprising:
    forming an artificial crus penis recess by forming a tissue pocket alongside each descending ramus of the pelvis; and
    supporting the neopenis by securing the proximal end of the implantable penile prosthesis within the tissue pocket alongside each of the descending rami of the pelvis.

7. The method of claim 1, further comprising removing a cervix by dissecting the cervix away from the vagina.

8. The method of claim 1, further comprising removing tissue from a cervix and forming a glans penis with the tissue removed from the cervix; and attaching the glans penis to the inverted vagina.

9. The method of claim 1, further comprising forming a glans penis at a distal end of the neopenis with tissue of a cervix.

* * * * *